United States Patent [19]
Halczenko et al.

[11] Patent Number: 6,015,817
[45] Date of Patent: Jan. 18, 2000

[54] INHIBITORS OF FARNESYL-PROTEIN TRANSFERASE

[75] Inventors: Wasyl Halczenko, Lansdale; Craig A. Stump, Schwenksville, both of Pa.

[73] Assignee: Merck & Co., Inc., Rahway, N.J.

[21] Appl. No.: 08/984,732

[22] Filed: Dec. 4, 1997

Related U.S. Application Data

[60] Provisional application No. 60/032,126, Dec. 5, 1996.

[51] Int. Cl.$^7$ ....................... A61K 31/435; C07D 495/04
[52] U.S. Cl. ............................................ 514/301; 546/114
[58] Field of Search ...................................... 546/114, 115, 546/117, 118; 548/311.7, 312.1; 514/301, 302, 303, 397

[56] References Cited

U.S. PATENT DOCUMENTS

| | | | |
|---|---|---|---|
| 5,141,851 | 8/1992 | Brown et al. | 435/15 |
| 5,223,625 | 6/1993 | Van Winjngaarden et al. | 546/70 |
| 5,238,922 | 8/1993 | Graham et al. | 514/18 |
| 5,340,828 | 8/1994 | Graham et al. | 514/357 |
| 5,352,705 | 10/1994 | Deana et al. | 514/630 |
| 5,439,918 | 8/1995 | De Solms et al. | 514/307 |
| 5,504,212 | 4/1996 | De Solms et al. | 546/336 |
| 5,534,537 | 7/1996 | Ciccarone et al. | 514/397 |
| 5,578,629 | 11/1996 | Ciccarone et al. | 514/397 |
| 5,627,202 | 5/1997 | DeSolms | 514/307 |
| 5,652,257 | 7/1997 | Anthony et al. | 514/399 |
| 5,710,171 | 1/1998 | Dinsmore et al. | 514/396 |
| 5,780,492 | 7/1998 | Dinsmore et al. | 514/397 |

FOREIGN PATENT DOCUMENTS

| | | |
|---|---|---|
| 564356 | 10/1993 | European Pat. Off. . |
| 0 618 221 A2 | 10/1994 | European Pat. Off. . |
| 0 675 112 A1 | 10/1995 | European Pat. Off. . |
| 0 696 593 A2 | 2/1996 | European Pat. Off. . |
| 5-286941 | 11/1993 | Japan . |
| WO 96/00736 | 1/1996 | WIPO . |
| WO 96/24612 | 8/1996 | WIPO . |
| WO 97/18813 | 5/1997 | WIPO . |
| WO 97/30053 | 8/1997 | WIPO . |

OTHER PUBLICATIONS

Gibbs, J.B. et al., "Selective Inhibition of Farnesyl–Protein Transferase Blocks Ras Processing in Vivo," The Journal of Biological Chemistry, vol. 268, No. 11, pp. 7617–7620 (1993).

Goldstein, J.L. et al., "Nonfarnesylated Tetrapeptide Inhibitors of Protein Farnesyltransferase," The Journal of Biological Chemistry, vol. 266, No. 24, pp. 15575–15578 (1991).

Graham, S.L., "Inhibitors of protein farnesylation: a new approach to cancer chemotherapy," Exp. Opin. Ther. Patents vol. 5 (12), pp. 1269–1285 (1995).

James, G.L. et al., "Benzodiazepine Peptidomimetics: Potent Inhibitors of Ras Farnesylation in Animals Cells," Science, vol. 260 pp. 1937–1942 (1993).

James, G.L. et al., "Benzodiazepine Peptidomimetic BZA–5B Interrupts the MAP Kinase Activation Pathway in H–Ras–transformed Rat–1 Cells, but Not in Untransformed Cells," The Journal of Biological Chemistry, vol. 269, No. 44, pp. 27705–27714 (1994).

James, G., et al., "Polylsine and CVIM Sequences of K–RasB Dictate Specificity of Prenylation and Confer Resistance to Benzodiazepine Peptidomimetic in Vitro," The Journal of Biological Chemistry, vol. 270, No. 11, pp. 6221–6226 (1995).

Kohl, N.E., et al., "Inhibition of farnesyltransferase induces regression of mammary and salivary carcinomas in ras transgenic mice," Nature Medicine, vol. 1, No. 8, pp. 792–797 (1995).

Kohl, N.E. et al., "Protein farnesyltransferase inhibitors block the growth of ras–dependent tumors in nude mice", Proc. Natl. Acad. Sci. USA, Med. Science, vol. 91, pp. 9141–9145 (1994).

Kohl, N.E. et al., "Selective Inhibition of ras–Dependent Transformation by a farnesyltransferase Inhibitor", Science, vol. 260, pp. 1934–1937 (1993).

Pompilano, D.L., "Steady–State Kinetic Mechanism of Ras Farnesyl:Protein Transferase," Biochemistry, vol. 31, pp. 3800–3807 (1992).

Sepp–Lorenzino, L., et al., "A Peptidomimetic Inhibitor of Farnesyl:Protein Transferase Blocks the Anchorage–dependent and –independent Growth of Human Tumor Cell Lines," Cancer Research, vol. 55, pp. 5302–5309 (1995).

Chem. Abst. ,vol. 123–No. 33051, 1995.

*Primary Examiner*—Bernard Dentz
*Attorney, Agent, or Firm*—Dianne Pecoraro; David A. Muthard; Mark R. Daniel

[57] ABSTRACT

The present invention is directed to compounds which inhibit farnesyl-protein transferase (FTase) and the farnesylation of the oncogene protein Ras. The invention is further directed to chemotherapeutic compositions containing the compounds of this invention and methods for inhibiting farnesyl-protein transferase and the farnesylation of the oncogene protein Ras.

30 Claims, No Drawings

```
                            SEQUENCE LISTING (1) GENERAL INFORMATION:

(iii) NUMBER OF SEQUENCES: 14

(2) INFORMATION FOR SEQ ID NO:1:

(i) SEQUENCE CHARACTERISTICS:
           (A) LENGTH: 15 amino acids
           (B) TYPE: amino acid
           (C) STRANDEDNESS: single
           (D) TOPOLOGY: linear (ii) MOLECULE TYPE: protein (xi) SEQUENCE DESCRIPTION: SEQ ID NO:1:

Gly Lys Lys Lys Lys Lys Ser Lys Thr Lys Cys Val Ile Met
  1               5                   10                  15

(2) INFORMATION FOR SEQ ID NO:2:

(i) SEQUENCE CHARACTERISTICS:
           (A) LENGTH: 86 base pairs
           (B) TYPE: nucleic acid
           (C) STRANDEDNESS: single
           (D) TOPOLOGY: linear (ii) MOLECULE TYPE: Genomic DNA (xi) SEQUENCE DESCRIPTION: SEQ ID NO:2:

TCTCCTCGAG GCCACCATGG GGAGTAGCAA GAGCAAGCCT AAGGACCCCA GCCAGCGCCG      60

GATGACAGAA TACAAGCTTG TGGTGG                                          86

(2) INFORMATION FOR SEQ ID NO:3:

(i) SEQUENCE CHARACTERISTICS:
           (A) LENGTH: 33 base pairs
           (B) TYPE: nucleic acid
           (C) STRANDEDNESS: single
           (D) TOPOLOGY: linear (ii) MOLECULE TYPE: Genomic DNA (xi) SEQUENCE DESCRIPTION: SEQ ID NO:3:

CACATCTAGA TCAGGACAGC ACAGACTTGC AGC                                  33

(2) INFORMATION FOR SEQ ID NO:4:

(i) SEQUENCE CHARACTERISTICS:
           (A) LENGTH: 41 base pairs
           (B) TYPE: nucleic acid
           (C) STRANDEDNESS: single
           (D) TOPOLOGY: linear (ii) MOLECULE TYPE: Genomic DNA
```

(xi) SEQUENCE DESCRIPTION: SEQ ID NO:4:

TCTCCTCGAG GCCACCATGA CAGAATACAA GCTTGTGGTG G          41

(2) INFORMATION FOR SEQ ID NO:5:

(i) SEQUENCE CHARACTERISTICS:
      (A) LENGTH: 38 base pairs
      (B) TYPE: nucleic acid
      (C) STRANDEDNESS: single
      (D) TOPOLOGY: linear (ii) MOLECULE TYPE: Genomic DNA (xi) SEQUENCE DESCRIPTION: SEQ ID NO:5:

CACTCTAGAC TGGTGTCAGA GCAGCACACA CTTGCAGC               38

(2) INFORMATION FOR SEQ ID NO:6:

(i) SEQUENCE CHARACTERISTICS:
      (A) LENGTH: 38 base pairs
      (B) TYPE: nucleic acid
      (C) STRANDEDNESS: single
      (D) TOPOLOGY: linear (ii) MOLECULE TYPE: Genomic DNA (xi) SEQUENCE DESCRIPTION: SEQ ID NO:6:

GAGAGAATTC GCCACCATGA CGGAATATAA GCTGGTGG               38

(2) INFORMATION FOR SEQ ID NO:7:

(i) SEQUENCE CHARACTERISTICS:
      (A) LENGTH: 33 base pairs
      (B) TYPE: nucleic acid
      (C) STRANDEDNESS: single
      (D) TOPOLOGY: linear (ii) MOLECULE TYPE: Genomic DNA (xi) SEQUENCE DESCRIPTION: SEQ ID NO:7:

GAGAGTCGAC GCGTCAGGAG AGCACACACT TGC                    33

(2) INFORMATION FOR SEQ ID NO:8:

(i) SEQUENCE CHARACTERISTICS:
      (A) LENGTH: 22 base pairs
      (B) TYPE: nucleic acid
      (C) STRANDEDNESS: single
      (D) TOPOLOGY: linear (ii) MOLECULE TYPE: Genomic DNA (xi) SEQUENCE DESCRIPTION: SEQ ID NO:8:

CCGCCGGCCT GGAGGAGTAC AG                                22

(2) INFORMATION FOR SEQ ID NO:9:

(i) SEQUENCE CHARACTERISTICS:
      (A) LENGTH: 38 base pairs
      (B) TYPE: nucleic acid
      (C) STRANDEDNESS: single
      (D) TOPOLOGY: linear (ii) MOLECULE TYPE: Genomic DNA (xi) SEQUENCE DESCRIPTION: SEQ ID NO:9:

GAGAGAATTC GCCACCATGA CTGAGTACAA ACTGGTGG               38

(2) INFORMATION FOR SEQ ID NO:10:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:10:

GAGAGTCGAC TTGTTACATC ACCACACATG GC        32

(2) INFORMATION FOR SEQ ID NO:11:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:11:

GTTGGAGCAG TTGGTGTTGG G        21

(2) INFORMATION FOR SEQ ID NO:12:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:12:

GAGAGGTACC GCCACCATGA CTGAATATAA ACTTGTGG        38

(2) INFORMATION FOR SEQ ID NO:13:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:13:

CTCTGTCGAC GTATTTACAT AATTACACAC TTTGTC        36

(2) INFORMATION FOR SEQ ID NO:14:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:14:

GTAGTTGGAG CTGTTGGCGT AGGC        24

INHIBITORS OF FARNESYL-PROTEIN TRANSFERASE

DOMESTIC PRIORITY CLAIM

This application claims priority from the U.S. provisional application No. 60/032,126, filed on Dec. 5, 1996.

BACKGROUND OF THE INVENTION

The Ras protein is part of a signalling pathway that links cell surface growth factor receptors to nuclear signals initiating cellular proliferation. Biological and biochemical studies of Ras action indicate that Ras functions like a G-regulatory protein. In the inactive state, Ras is bound to GDP. Upon growth factor receptor activation Ras is induced to exchange GDP for GTP and undergoes a conformational change. The GTP-bound form of Ras propagates the growth stimulatory signal until the signal is terminated by the intrinsic GTPase activity of Ras, which returns the protein to its inactive GDP bound form (D. R. Lowy and D. M. Willumsen, *Ann. Rev. Biochem.* 62:851–891 (1993)). Mutated ras genes are found in many human cancers, including colorectal carcinoma, exocrine pancreatic carcinoma, and myeloid leukemias. The protein products of these genes are defective in their GTPase activity and constitutively transmit a growth stimulatory signal.

Ras must be localized to the plasma membrane for both normal and oncogenic functions. At least 3 post-translational modifications are involved with Ras membrane localization, and all 3 modifications occur at the C-terminus of Ras. The Ras C-terminus contains a sequence motif termed a "CAAX" or "Cys-Aaa$^1$-Aaa$^2$-Xaa" box (Cys is cysteine, Aaa is an aliphatic amino acid, the Xaa is any amino acid) (Willumsen et al., *Nature* 310:583–586 (1984)). Depending on the specific sequence, this motif serves as a signal sequence for the enzymes farnesyl-protein transferase or geranylgeranyl-protein transferase, which catalyze the alkylation of the cysteine residue of the CAAX motif with a $C_{15}$ or $C_{20}$ isoprenoid, respectively. (S. Clarke., *Ann. Rev. Biochem.* 61:355–386 (1992); W. R. Schafer and J. Rine, *Ann. Rev. Genetics* 30:209–237 (1992)). The Ras protein is one of several proteins that are known to undergo post-translational farnesylation. Other farnesylated proteins include the Ras-related GTP-binding proteins such as Rho, fungal mating factors, the nuclear lamins, and the gamma subunit of transducin. James, et al., *J. Biol. Chem.* 269, 14182 (1994) have identified a peroxisome associated protein Pxf which is also farnesylated. James, et al., have also suggested that there are farnesylated proteins of unknown structure and function in addition to those listed above.

Inhibition of farnesyl-protein transferase has been shown to block the growth of Ras-transformed cells in soft agar and to modify other aspects of their transformed phenotype. It has also been demonstrated that certain inhibitors of farnesyl-protein transferase selectively block the processing of the Ras oncoprotein intracellularly (N. E. Kohl et al., *Science*, 260:1934–1937 (1993) and G. L. James et al., *Science*, 260:1937–1942 (1993). Recently, it has been shown that an inhibitor of farnesyl-protein transferase blocks the growth of ras-dependent tumors in nude mice (N. E. Kohl et al., *Proc. Natl. Acad. Sci U.S.A.*, 91:9141–9145 (1994) and induces regression of mammary and salivary carcinomas in ras transgenic mice (N. E. Kohl et al., *Nature Medicine*, 1:792–797 (1995).

Indirect inhibition of farnesyl-protein transferase in vivo has been demonstrated with lovastatin (Merck & Co., Rahway, N.J.) and compactin (Hancock et al., ibid; Casey et al., ibid; Schafer et al., *Science* 245:379 (1989)). These drugs inhibit HMG-CoA reductase, the rate limiting enzyme for the production of polyisoprenoids including farnesyl pyrophosphate. Farnesyl-protein transferase utilizes farnesyl pyrophosphate to covalently modify the Cys thiol group of the Ras CAAX box with a farnesyl group (Reiss et al., *Cell*, 62:81–88 (1990); Schaber et al., *J. Biol. Chem.*, 265:14701–14704 (1990); Schafer et al., *Science*, 249:1133–1139 (1990); Manne et al., *Proc. Natl. Acad. Sci USA*, 87:7541–7545 (1990)). Inhibition of farnesyl pyrophosphate biosynthesis by inhibiting HMG-CoA reductase blocks Ras membrane localization in cultured cells. However, direct inhibition of farnesyl-protein transferase would be more specific and attended by fewer side effects than would occur with the required dose of a general inhibitor of isoprene biosynthesis.

Inhibitors of farnesyl-protein transferase (FPTase) have been described in two general classes. The first are analogs of farnesyl diphosphate (FPP), while the second class of inhibitors is related to the protein substrates (e.g., Ras) for the enzyme. The peptide derived inhibitors that have been described are generally cysteine containing molecules that are related to the CAAX motif that is the signal for protein prenylation. (Schaber et al., ibid; Reiss et. al., ibid; Reiss et al., *PNAS*, 88:732–736 (1991)). Such inhibitors may inhibit protein prenylation while serving as alternate substrates for the farnesyl-protein transferase enzyme, or may be purely competitive inhibitors (U.S. Pat. No. 5,141,851, University of Texas; N. E. Kohl et al., *Science*, 260:1934–1937 (1993); Graham, et al., *J. Med. Chem.*, 37, 725 (1994)). In general, deletion of the thiol from a CAAX derivative has been shown to dramatically reduce the inhibitory potency of the compound. However, the thiol group potentially places limitations on the therapeutic application of FPTase inhibitors with respect to pharmacokinetics, pharmacodynamics and toxicity. Therefore, a functional replacement for the thiol is desirable.

It has recently been shown that farnesyl-protein transferase inhibitors are inhibitors of proliferation of vascular smooth muscle cells and are therefore useful in the prevention and therapy of arteriosclerosis and diabetic disturbance of blood vessels (JP H7–112930). It has also recently been disclosed that certain 1,2,3,4-tetrahydroisoquinoline peptidomimetic compounds, some of which incorporate an imidazole moiety, are inhibitors of FPTase (U.S. Pat. No. 5,439,918, EP 0 618 221 A2 and EP 0 675 112 A1).

It is, therefore, an object of this invention to develop novel peptidomimetic compounds that do not have a thiol moiety, and that will inhibit fariesyl-protein transferase and thus, the post-translational farnesylation of proteins. It is a further object of this invention to develop chemotherapeutic compositions containing the compounds of this invention and methods for producing the compounds of this invention.

SUMMARY OF THE INVENTION

The present invention comprises substituted [4.3.0]-nitrogen containing ring systems and homologous compounds which inhibit farnesyl-protein transferase. Furthermore, these compounds differ from such heterocyclic compounds previously described as inhibitors of farnesyl-protein transferase with respect to the alkyl or heteroatom containing linker between the ring-nitrogen and the imidazolyl moiety, and with respect to the lack of a thiol moiety in the instant compounds. Further contained in this invention are chemotherapeutic compositions containing these farnesyl transferase inhibitors and methods for their production.

The compounds of this invention are illustrated by the formulae I and A:

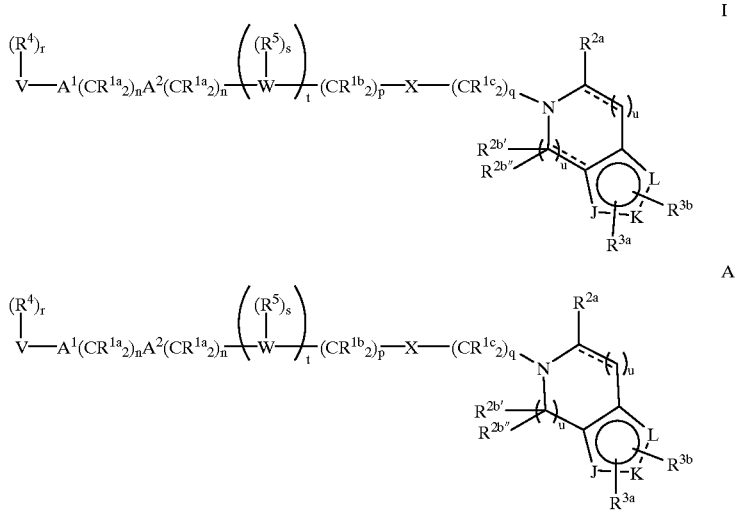

DETAILED DESCRIPTION OF THE INVENTION

The compounds of this invention are useful in the inhibition of farnesyl-protein transferase and the farnesylation of the oncogene protein Ras. In a first embodiment of this invention, the inhibitors of farnesyl-protein transferase are illustrated by the formula I:

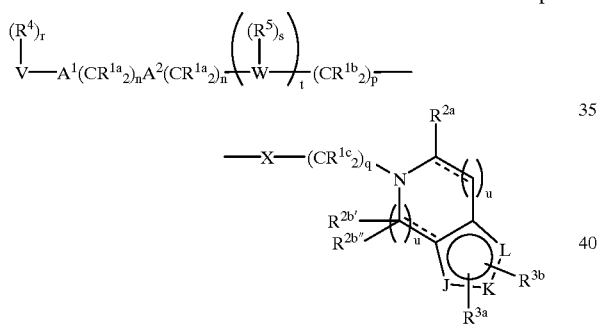

wherein:

$R^{1a}$, $R^{1b}$ and $R^{1c}$ are independently selected from:
a) hydrogen,
b) unsubstituted or substituted aryl, unsubstituted or substituted heterocycle, $C_3$–$C_{10}$ cycloalkyl, $C_2$–$C_6$ alkenyl, $C_2$–$C_6$ alkynyl, $R^8O$—, $R^9S(O)_m$—, $R^8C(O)NR^8$—, CN, $NO_2$, $(R^8)_2N$—$C(NR^8)$—, $R^8C(O)$—, $R^8OC(O)$—, $N_3$, —$N(R^8)_2$, or $R^9OC(O)NR^8$—,
c) $C_1$–$C_6$ alkyl unsubstituted or substituted by unsubstituted or substituted aryl, heterocyclic, $C_3$–$C_{10}$ cycloalkyl, $C_2$–$C_6$ alkenyl, $C_2$–$C_6$ alkynyl, $R^8O$—, $R^9S(O)_m$—, $R^8C(O)NR^8$—, CN, $(R^8)_2N$—$C(NR^8)$—, $R^8C(O)$—, $R^8OC(O)$—, $N_3$, —$N(R^8)_2$, or $R^9OC(O)$—$NR^8$—, provided that $R^{1a}$ is not unsubstituted or substituted imidazolyl;

$R^{2a}$, $R^{2b'}$ and $R^{2b''}$ are independently hydrogen or —$(CR^{11}_2)_vA^3(CR^{12}_2)_wR^{13}$; or $R^{2b'}$ and $R^{2b''}$ are combined as O;

$R^{3a}$ and $R^{3b}$ are independently selected from:
a) hydrogen,
b) unsubstituted or substituted aryl, unsubstituted or substituted heterocycle, unsubstituted or substituted $C_3$–$C_{10}$ cycloalkyl, unsubstituted or substituted $C_2$–$C_6$ alkenyl, $C_2$–$C_6$ alkynyl, halogen, $C_1$–$C_6$ perfluoroalkyl, $R^9O$—, $R^9S(O)_m$—, $R^8C(O)NR^8$—, $(R^8)_2NC(O)$—, $R^9C(O)O$—, $R^8_2N$—$C(NR^8)$—, CN, $NO_2$, $R^8C(O)$—, $N_3$, —$N(R^8)_2$, or $R^9OC(O)NR^8$—,
c) unsubstitued $C_1$–$C_6$ alkyl,
d) substituted $C_1$–$C_6$ alkyl wherein the substituent on the substituted $C_1$–$C_6$ alkyl is selected from unsubstituted or substituted aryl, unsubstituted or substituted heterocyclic, $C_3$–$C_{10}$ cycloalkyl, $C_2$–$C_6$ alkenyl, $C_2$–$C_6$ alkynyl, $R^9O$—, $R^9S(O)_m$—, $R^8C(O)NR^8$—, $(R^8)_2NC(O)$—, $R^8_2N$—$C(NR^8)$—, CN, $R^8C(O)$—, $N_3$, —$N(R^8)_2$, and $R^9OC(O)$—$NR^8$—;

$R^4$ is independently selected from:
a) hydrogen,
b) unsubstituted or substituted aryl, unsubstituted or substituted heterocycle, $C_3$–$C_{10}$ cycloalkyl, $C_2$–$C_6$ alkenyl, $C_2$–$C_6$ alkynyl, perfluoroalkyl, F, Cl, Br, $R^8O$—, $R^9S(O)_m$—, $R^8C(O)NR^8$—, CN, $NO_2$, $R^8_2N$—$C(NR^8)$—, $R^8C(O)$—, $R^8OC(O)$—, $N_3$, —$N(R^8)_2$, or $R^9OC(O)NR^8$—, and
c) $C_1$–$C_6$ alkyl unsubstituted or substituted by aryl, heterocycle, $C_3$–$C_{10}$ cycloalkyl, $C_2$–$C_6$ alkenyl, $C_2$–$C_6$ alkynyl, perfluoroalkyl, F, Cl, Br, $R^8O$—, $R^9S(O)_m$—, $R^8C(O)NH$—, CN, $H_2N$—$C(NH)$—, $R^8C(O)$—, $R^8OC(O)$—, $N_3$, —$N(R^8)_2$, or $R^8OC(O)NH$—, provided that $R^4$ is not unsubstituted or substituted imidazolyl;

$R^5$ is independently selected from:
a) hydrogen,
b) $C_2$–$C_6$ alkenyl, $C_2$–$C_6$ alkynyl, $C_3$–$C_6$ cycloalkyl, perfluoroalkyl, F, Cl, Br, $R^8O$—, $R^9S(O)_m$—, $R^8C(O)NR^8$—, CN, $NO_2$, $(R^8)_2N$—$C$—$(NR^8)$—, $R^8C(O)$—, $R^8OC(O)$—, $N_3$, —$N(R^8)_2$, or $R^9OC(O)NR^8$—, and
c) $C_1$–$C_6$ alkil, unsubstituted or substituted by perfluoroalkyl, F, Cl, Br, $R^8O$—, $R^9S(O)_m$—, $R^8C(O)NR^8$—, CN, $(R^8)_2N$—$C(NR^8)$—, $R^8C(O)$—, $R^8OC(O)$—, $N_3$, —$N(R^8)_2$, or $R^9OC(O)NR^8$—;

$R^8$ is independently selected from hydrogen, $C_1$–$C_6$ alkyl, benzyl, 2,2,2-trifluoroethyl and aryl;

$R^9$ is independently selected from $C_1$–$C_6$ alkyl and aryl;

$R^{10}$ is selected from: H; $R^8C(O)$—; $R^9S(O)_m$—; unsubstituted or substituted $C_{1-4}$ alkyl, unsubstituted or substituted $C_{3-6}$ cycloalkyl, unsubstituted or substituted heterocycle, unsubstituted or substituted aryl, substituted aroyl, unsubstituted or substituted heteroaroyl, substituted arylsulfonyl, unsubstituted or substituted heteroarylsulfonyl, wherein the substituted group is substituted with one or two substituents selected from:
a) $C_{1-4}$ alkoxy,
b) aryl or heterocycle,
c) halogen,
d) HO, e)
$$\underset{O}{\overset{R^9}{\underset{\|}{\text{C}}}}$$

f)
$$\underset{O}{\overset{OR^8}{\underset{\|}{\text{C}}}}$$

g) —S(O)$_m$R$^9$, h) N(R$^8$)$_2$, or
i) $C_{3-6}$ cycloalkyl;

$R^{11}$ and $R^{12}$ are independently selected from:
a) hydrogen,
b) $C_1$–$C_6$ alkyl unsubstituted or substituted by $C_2$–$C_{20}$ alkenyl, R$^8$O—, R$^9$S(O)$_m$—, R$^8$C(O)NR$^8$—, CN, N$_3$, (R$^8$)$_2$N—C(NR$^8$)—, R$^8$C(O)—, —N(R$^8$)$_2$, or R$^9$OC(O)NR$^8$—,
c) unsubstituted or substituted aryl, unsubstituted or substituted heterocycle, $C_3$–$C_{10}$ cycloalkyl, $C_2$–$C_{20}$ alkenyl, halogen, R$^8$O—, R$^9$S(O)$_m$—, R$^8$C(O)NR$^8$—, CN, NO$_2$, (R$^8$)$_2$N—C(NR$^8$)—, R$^8$C(O)—, N$_3$, —N(R$^8$)$_2$, or R$^9$OC(O)NR$^8$—, and
d) $C_1$–$C_6$ alkyl substituted with an unsubstituted or substituted group selected from aryl, heterocyclic and $C_3$–$C_{10}$ cycloalkyl;

$R^{13}$ is selected from:
a) hydrogen,
b) substituted or unsubstituted aryl, substituted or unsubstituted heterocycle, $C_3$–$C_{10}$ cycloalkyl, $C_2$–$C_{20}$ alkenyl, $C_2$–$C_{20}$ alkynyl, $C_1$–$C_{20}$ perfluoroalkyl, allyloxy, F, Cl, Br, R$^8$O—, R$^9$S(O)$_m$—, R$^8$C(O)NR$^8$—, CN, NO$_2$, R$^8$$_2$N—C(NR$^8$)—, R$^8$C(O)—, N$_3$, —N(R$^8$)$_2$, (R$^9$)$_2$NC(O)— or R$^9$OC(O)NR$^8$—, and
c) $C_1$–$C_6$ alkyl unsubstituted or substituted by substituted or unsubstitute d aryl, substituted or unsubstituted heterocycle, $C_3$–$C_{10}$ cycloalkyl, $C_2$–$C_{20}$ alkenyl, $C_2$–$C_{20}$ alkynyl, $C_2$–$C_{20}$ perfluoroalkyl, F, Cl, Br, R$^8$O—, R$^9$S(O)$_m$—, R$^8$C(O)NH—, CN, H$_2$N—C(NH)—, R$^8$C(O)—, N$_3$, —N(R$^8$)$_2$, or R$^9$OC(O)NH—;

$A^1$ and $A^2$ are independently selected from: a bond, —CH=CH—, —C≡C—, —C(O)—, —C(O)NR$^8$—, —NR$^8$C(O)—, O, —N(R$^8$)—, —S(O)$_2$N(R$^8$)—, —N(R$^8$)S(O)$_2$—, or —S(O)$_m$;

$A^3$ are independently selected from: a bond, —CH=CH—, —C≡C—, —C(O)—, —C(O)NR$^{10}$—, —NR$^{10}$C(O)—, O, —N(R$^{10}$)—, —S(O)$_2$N(R$^{10}$)—, —N(R$^{10}$)S(O)$_2$—, or —S(O)$_m$;

J, K and L are independently selected from: S, N, O, NH and CH;

V is selected from:
a) hydrogen,
b) heterocycle,
c) aryl,
d) $C_1$–$C_{20}$ alkyl wherein from 0 to 4 carbon atoms are replaced with a a heteroatom selected from O, S, and N, and
e) $C_2$–$C_{20}$ alkenyl,
provided that V is not hydrogen if $A^1$ is —S(O)$_m$ and V is not hydrogen if $A^1$ is a bond, n is 0 and $A^2$ is —S(O)$_m$;
and provided that V is not imidazolyl;

W is a heterocycle;
X is a bond, —S(O)$_m$—, O or —C(=O)—;
m is 0, 1 or 2;
n is 0, 1, 2, 3 o 4;
p is 0, 1, 2, 3 or 4;
q is 0, 1, 2, 3 or 4, provided that q is not 0 or 1 if X is O;
r is 0 to 5, provided that r is 0 when V is hydrogen;
s is 1 or 2;
t is 0 or 1;
u is independently 0,1 or 2;
v is 0, 1, 2, 3 or 4, provided that v is not 0 when $A^3$ is —NR$^{10}$C(O)—, O, —N(R$^{10}$)—, —S(O)$_2$N(R$^{10}$)—, —N(R$^{10}$)S(O)$_2$—, or S(O)$_m$;
w is 0, 1, 2, 3 or 4; and
the dashed lines represent optional double bonds;
or an optical isomer or a pharmaceutically acceptable salt thereof.

In another embodiment of this invention, the inhibitors of farnesyl-protein transferase are illustrated by the formula A:

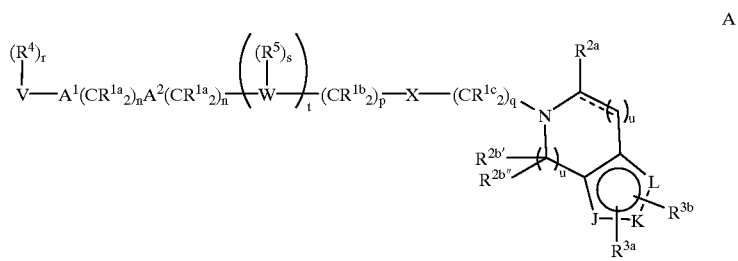

A wherein:

$R^{1a}$, $R^{1b}$ and $R^{1c}$ are independently selected from:
a) hydrogen.,
b) unsubstituted or substituted aryl, unsubstituted or substituted heterocycle, $C_3$–$C_{10}$ cycloalkyl, $C_2$–$C_6$ alkenyl, $C_2$–$C_6$ alkynyl, R$^8$O—, R$^9$S(O)$_m$—, R$^8$C(O)

NR$^8$—, CN, NO$_2$, (R$^8$)$_2$N—C(NR$^8$)—, R$^8$C(O)—, R$^8$OC(O)—, N$_3$, —N(R$^8$)$_2$, or R$^9$OC(O)NR$^8$—, c) C$_1$–C$_6$ alkyl unsubstituted or substituted by unsubstituted or substituted aryl, heterocyclic, C$_3$–C$_{10}$ cycloalkyl, C$_2$–C$_6$ alkenyl, C$_2$–C$_6$ alkynyl, R$^8$O—, R$^9$S(O)$_m$—, R$^8$C(O)NR$^8$—, CN, (R$^8$)$_2$N—C(NR$^8$)—, R$^8$C(O)—, R$^8$OC(O)—, N$_3$, —N(R$^8$)$_2$, or R$^9$OC(O)—NR$^8$—, provided that R$^{1a}$ is not unsubstituted or substituted imidazolyl;

R$^{2a}$, R$^{2b'}$ and R$^{2b''}$ are independently hydrogen or —(CR$^{11}_2$)$_v$A$^3$(CR$^{12}_2$)$_w$R$^{13}$; or R$^{2b'}$ and R$^{2b''}$ are combined as O;

R$^{3a}$ and R$^{3b}$ are independently selected from:
a) hydrogen,
b) unsubstituted or substituted aryl, unsubstituted or substituted heterocycle, unsubstituted or substituted C$_3$–C$_{10}$ cycloalkyl, unsubstituted or substituted C$_2$–C$_6$ alkenyl, C$_2$–C$_6$ alkynyl, halogen, C$_1$–C$_6$ perfluoroalkyl, R$^9$O—, R$^9$S(O)$_m$—, R$^8$C(O)NR$^8$—, (R$^8$)$_2$NC(O)—, R$^9$C(O)O—, R$^8_2$N—C(NR$^8$)—, CN, NO$_2$, R$^8$C(O)—, N$_3$, —N(R$^8$)$_2$, or R$^9$OC(O)NR$^8$—,
c) unsubstitued C$_1$–C$_6$ alkyl,
d) substituted C$_1$–C$_6$ alkyl wherein the substituent on the substituted C$_1$–C$_6$ alkyl is selected from unsubstituted or substituted aryl, unsubstituted or substituted heterocyclic, C$_3$–C$_{10}$ cycloalkyl, C$_2$–C$_6$ alkenyl, C$_2$–C$_6$ alkynyl, R$^9$O—, R$^9$S(O)$_m$—, R$^8$C(O)NR$^8$—, (R$^8$)$_2$NC(O)—, R$^8_2$N—C(NR$^8$)—, CN, R$^8$C(O)—, N$_3$, —N(R$^8$)$_2$, and R$^9$OC(O)—NR$^8$—;

R$^4$ is independently selected from:
a) hydrogen,
b) unsubstituted or substituted aryl, unsubstituted or substituted heterocycle, C$_3$–C$_{10}$ cycloalkyl, C$_2$–C$_6$ alkenyl, C$_2$–C$_6$ alkynyl, perfluoroalkyl, F, Cl, Br, R$^8$O—, R$^9$S(O)$_m$—, R$^8$C(O)NR$^8$—, CN, NO$_2$, R$^8_2$N—C(NR$^8$)—, R$^8$C(O)—, R$^8$OC(O)—, N$_3$, —N(R$^8$)$_2$, or R$^9$OC(O)NR$^8$—, and
c) C$_1$–C$_6$ alkyl unsubstituted or substituted by aryl, heterocycle, C$_3$–C$_{10}$ cycloalkyl, C$_2$–C$_6$ alkenyl, C$_2$–C$_6$ alkynyl, perfluoroalkyl, F, Cl, Br, R$^8$O—, R$^9$S(O)$_m$—, R$^8$C(O)NH—, CN, H$_2$N—C(NH)—, R$^8$C(O)—, R$^8$OC(O)—, N$_3$, —N(R$^8$)$_2$, or R$^8$OC(O)NH—, provided that R$^4$ is not unsubstituted or substituted imidazolyl;

R$^5$ is independently selected from:
a) hydrogen,
b) C$_2$–C$_6$ alkenyl, C$_2$–C$_6$ alkynyl, C$_3$–C$_6$ cycloalkyl, perfluoroalkyl, F, Cl, Br, R$^8$O—, R$^9$S(O)$_m$—, R$^8$C(O)NR$^8$—, CN, NO$_2$, (R$^8$)$_2$N—C—(NR$^8$)—, R$^8$C(O)—, R$^8$OC(O)—, N$_3$, —N(R$^8$)$_2$, or R$^9$OC(O)NR$^8$—, and
c) C$_1$–C$_6$ alkyl, unsubstituted or substituted by perfluoroalkyl, F, Cl, Br, R$^8$O—, R$^9$S(O)$_m$—, R$^8$C(O)NR$^8$—, CN, (R$^8$)$_2$N—C(NR$^8$)—, R$^8$C(O)—, R$^8$OC(O)—, N$_3$, —N(R$^8$)$_2$, or R$^9$OC(O)NR$^8$—;

R$^8$ is independently selected from hydrogen, C$_1$–C$_6$ alkyl, benzyl, 2,2,2-trifluoroethyl and aryl;

R$^9$ is independently selected from C$_1$–C$_6$ alkyl and aryl;

R$^{10}$ is selected from: H; R$^8$C(O)—; R$^9$S(O)$_m$—; unsubstituted or substituted C$_{1-4}$ alkyl, unsubstituted or substituted C$_{3-6}$ cycloalkyl, unsubstituted or substituted heterocycle, unsubstituted or substituted aryl, substituted aroyl, unsubstituted or substituted heteroaroyl, substituted arylsulfonyl, unsubstituted or substituted heteroarylsulfonyl, wherein the substituted group is substituted with one or two substituents selected from:
a) C$_{1-4}$ alkoxy,
b) aryl or heterocycle,
c) halogen,
d) HO,

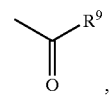
e)

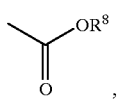
f)

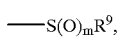
g)

h) N(R$^8$)$_2$, or
i) C$_{3-6}$ cycloalkyl;

R$^{11}$ and R$^{12}$ are independently selected from:
a) hydrogen,
b) C$_1$–C$_6$ alkyl unsubstituted or substituted by C$_2$–C$_{20}$ alkenyl, R$^8$O—, R$^9$S(O)$_m$—, R$^8$C(O)NR$^8$—, CN, N$_3$, (R$^8$)$_2$N—C(NR$^8$)—, R$^8$C(O)—, —N(R$^8$)$_2$, or R$^9$OC(O)NR$^8$—,
c) unsubstituted or substituted aryl, unsubstituted or substituted heterocycle, C$_3$–C$_{10}$ cycloalkyl, C$_2$–C$_{20}$ alkenyl, halogen, R$^8$O—, R$^9$S(O)$_m$—, R$^8$C(O)NR$^8$—, CN, NO$_2$, (R$^8$)$_2$N—C(NR$^8$)—, R$^8$C(O)—, N$_3$, —N(R$^8$)$_2$, or R$^9$OC(O)NR$^8$—, and
d) C$_1$–C$_6$ alkyl substituted with an unsubstituted or substituted group selected from aryl, heterocyclic and C$_3$–C$_{10}$ cycloalkyl;

R$^{13}$ is selected from:
a) hydrogen,
b) substituted or unsubstituted aryl, substituted or unsubstituted heterocycle, C$_3$–C$_{10}$ cycloalkyl, C$_2$–C$_{20}$ alkenyl, C$_2$–C$_{20}$ alkynyl, C$_1$–C$_{20}$ perfluoroalkyl, allyloxy, F, Cl, Br, R$^8$O—, R$^9$S(O)$_m$—, R$^8$C(O)NR$^8$—, CN, NO$_2$, R$^8_2$N—C(NR$^8$)—, R$^8$C(O)—, N$_3$, —N(R$^8$)$_2$, (R$^9$)$_2$NC(O)— or R$^9$OC(O)NR$^8$—, and
c) C$_1$–C$_6$ alkyl unsubstituted or substituted by substituted or unsubstituted aryl, substituted or unsubstituted heterocycle, C$_3$–C$_{10}$ cycloalkyl, C$_2$–C$_{20}$ alkenyl, C$_2$–C$_{20}$ alkynyl, C$_2$–C$_{20}$ perfluoroalkyl, F, Cl, Br, R$^8$O—, R$^9$S(O)$_m$—, R$^8$C(O)NH—, CN, H$_2$N—C(NH)—, R$^8$C(O)—, N$_3$, —N(R$^8$)$_2$, or R$^9$OC(O)NH—;

A$^1$ and A$^2$ are independently selected from: a bond, —CH=CH—, —C≡C—, —C(O)—, —C(O)NR$^8$—, —NR$^8$C(O)—, O, —N(R$^8$)—, —S(O)$_2$N(R$^8$)—, —N(R$^8$)S(O)$_2$—, or —S(O)$_m$;

A$^3$ are independently selected from: a bond, —CH=CH—, —C≡C—, —C(O)—, —C(O)NR$^{10}$—, —NR$^{10}$C(O)—, O, —N(R$^{10}$)—, —S(O)$_2$N(R$^{10}$)—, —N(R$^{10}$)S(O)$_2$—, or —S(O)$_m$;

J, K and L are independently selected from: S, N, O, NH and CH;

V is selected from:
a) hydrogen,
b) heterocycle,
c) aryl, d) $C_1$–$C_{20}$ alkyl wherein from 0 to 4 carbon atoms are replaced with a a heteroatom selected from O, S, and N, and
e) $C_2$–$C_{20}$ alkenyl, provided that V is not hydrogen if $A^1$ is —S(O)$_m$ and V is not hydrogen if $A_1$ is a bond, n is 0 and $A^2$ is —S(O)$_m$; and provided that V is not imidazolyl;

W is a heterocycle;

X is a bond, —S(O)$_m$—, O or —C(=O)—;

m is 0, 1 or 2;

n is 0, 1, 2, 3 or 4;

p is 0, 1, 2, 3 or 4;

q is 0, 1, 2, 3 or 4, provided that q is not 0 or 1 if X is O;

r is 0 to 5, provided that r is 0 when V is hydrogen;

s is 1 or 2;

t is 0 or 1;

u is independently 0,1 or 2;

v is 0, 1, 2, 3 or 4, provided that v is not 0 when $A^3$ is —NR$^{10}$C(O)—, O, —N(R$^{10}$)—, —S(O)$_2$N(R$^{10}$)—, —N(R$^{10}$)S(O)$_2$—, or S(O)$_m$;

w is 0, 1, 2, 3 or 4; and the dashed lines represent optional double bonds;

or an optical isomer or a pharmaceutically acceptable salt thereof.

A preferred embodiment of the compounds of this invention is illustrated by the following formula:

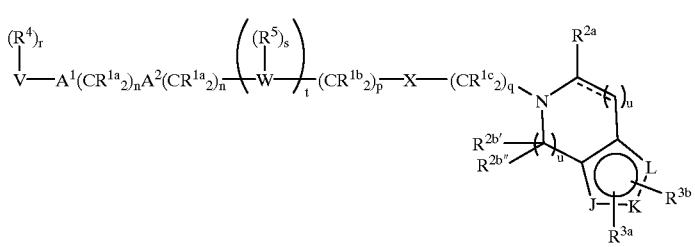

A wherein:
R$^{1a}$ and R$^{1c}$ are independently selected from: hydrogen, $C_3$–$C_{10}$ cycloalkyl, R$^8$O—, —N(R$^8$)$_2$, F or $C_1$–$C_6$ alkyl;

R$^{1b}$ is independently selected from:
a) hydrogen,
b) unsubstitulted or substituted aryl, unsubstituted or substituted heterocycle, $C_3$–$C_6$ cycloalkyl, R$^8$O—, —N(R$^8$)$_2$ or $C_2$–$C_6$ alkenyl,
c) $C_1$–$C_6$ alkyl unsubstituted or substituted by unsubstituted or substituted aryl, heterocycle, $C_3$–$C_6$ cycloalkyl, $C_2$–$C_6$ alkenyl, R$^8$O—, or —N(R$^8$)$_2$;

R$^{2a}$ and R$^{2b'}$ are independently selected from selected from: H; $C_1$–$C_6$ alkyl,

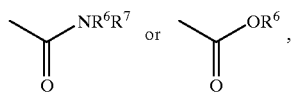

R$^{3a}$ and R$^{3b}$ are independently selected from:
a) hydrogen,
b) unsubstituted or substituted aryl, unsubstituted or substituted heterocycle, unsubstituted or substituted $C_3$–$C_{10}$ cycloalkyl, unsubstituted or substituted $C_2$–$C_6$ alkenyl, $C_2$–$C_6$ alkynyl, halogen, $C_1$–$C_6$ perfluoroalkyl, R$^9$O—, R$^9$S(O)$_m$—, R$^8$C(O)NR$^8$—, (R$^8$)$_2$NC(O)—, R$^9$C(O)O—, R$^8$$_2$N—C(NR$^8$)—, CN, NO$_2$, R$^8$C(O)—, N$_3$, —N(R$^8$)$_2$, or R$^9$OC(O)NR$^8$—,
c) unsubstituted $C_1$–$C_6$ alkyl,
d) substituted $C_1$–$C_6$ alkyl wherein the substituent on the substituted $C_1$–$C_6$ alkyl is selected from unsubstituted or substituted aryl, unsubstituted or substituted heterocyclic, $C_3$–$C_{10}$ cycloalkyl, $C_2$–$C_6$ alkenyl, $C_2$–$C_6$ alkynyl, R$^9$O—, R$^9$S(O)$_m$—, R$^8$C(O) NR$^8$—, (R$^8$)$_2$NC(O)—, R$^8$$_2$N—C(NR$^8$)—, CN, R$^8$C (O)—, N$_3$, —N(R$^8$)$_2$, and R$^9$OC(O)—NR$^8$—;

R$^4$ is independently selected from:
a) hydrogen,
b) $C_1$–$C_6$ alkyl, $C_2$–$C_6$ alkenyl, $C_2$–$C_6$ alkynyl, $C_1$–$C_6$ perfluoroalkyl, F, Cl, R$^8$O—, R$^8$C(O)NR$^8$—, CN, NO$_2$, (R$^8$)$_2$N—C(NR$^8$)—, R$^8$C(O)—, R$^8$OC(O)—, —N(R$^8$)$_2$, or R$^9$OC(O)NR$^8$—, and
c) $C_1$–$C_6$ alkyl substituted by $C_1$–$C_6$ perfluoroalkyl, R$^8$O—, R$^8$C(O)NR$^8$—, (R$^8$)$_2$N—C(NR$^8$)—, R$^8$C (O)—, R$^8$OC(O)—, —N(R$^8$)$_2$, or R$^9$OC(O)NR$^8$—;

R$^5$ is selected from:
a) hydrogen,
b) $C_2$–$C_6$ alkenyl, $C_2$–$C_6$ alkynyl, $C_3$–$C_6$ cycloalkyl, $C_1$–$C_6$ perfluoroalkyl, F, Cl, R$^8$O—, R$^9$S(O)$_m$—, R$^8$C(O)NR$^8$—, CN, NO$_2$, (R$^8$)$_2$N—C(NR$^8$)—, R$^8$C (O)—, R$^8$OC(O)—, —N(R$^8$)$_2$, or R$^9$OC(O)NR$^8$—, and c) $C_1$–$C_6$ alkyl unsubstituted or substituted by $C_1$–$C_6$ perfluoroalkyl, F, Cl, R$^8$O—, R$^9$S(O)$_m$—, R$^8$C(O) NR$^8$—, CN, (R$^8$)$_2$N—C(NR$^8$)—, R$^8$C(O)—, R$^8$OC (O)—, —N(R$^8$)$_2$, or R$^9$OC(O)NR$^8$—;

R$^6$ and R$^7$ are independently selected from:
H; $C_{1-4}$ alkyl, $C_{3-6}$ cycloalkyl, aryl, heterocycle, unsubstituted or substituted with one or two:
a) $C_{1-4}$ alkoxy,
b) halogen, or
c) substituted or unsubstituted aryl or substituted or unsubstituted heterocycle, R$^8$ is independently selected from hydrogen, $C_1$–$C_6$ alkyl, benzyl, 2,2,2-trifluoroethyl and aryl;

R$^9$ is independently selected from $C_1$–$C_6$ alkyl and aryl;

R$^{10}$ is selected from: H; R$^8$C(O)—; R$^9$S(O)$_m$—; unsubstituted or substituted $C_{1-4}$ alkyl, unsubstituted or substituted $C_{3-6}$ cycloalkyl, unsubstituted or substituted heterocycle, unsubstituted or substituted aryl, substituted aroyl, unsubstituted or substituted heteroaroyl, substituted arylsulfonyl, unsubstituted or substituted heteroarylsulfonyl, wherein the substituted group is substituted with one or two substituents selected from:
a) $C_{1-4}$ alkoxy,
b) aryl or heterocycle,
c) halogen, d) HO, e) 
$$\begin{array}{c}\phantom{x}\\ \diagup\!\!\diagdown R^9 \\ \| \\ O\end{array},$$

f)
$$\begin{array}{c}\phantom{x}\\ \diagup\!\!\diagdown OR^8 \\ \| \\ O\end{array},$$

g) —S(O)$_m$R$^9$, h) N(R$^8$)$_2$, or i) C$_{3-6}$ cycloalkyl;

A$^1$ and A$^2$ are independently selected from: a bond, —CH=CH—, —C≡C—, —C(O)—, —C(O)NR$^8$—, O, —N(R$^8$)—, or —S(O)$_m$;

J, K and L are independently selected from: S, N, O, NH and CH;

V is selected from:
  a) heterocycle selected from pyrrolidinyl, imidazolyl, pyridinyl, thiazolyl, indolyl, quinolinyl, isoquinolinyl, and thienyl, and
  b) aryl;

W is a heterocycle selected from pyrrolidinyl, triazolyl, imidazolyl, pyridinyl, thiazolyl, inclolyl, quinolinyl, or isoquinolinyl;

X is a bond, —S(O)$_m$—, O or —C(=O)—;

m is 0, 1 or 2;

n is 0, 1, 2, 3 or 4;

p is 1, 2 or 3;

q is 0, 1 or 2, provided that q is not 0 or 1 if X is O;

r is 0 to 5, previded that r is 0 when V is hydrogen;

s is 1 or 2;

t is 1; and u is independently 0 or 1;

or an optical isomer or a pharmaceutically acceptable salt thereof.

Another preferred embodiment of the compounds of this invention are illustrated by the formula B:

wherein:

R$^{1a}$ and R$^{1c}$ are independently selected from: hydrogen, C$_3$–C$_{10}$ cycloalkyl, R$^8$O—, —N(R$^8$)$_2$, F or C$_1$–C$_6$ alkyl;

R$^{1b}$ is independently selected from:
  a) hydrogen,
  b) aryl, heterocycle, C$_3$–C$_{10}$ cycloalkyl, R$^8$O—, —N(R$^8$)$_2$, F or C$_2$–C$_6$ alkenyl,
  c) unsubstituted or substituted C$_1$–C$_6$ alkyl wherein the substituent on the substituted C$_1$–C$_6$ alkyl is selected from unsubstituted or substituted aryl, heterocycle, C$_3$–C$_{10}$ cycloalkyl, C$_2$–C$_6$ alkenyl, R$^8$O— and —N(R$^8$)$_2$;

R$^{2a}$ and R$^{2b'}$ are independently selected from selected from:
  H; C$_1$–C$_6$ alkyl,
  $$\begin{array}{c}\diagup\!\!\diagdown NR^6R^7 \\ \| \\ O\end{array} \text{ or } \begin{array}{c}\diagup\!\!\diagdown OR^6 \\ \| \\ O\end{array};$$

R$^{3a}$ and R$^{3b}$ are independently selected from:
  a) hydrogen,
  b) unsubstituted or substituted aryl, unsubstituted or substituted heterocycle, unsubstituted or substituted C$_3$–C$_{10}$ cycloalkyl, unsubstituted or substituted C$_2$–C$_6$ alkenyl, C$_2$–C$_6$ alkynyl, halogen, C$_1$–C$_6$ perfluoroalkyl, R$^9$O—, R$^9$S(O)$_m$—, R$^8$C(O)NR$^8$—, (R$^8$)$_2$NC(O)—, R$^9$C(O)O—, R$^8{}_2$N—C(NR$^8$)—, CN, NO$_2$, R$^8$C(O)—, N$_3$, —N(R$^8$)$_2$, or R$^9$OC(O)NR$^8$—,
  c) unsubstituted C$_1$–C$_6$ alkyl,
  d) substituted C$_1$–C$_6$ alkyl wherein the substituent on the substituted C$_1$–C$_6$ alkyl is selected from unsubstituted or substituted aryl, unsubstituted or substituted heterocyclic, C$_3$–C$_{10}$ cycloalkyl, C$_2$–C$_6$ alkenyl, C$_2$–C$_6$ alkynyl, R$^9$O—, R$^9$S(O)$_m$—, R$^8$C(O)NR$^8$—, (R$^8$)$_2$NC(O)—, R$^8{}_2$N—C(NR$^8$)—, CN, R$^8$C(O)—, N$_3$, —N(R$^8$)$_2$, and R$^9$OC(O)—NR$^8$—;

R$^4$ is independently selected from:
  a) hydrogen,
  b) aryl, substituted aryl, heterocycle, substituted heterocycle, C$_1$–C$_6$ alkyl, C$_2$–C$_6$ alkenyl, C$_2$–C$_6$ alkynyl, C$_1$–C$_6$ perfluoroalkyl, F, Cl, R$^8$O—, R$^8$C(O)NR$^8$—, CN, NO$_2$, (R$^8$)$_2$N—C(NR$^8$)—, R$^8$C(O)—, —N(R$^8$)$_2$, or R$^9$OC(O)NR$^8$—, and
  c) C$_1$–C$_6$ alkyl substituted by C$_1$–C$_6$ perfluoroalkyl, R$^8$O—, R$^8$C(O)NR$^8$—, (R$^8$)$_2$N—C(NR$^8$)—, R$^8$C(O)—, —N(R$^8$)$_2$, or R$^9$OC(O)NR$^8$—;

R$^{5a}$ and R$^{5b}$ are independently hydrogen, C$_1$–C$_6$ alkyl, cyclopropyl, trifluoromethyl and halogen;

R$^6$ and R$^7$ are independently selected from:
  H; C$_{1-4}$ alkyl, C$_{3-6}$ cycloalkyl, aryl, heterocycle, unsubstituted or substituted with one or two:
  a) C$_{1-4}$ alkoxy,
  b) halogen, or
  c) substituted or unsubstituted aryl or substituted or unsubstituted heterocycle;

R$^8$ is independently selected from hydrogen, C$_1$–C$_6$ alkyl, 2,2,2-trifluoroethyl, benzyl and aryl;

R$^9$ is independently selected from C$_1$–C$_6$ alkyl and aryl;

A$^1$ and A$^2$ are independently selected from: a bond, —CH=CH—, —C≡C—, —C(O)—, —C(O)NR$^8$—, O, —N(R$^8$)—, or —S(O)$_m$;

J, K and L are independently selected from: S, N, O, NH and CH;

V is selected from:
a) hydrogen,
b) heterocycle selected from pyrrolidinyl, imidazolinyl, pyridinyl, thiazolyl, oxazolyl, indolyl, quinolinyl, isoquinolinyl, triazolyl and thienyl,
c) aryl,
d) $C_1$–$C_{20}$ alkyl wherein from 0 to 4 carbon atoms are replaced with a a heteroatom selected from O, S, and N, and
e) $C_2$–$C_{20}$ alkenyl, and provided that V is not hydrogen if $A^1$ is —$S(O)_m$ and V is not hydrogen if $A_1$ is a bond, n is 0 and $A^2$ is —$S(O)_m$;

X is a bond, —$S(O)_m$—, O or —$C(=O)$—;

m is 0, 1 or 2;

n is 0, 1, 2, 3 or 4;

p is 0, 1, 2, 3 or 4;

q is 0, 1 or 2, provided that q is not 0 or 1 if X is O;

r is 0 to 5, provided that r is 0 when V is hydrogen; and u is independently 0 or 1;

or an optical isomer or pharmaceutically acceptable salt thereof.

Another preferred embodiment of the compounds of this invention are illustrated by the formula C:

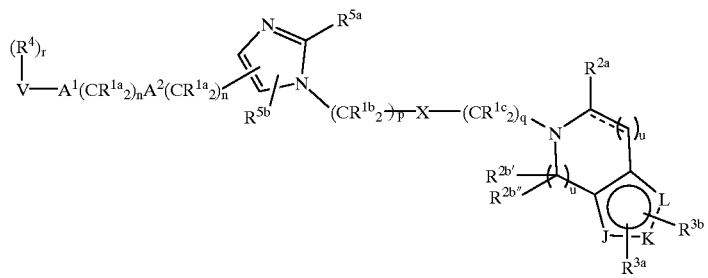

C wherein:
$R^{1a}$ and $R^{1c}$ are independently selected from: hydrogen, $C_3$–$C_{10}$ cycloalkyl, $R^8O$—, —$N(R^8)_2$, F or $C_1$–$C_6$ alkyl;

$R^{1b}$ is independently selected from:
a) hydrogen,
b) aryl, heterocycle, $C_3$–$C_{10}$ cycloalkyl, $R^8O$—, —$N(R^8)_2$, F or $C_2$–$C_6$ alkenyl,
c) unsubstituted or substituted $C_1$–$C_6$ alkyl wherein the substituent on the substituted $C_1$–$C_6$ alkyl is selected from unsubstituted or substituted aryl, heterocycle, $C_3$–$C_{10}$ cycloalkyl, $C_2$–$C_6$ alkenyl, $R^8O$—and —$N(R^8)_2$;

$R^{2a}$ and $R^{2b''}$ are independently selected from selected from:
H; $C_1$–$C_6$ alkyl,

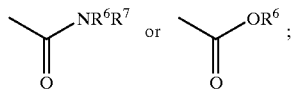

$R^{3a}$ and $R^{3b}$ are independently selected from:
a) hydrogen,
b) unsubstituted or substituted aryl, unsubstituted or substituted heterocycle, unsubstituted or substituted $C_3$–$C_{10}$ cycloalkyl, unsubstituted or substituted $C_2$–$C_6$ alkenyl, $C_2$–$C_6$ alkynyl, halogen, $C_1$–$C_6$ perfluoroalkyl, $R^9O$—, $R^9S(O)_m$—, $R^8C(O)NR^8$—, $(R^8)_2NC(O)$—, $R^9C(O)O$—, $R^8_2N$—$C(NR^8)$—, CN, $NO_2$, $R^8C(O)$—, $N_3$, —$N(R^8)_2$, or $R^9OC(O)NR^8$—,
c) unsubstituted $C_1$–$C_6$ alkyl,
d) substituted $C_1$–$C_6$ alkyl wherein the substituent on the substituted $C_1$–$C_6$ alkyl is selected from unsubstituted or substituted aryl, unsubstituted or substituted heterocyclic, $C_3$–$C_{10}$ cycloalkyl, $C_2$–$C_6$ alkenyl, $C_2$–$C_6$ alkynyl, $R^9O$—, $R^9S(O)_m$—, $R^8C(O)NR^8$—, $(R^8)_2NC(O)$—, $R^8_2N$—$C(NR^8)$—, CN, $R^8C(O)$—, $N_3$, —$N(R^8)_2$, and $R^9OC(O)$—$NR^8$—;

$R^4$ is independently selected from:
a) hydrogen,
b) aryl, substituted aryl, heterocycle, substituted heterocycle, $C_1$–$C_6$ alkyl, $C_2$–$C_6$ alkenyl, $C_2$–$C_6$ alkynyl, $C_1$–$C_6$ perfluoroalkyl, F, Cl, $R^8O$—, $R^8C(O)NR^8$—, CN, $NO_2$, $(R^8)_2N$—$C(NR^8)$—, $R^8C(O)$—, —$N(R^8)_2$, or $R^9OC(O)NR^8$—, and
c) $C_1$–$C_6$ alkyl substituted by $C_1$–$C_6$ perfluoroalkyl, $R^8O$—, $R^8C(O)NR^8$—, $(R^8)_2N$—$C(NR^8)$—, $R^8C(O)$—, —$N(R^8)_2$, or $R^9OC(O)NR^8$—;

$R^{5a}$ and $R^{5b}$ are independently hydrogen, $C_1$–$C_6$ alkyl, cyclopropyl, trifluoromethyl and halogen;

$R^6$ and $R^7$ are independently selected from:
H; $C_{1-4}$ alkyl, $C_{3-6}$ cycloalkyl, aryl, heterocycle, unsubstituted or substituted with one or two:
a) $C_{1-4}$ alkoxy,
b) halogen, or
c) substituted or unsubstituted aryl or substituted or unsubstituted heterocycle;

$R^8$ is independently selected from hydrogen, $C_1$–$C_6$ alkyl, 2,2,2-trifluoroetbyl, benzyl and aryl;

$R^9$ is independently selected from $C_1$–$C_6$ alkyl and aryl;

$A^1$ and $A^2$ are independently selected from: a bond, —CH=CH—, —C≡C—, —C(O)—, —C(O)NR^8—, O, —N(R^8)—, or —$S(O)_m$;

J, K and L are independently selected from: S, N, O, NH and CH;

V is selected from:
a) hydrogen,
b) heterocycle selected from pyrrolidinyl, imidazolinyl, pyridinyl, thiazolyl, oxazolyl, indolyl, quinolinyl, isoquinolinyl, triazolyl and thienyl,
c) aryl,
d) $C_1$–$C_{20}$ allcyl wherein from 0 to 4 carbon atoms are replaced with a a heteroatom selected from O, S, and N, and
e) $C_2$–$C_{20}$ alkenyl, and provided that V is not hydrogen if $A^1$ is —$S(O)_m$ and V is not hydrogen if $A^1$ is a bond, n is 0 and $A^2$ is —$S(O)_m$;

X is a bond, —$S(O)_m$—, O or —$C(=O)$—;

m is 0, 1 or 2;

n is 0, 1, 2, 3 or 4;

p is 0, 1, 2, 3 or 4, provided that p is not 0 if X is a bond or O;

q is 0, 1 or 2, provided that q is not 0 or 1 if X is O;

r is 0 to 5, provided that r is 0 when V is hydrogen; and u is independently 0 or 1;

or an optical isomer or pharmaceutically acceptable salt thereof.

In a more preferred embodiment of this invention, the inhibitors of farnesyl-protein transferase are illustrated by the formula D:

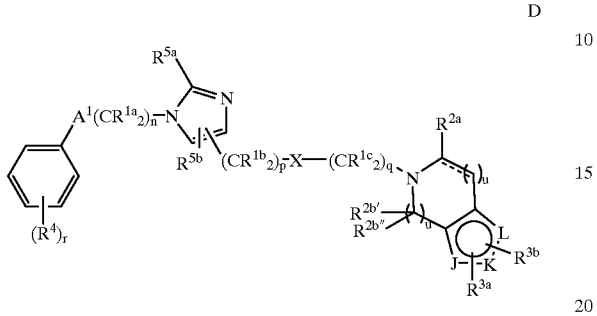

D wherein:
- $R^{1a}$ and $R^{1c}$ are independently selected from: hydrogen, $C_3$–$C_{10}$ cycloalkyl or $C_1$–$C_6$ alkyl
- $R^{1b}$ is independently selected from:
  a) hydrogen,
  b) aryl, heterocycle, $C_3$–$C_{10}$ cycloalkyl, $R^8O$—, —$N(R^8)_2$, F or $C_2$–$C_6$ alkenyl,
  c) $C_1$–$C_6$ alkyl unsubstituted or substituted by aryl, heterocycle, $C_3$–$C_{10}$ cycloalkyl, $C_2$–$C_6$ alkenyl, $R^8O$—, or —$N(R^8)_2$;
- $R^{2a}$ and $R^{2b'}$ are independently selected from selected from:
  H; $C_1$–$C_6$ alkyl,

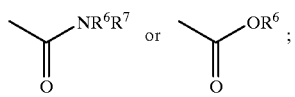

- $R^{3a}$ and $R^{3b}$ are independently selected from:
  a) hydrogen,
  b) unsubstituted or substituted aryl, unsubstituted or substituted heterocycle, unsubstituted or substituted $C_3$–$C_{10}$ cycloalkyl, unsubstituted or substituted $C_2$–$C_6$ alkenyl, $C_2$–$C_6$ alkynyl, halogen, $C_1$–$C_6$ perfluoroalkyl, $R^9O$—, $R^9S(O)_m$—, $R^8C(O)NR^8$—, $(R^8)_2NC(O)$—, $R^9C(O)O$—, $R^8_2N$—$C(NR^8)$—, CN, $NO_2$, $R^8C(O)$—, $N_3$, —$N(R^8)_2$, or $R^9OC(O)NR^8$—,
  c) unsubstituted $C_1$–$C_6$ alkyl,
  d) substituted $C_1$–$C_6$ alkyl wherein the substituent on the substituted $C_1$–$C_6$ alkyl is selected from unsubstituted or substituted aryl, unsubstituted or substituted heterocyclic, $C_3$–$C_{10}$ cycloalkyl, $C_2$–$C_6$ alkenyl, $C_2$–$C_6$ alkynyl, $R^9O$—, $R^9S(O)_m$—, $R^8C(O)NR^8$—, $(R^8)_2NC(O)$—, $R^8_2N$—$C(NR^8)$—, CN, $R^8C(O)$—, $N_3$, —$N(R^8)_2$, and $R^9OC(O)$—$NR^8$—;
- $R^4$ is independently selected from:
  a) hydrogen,
  b) aryl, substituted aryl, heterocycle, substituted heterocycle, $C_1$–$C_6$ alkyl, $C_2$–$C_6$ alkenyl, $C_2$–$C_6$ alkynyl, $C_1$–$C_6$ perfluoroalkyl, F, Cl, $R^8O$—, $R^8C(O)NR^8$—, CN, $NO_2$, $(R^8)_2N$—$C(NR^8)$—, $R^8C(O)$—, —$N(R^8)_2$, or $R^9OC(O)NR^8$—, and
  c) $C_1$–$C_6$ alkyl substituted by $C_1$–$C_6$ perfluoroalkyl, $R^8O$—, $R^8C(O)NR^8$—, $(R^8)_2N$—$C(NR^8)$—, $R^8C(O)$—, —$N(R^8)_2$, or $R^9OC(O)NR^8$—;
- $R^{5a}$ and $R^{5b}$ are independently hydrogen, ethyl, cyclopropyl or methyl;
- $R^6$ and $R^7$ are independently selected from:
  H; $C_{1-4}$ alkyl, $C_{3-6}$ cycloalkyl, aryl, heterocycle, unsubstituted or substituted with one or two:
  a) $C_{1-4}$ alkoxy,
  b) halogren, or
  c) substituted or unsubstituted aryl or substituted or unsubstituted heterocycle;
- $R^8$ is independently selected from hydrogen, $C_1$–$C_6$ alkyl, 2,2,2-trifluoroethyl, benzyl and aryl;
- $R^9$ is independently selected from $C_1$–$C_6$ alkyl and aryl;
- $A^1$ is selected from: a bond, —C(O)—, O, —$N(R^8)$—, or —$S(O)_m$—
- J, K and L are independently selected from: S, N, O, NH and CH;
- X is a bond, —$S(O)_m$—, O or —C(=O)—;
- n is 0, 1 or 2; provided that n is not 0 or 1 if $A^1$ is a bond, O, —$N(R^8)$—, or $S(O)_m$;
- m is 0, 1 or 2;
- p is 0, 1, 2, 3 or 4;
- q is 0, 1 or 2, provided that q is not 0 or 1 if X is O;
- r is 1 or 2; and
- u is independently 0 or 1;

or an optical isomer or pharmaceutically acceptable salt thereof.

In another more preferred embodiment of this invention, the inhibitors of farnesyl-protein transferase are illustrated by the formula E:

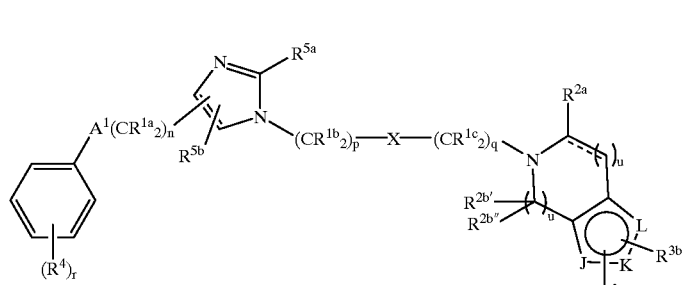

E wherein:
- $R^{1a}$ and $R^1c$ are independently selected from: hydrogen, $R^8O$—, —$N(R^8)_2$, F, $C_3$–$C_{10}$ cycloalkyl or $C_1$–$C_6$ alkyl;
- $R^{1b}$ is independently selected from:
  a) hydrogen,
  b) aryl, heterocycle, $C_3$–$C_{10}$ cycloalkyl, $R^8O$—, —$N(R^8)_2$, F or $C_2$–$C_6$ alkenyl, c) $C_1$–$C_6$ alkyl unsubstituted or substituted by aryl, heterocycle, $C_3$–$C_{10}$ cycloalkyl, $C_2$–$C_6$ alkenyl, $R^8O$—, or —$N(R^8)_2$;

$R^{2a}$ and $R^{2b'}$ are independently selected from selected from:
H; $C_1$–$C_6$ alkyl,

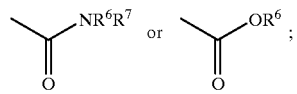

$R^{3a}$ and $R^{3b}$ are independently selected from:
a) hydrogen,
b) unsubstituted or substituted aryl, unsubstituted or substituted heterocycle, unsubstituted or substituted $C_3$–$C_{10}$ cycloalkyl, unsubstituted or substituted $C_2$–$C_6$ alkenyl, $C_2$–$C_6$ alkynyl, halogen, $C_1$–$C_6$ perfluoroalkyl, $R^9O$—, $R^9S(O)_m$—, $R^8C(O)NR^8$—, $(R^8)_2NC(O)$—, $R^9C(O)O$—, $R^8_2N$—$C(NR^8)$—, CN, NO_2, $R^8C(O)$—, $N_3$, —$N(R^8)_2$, or $R^9OC(O)NR^8$—,
c) unsubstituted $C_1$–$C_6$ alkyl,
d) substituted $C_1$–$C_6$ alkyl wherein the substituent on the substituted $C_1$–$C_6$ alkyl is selected from unsubstituted or substituted aryl, unsubstituted or substituted heterocyclic, $C_3$–$C_{10}$ cycloalkyl, $C_2$–$C_6$ alkenyl, $C_2$–$C_6$ alkynyl, $R^9O$—, $R^9S(O)_m$—, $R^8C(O)NR^8$—, $(R^8)_2NC(O)$—, $R^8_2N$—$C(NR^8)$—, CN, $R^8C(O)$—, $N_3$, —$N(R^8)_2$, and $R^9OC(O)$—$NR^8$—;

$R^4$ is independently selected from:
a) hydrogen,
b) aryl, substituted aryl, heterocycle, substituted heterocycle, $C_1$–$C_6$ alkyl, $C_2$–$C_6$ alkenyl, $C_2$–$C_6$ alkynyl, $C_1$–$C_6$ perfluoroalkyl, F, Cl, $R^8O$—, $R^8C(O)NR^8$—, CN, NO_2, $(R^8)_2N$—$C(NR^8)$—, $R^8C(O)$—, —$N(R^8)_2$, or $R^9OC(O)NR^8$—, and
c) $C_1$–$C_6$ alkyl substituted by $C_1$–$C_6$ perfluoroalkyl, $R^8O$—, $R^8C(O)NR^8$—, $(R^8)_2N$—$C(NR^8)$—, $R^8C(O)$—, —$N(R^8)_2$, or $R^9OC(O)NR^8$—;

$R^{5a}$ and $R^{5b}$ are independently hydrogen, ethyl, cyclopropyl or methyl;

$R^6$ and $R^7$ are independently selected from:
H; $C_{1-4}$ alkyl, $C_{3-6}$ cycloalkyl, aryl, heterocycle, unsubstituted or substituted with one or two:
a) $C_{1-4}$ alkoxy,
b) halogen, or
c) substituted or unsubstituted aryl or substituted or unsubstituted heterocycle;

$R^8$ is independently selected from hydrogen, $C_1$–$C_6$ alkyl, 2,2,2-trifluoroethyl, benzyl and aryl;

$R^9$ is independently selected from $C_1$–$C_6$ alkyl and aryl;

J, K and L are independently selected from: S, N, O, NH and CH;

X is a bond, —$S(O)_m$—, O or —$C(=O)$—;

n is 0 or 1;

m is 0, 1 or 2;

p is 0, 1, 2, 3 or 4, provided that p is not 0 if X is a bond or O;

q is 0, 1 or 2, provided that q is not 0 or 1 if X is O;

r is 1 or 2; and u is independently 0 or 1;

or an optical isomer or pharmaceutically acceptable salt thereof.

In a further embodiment of this invention, the inhibitors of farnesyl-protein transferase are illustrated by the formula F:

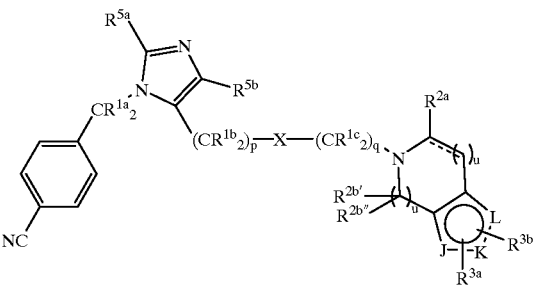

wherein:
$R^{1a}$ and $R^{1c}$ are independently selected from: hydrogen, $C_3$–$C_{10}$ cycloalkyl or $C_1$–$C_6$ alkyl;
$R^{1b}$ is independently selected from:
a) hydrogen,
b) aryl, heterocycle, $C_3$–$C_{10}$ cycloalkyl, $R^8O$—, —$N(R^8)_2$ or F,
c) $C_1$–$C_6$ alkyl unsubstituted or substituted by aryl, heterocycle, $C_3$–$C_{10}$ cycloalkyl, $R^8O$—, or —$N(R^8)_2$;

$R^{2a}$ and $R^{2b'}$ are independently selected from selected from: H; $C_1$–$C_6$ alkyl,

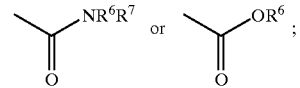

$R^{3a}$ and $R^{3b}$ are independently selected from:
a) hydrogen,
b) unsubstituted or substituted aryl, unsubstituted or substituted heterocycle, unsubstituted or substituted $C_3$–$C_{10}$ cycloalkyl, unsubstituted or substituted $C_2$–$C_6$ alkenyl, $C_2$–$C_6$ alkynyl, halogen, $C_1$–$C_6$ perfluoroalkyl, $R^9O$—, $R^9S(O)_m$—, $R^8C(O)NR^8$—, $(R^8)_2NC(O)$—, $R^9C(O)O$—, $R^8_2N$—$C(NR^8)$—, CN, NO_2, $R^8C(O)$—, $N_3$, —$N(R^8)_2$, or $R^9OC(O)NR^8$—,
c) unsubstituted $C_1$–$C_6$ alkyl,
d) substituled $C_1$–$C_6$ alkyl wherein the substituent on the substituLted $C_1$–$C_6$ alkyl is selected from unsubstituted or substituted aryl, unsubstituted or substituted heterocyclic, $C_3$–$C_{10}$ cycloalkyl, $C_2$–$C_6$ alkenyl, $C_2$–$C_6$ alkynyl, $R^9O$—, $R^9S(O)_m$—, $R^8C(O)NR^8$—, $(R^8)_2NC(O)$—, $R^8_2N$—$C(NR^8)$—, CN, $R^8C(O)$—, $N_3$, —$N(R^8)_2$, and $R^9OC(O)$—$NR^8$—;

$R^{5a}$ and $R^{5b}$ are independently hydrogen, ethyl, cyclopropyl or methyl;

$R^6$ and $R^7$ are independently selected from:
H; $C_{1-4}$ alkyl, $C_{3-6}$ cycloalkyl, aryl, heterocycle, unsubstituted or substituted with one or two:
a) $C_{1-4}$ alkoxy,
b) halogen, or
c) substituted or unsubstituted aryl or substituted or unsubstituted heterocycle;

$R^8$ is independently selected from hydrogen, $C_1$–$C_6$ alkyl, 2,2,2-trifluoroethyl, benzyl and aryl;

$R^9$ is independently selected from $C_1$–$C_6$ alkyl and aryl;

J, K and L are independently selected from: S, N, O, NH and CH;

X is a bond, —S(O)$_m$—, O or —C(=O)—;

m is 0, 1 or 2;

p is 0, 1, 2, 3 or 4;

q is 0, 1 or 2, provided that q is not 0 or 1 if X is O; and u is independently 0 or 1;

or an optical isomer or pharmaceutically acceptable salt thereof.

In a further embodiment of this invention, the inhibitors of farnesyl-protein transferase are illustrated by the formula G:

G wherein:

R$^{1a}$ and R$^{1c}$ are independently selected from: hydrogen, R$^8$O—, —N(R$^8$)$_2$, F, C$_3$–C$_{10}$ cycloalkyl or C$_1$–C$_6$ alkyl;

R$^{1b}$ is independently selected from:
  a) hydrogen,
  b) aryl, heterocycle or C$_3$–C$_{10}$ cycloalkyl,
  c) C$_1$–C$_6$ alkyl unsubstituted or substituted by aryl, heterocycle, C$_3$–C$_{10}$ cycloalkyl, C$_2$–C$_6$ alkenyl, R$^8$O—, or —N(R$^8$)$_2$;

R$^{2a}$ and R$^{2b'}$ are independently selected from selected from: H; C$_1$–C$_6$ alkyl, $$\text{(NR}^6\text{R}^7\text{ or OR}^6\text{ with C=O)}$$

R$^{3a}$ and R$^{3b}$ are independently selected from:
  a) hydrogen,
  b) unsubstituted or substituted aryl, unsubstituted or substituted heterocycle, unsubstituted or substituted C$_3$–C$_{10}$ cycloalkyl, unsubstituted or substituted C$_2$–C$_6$ alkenyl, C$_2$–C$_6$ alkynyl, halogen, C$_1$–C$_6$ perfluoroalkyl, R$^9$O—, R$^9$S(O)$_m$—, R$^8$C(O)NR$^8$—, (R$^8$)$_2$NC(O)—, R$^9$C(O)O—, R$^8_2$N—C(NR$^8$)—, CN, NO$_2$, R$^8$C(O)—, N$_3$, —N(R$^8$)$_2$, or R$^9$OC(O)NR$^8$—,
  c) unsubstituted C$_1$–C$_6$ alkyl,
  d) substituted C$_1$–C$_6$ alkyl wherein the substituent on the substituted C$_1$–C$_6$ alkyl is selected from unsubstituted or substituted aryl, unsubstituted or substituted heterocyclic, C$_3$–C$_{10}$ cycloalkyl, C$_2$–C$_6$ alkenyl, C$_2$–C$_6$ alkynyl, R$^9$O—, R$^9$S(O)$_m$—, R$^8$C(O)NR$^8$—, (R$^8$)$_2$NC(O)—, R$^8_2$N—C(NR$^8$)—, CN, R$^8$C(O)—, N$_3$, —N(R$^8$)$_2$, and R$^9$OC(O)—NR$^8$—;

R$^{5a}$ and R$^{5b}$ are independently hydrogen, ethyl, cyclopropyl or methyl;

R$^6$ and R$^7$ are independently selected from:
  H; C$_{1-4}$ alkyl, C$_{3-6}$ cycloalkyl, aryl, heterocycle, unsubstitulted or substituted with one or two:
  a) C$_{1-4}$ alkoxy,
  b) halogen, or
  c) substituted or unsubstituted aryl or substituted or unsubstituted heterocycle;

R$^8$ is independently selected from hydrogen, C$_1$–C$_6$ alkyl, 2,2,2-trifluoroethyl, benzyl and aryl;

R$^9$ is independently selected from C$_1$–C$_6$ alkyl and aryl;

J, K and L are independently selected from: S, N, O, NH and CH;

A$^1$ is selected from: a bond, —C(O)—, O, —N(R$^8$)—, or —S(O)$_m$;

X is a bond, —S(O)$_m$—, O or —C(=O)—;

m is 0, 1 or 2;

n is 0, 1 or 2:, provided that n is not 0 if A$^1$ is a bond, O, —N(R$^8$)—, or S(O)$_m$;

p is 1, 2 or 3;

q is 0, 1 or 2, provided that q is not 0 or 1 if X is O; and u is independently 0 or 1;

or an optical isomer or pharmaceutically acceptable salt thereof.

The preferred compounds of this invention are as follows:

5-(1-(4-Cyanobenzyl)-5-imidazolylmethyl)-4,5,6,7-tetrahydrothieno[3,2-c]pyridine 2-Bromo-5-(1-(4-cyanobenzyl)-5-imidazolylmethyl)-4,5,6,7-tetrahydrothieno[3,2-c]pyridine 2-Phenyl-5-(1-(4-cyanobenzyl)-5-imidazolylmethyl)-4,5,6,7-tetrahydrothieno[3,2-c]pyridine

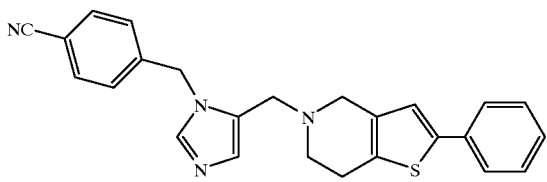

5-[5-(5-Azabenzimidazolyl)methyl)-1-(4-cyanobenzyl) imidazole

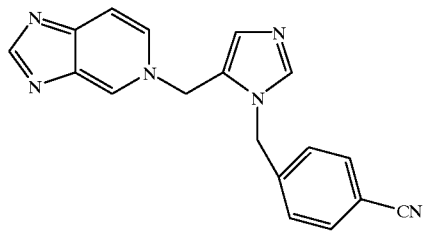

5-[4-(4-Azabenzimidazolyl)methyl)-1-(4-cyanobenzyl) imidazole

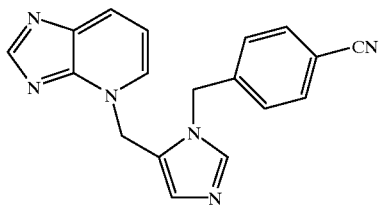

or a pharmaceutically acceptable salt thereof.

The compounds of the present invention may have asymmetric centers and occur as racemates, racemic mixtures, and as individual diastereomers, with all possible isomers, including optical isomers, being included in the present invention. When any variable (e.g. aryl, heterocycle, $R^{1a}$, $R^4$ etc.) occurs more than one time in any constituent, its definition on each occurence is independent at every other occurence. Also, combinations of substituents/or variables are permissible only if such combinations result in stable compounds.

As used herein, "alkyl" is intended to include both branched and straight-chain saturated aliphatic hydrocarbon groups having the specified number of carbon atoms; "alkoxy" represents an alkyl group of indicated number of carbon atoms attached through an oxygen bridge. "Halogen" or "halo" as used herein means fluoro, chloro, bromo and iodo.

As used herein, "aryl" is intended to mean any stable monocyclic, bicyclic or tricyclic carbon ring of up to 7 members in each ring, wherein at least one ring is aromatic. Examples of monocyclic and bicyclic aryl elements include phenyl, naphthyl, tetrahydronaphthyl, indanyl, biphenyl, phenanthryl, anthryl or acenaphthyl. Examples of tricyclic aryl elements include 10,11-dihydro-5H-dibenzo[a,d] cyclohepten-5-yl (which is also known as dibenzylsuberyl), 9-fluorenyl and 9,10-dihydroanthracen-9-yl. Preferably, "aryl" is a monocyclic or bicyclic carbon ring.

The term heterocycle or heterocyclic, as used herein, represents a stable 5- to 7-membered monocyclic or stable 8- to 11-membered bicyclic heterocyclic ring or stable 13- to 15-membered tricyclic heterocyclic ring, which is either saturated or unsaturated, and which consists of carbon atoms and from one to four heteroatoms selected from the group consisting of N, O, and S, and including any bicyclic group in which any of the above-defined heterocyclic rings is fused to a benzene ring. The heterocyclic ring may be attached at any heteroatom or carbon atom which results in the creation of a stable structure. Examples of monocyclic and bicyclic heterocyclic elements include, but are not limited to, azepinyl, benzimidazolyl, benzisoxazolyl, benzofurazanyl, benzopyranyl, benzothiopyranyl, benzofuryl, benzothiazolyl, benzothienyl, benzoxazolyl, chromanyl, cinnolinyl, dihydrobenzofuryl, dihydrobenzothienyl, dihydrobenzothiopyranyl, dihydrobenzothiopyranyl sulfone, furyl, imidazolidinyl, imidazolinyl, imidazolyl, indolinyl, indolyl, isochromanyl, isoindolinyl, isoquinolinyl, isothiazolidinyl, isothiazolyl, isothiazolidinyl, morpholinyl, naphthyridinyl, oxadiazolyl, 2-oxoazepinyl, 2-oxopyrrolidinyl, pyridyl, pyrazinyl, pyrazolidinyl, pyrazolyl, pyridazinyl, pyrimidinyl, pyrrolidinyl, pyrrolyl, quinazolinyl, quinolinyl, quinoxalinyl, tetrahydrofuryl, tetrahydroisoquinolinyl, tetrahydroquinolinyl, thiamorpholinyl, thiamorpholinyl sulfoxide, thiazolyl, thiazolinyl, thienofuryl, thienothienyl, and thienyl. Examples of tricyclic heterocyclic elements include, but are not limited to, 6,11-dihydro-5H-benzo[5,6]cyclohepta[1,2-b]pyridine, 9,10-dihydro- 4H-3-thiabenzo[f]azulen-4-yl and 9-xanthenyl. The 6,11-dihydro-5H-benzo[5,6]cyclohepta[1, 2-b]pyridine moiety has the following structure:

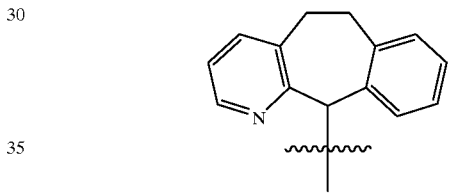

Preferably, "heterocyclic" is a monocyclic or bicyclic moiety.

As used herein, "heteroaryl" is intended to mean any stable monocyclic, bicyclic or tricyclic carbon ring of up to 7 members in each ring, wherein at least one ring is aromatic and wherein from one to four carbon atoms are replaced by heteroatoms selected from the group consisting of N, O, and S. Examples of monocyclic and bicyclic heteroaryl elements include, but are not limited to, benzimidazolyl, benzisoxazolyl, benzofurazanyl, benzopyranyl, benzothiopyranyl, benzofuryl, benzothiazolyl, benzothienyl, benzoxazolyl, chromanyl, cinnolinyl, dihydrobenzofuryl, dihydrobenzothienyl, dihydrobenzothiopyranyl, dihydrobenzothiopyranyl sulfone, furyl, imidazolyl, indolinyl, indolyl, isochromanyl, isoindolinyl, isoquinolinyl, isothiazolyl, naphthyridinyl, oxadiazolyl, pyridyl, pyrazinyl, pyrazolyl, pyridazinyl, pyrimidinyl, pyrrolyl, quinazolinyl, quinolinyl, quinoxalinyl, tetrahydroisoquinolinyl, tetrahydroquinolinyl, thiazolyl, thienofuryl, thienothienyl, and thienyl. Examples of tricyclic heteroaryl elements include, but are not limited to, 6,11-dihydro-5H-benzo[5,6] cyclohepta[1,2-b]pyridine. Preferably, "heteroaryl" is a monocyclic or bicyclic moiety.

As used herein, the terms "substituted aryl", "substituted heterocycle" and "substituted cycloalkyl" are intended to include the cyclic group containing from 1 to 3 substitutents in addition to the point of attachment to the rest of the compound. Such substitutents are preferably selected from the group which includes but is not limited to F, Cl, Br, $CF_3$, NH$_2$, N(C$_1$–C$_6$ alkyl)$_2$, NO$_2$, CN, (C$_1$–C$_6$ alkyl)O—, —OH, (C$_1$–C$_6$ alkyl)S(O)$_m$—, (C$_1$–C$_6$ alkyl)C(O)NH—, H$_2$N—C(NH)—, (C$_1$–C$_6$ alkyl)C(O)—, (C$_1$–C$_6$ alkyl)OC(O)—, N$_3$, (C$_1$–C$_6$ alkyl)OC(O)NH— and C$_1$–C$_{20}$ alkyl.

When R$^6$ and R$^7$ are combined to form a ring, cyclic amine moieties are formed. Examples of such cyclic moieties include, but are not limited to:

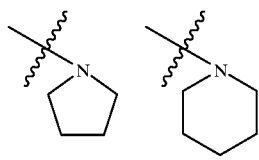

In addition, such cyclic moieties may optionally include another heteroatom(s). Examples of such heteroatom-containing cyclic amine moieties include, but are not limited to:

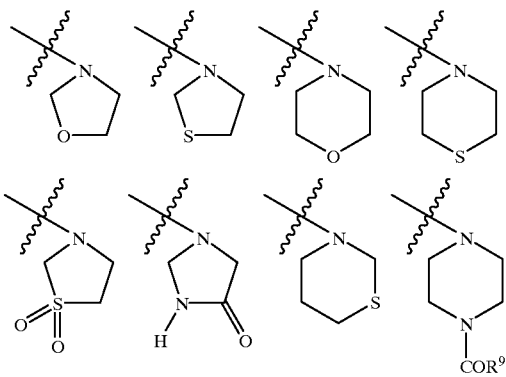

The variable J, K and L are selected such that the 5-member ring comprising them is aromatic in nature. Examples of the following ring system

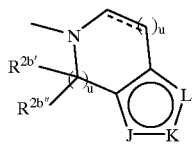

include, but are not limited to:

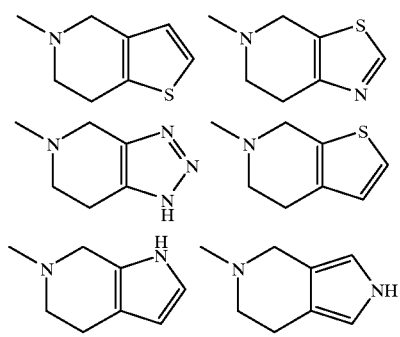

-continued

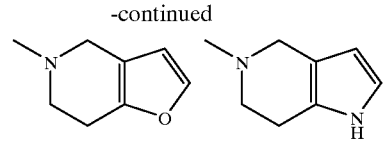
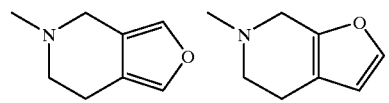
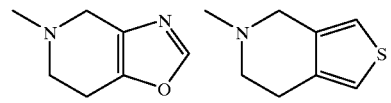
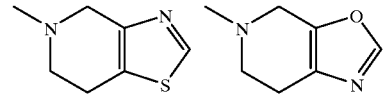
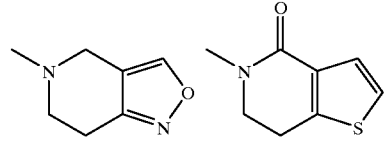
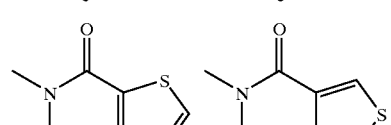
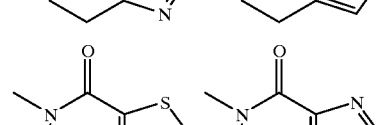
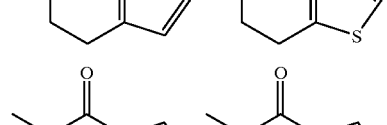
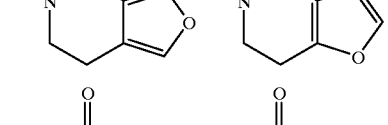
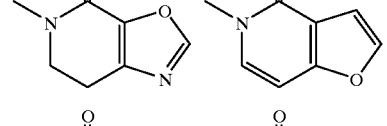
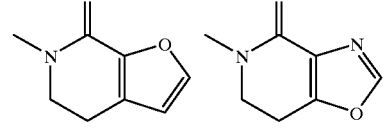
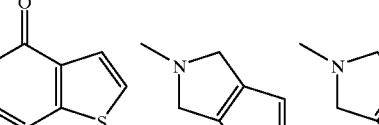
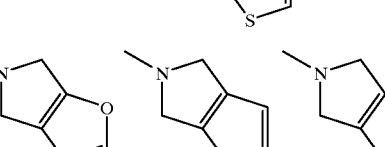

Preferably the ring system is selected from:

Examples of the following ring system include, but are not limited to:

Lines drawn into the ring systems from substituents (such as from $R^{3a}$, $R^{3b}$, $R^4$ etc.) indicate that the indicated bond may be attached to any of the substitutable ring carbon or nitrogen atoms.

Preferably, $R^{1a}$ and $R^{1b}$ are independently selected from: hydrogen, —N(R$^8$)$_2$, R$^8$C(O)NR$^8$— or C$_1$–C$_6$ alkyl which is unsubstituted or substituted by —N(R$^8$)$_2$, R$^8$O— or R$^8$C(O)NR$^8$—.

Preferably, $R^{2a}$ is selected from: H;

$$\text{—C(O)NR}^6\text{R}^7 \quad \text{or} \quad \text{—C(O)OR}^6.$$

Preferably, $R^{2b'}$ and $R^{2b''}$ are independently selected from selected from: H or C$_1$–C$_6$ alkyl.

Preferably, $R^{3a}$ and $R^{3b}$ are independently selected from: hydrogen, C$_1$–C$_6$ perfluoroalkyl, F, Cl, Br, R$^8$O—, R$^9$S(O)$_m$—, CN, R$^8$C(O)—, —N(R$^8$)$_2$ and C$_1$–C$_6$ alkyl.

Preferably, $R^4$ is selected from: hydrogen, perfluoroalkyl, F, Cl, Br, R$^8$O—, R$^9$S(O)$_m$—, CN, NO$_2$, R$^8_2$N—C(NR$^8$)—, R$^8$C(O)—, N$_3$, —N(R$^8$)$_2$, R$^9$OC(O)NR$^8$— and C$_1$–C$_6$ alkyl.

Preferably, $R^5$ is hydrogen or C$_1$–C$_6$ alkyl.

Preferably, $R^8$ is selected from H, C$_1$–C$_6$ alkyl and benzyl.

Preferably, $A^1$ and $A^2$ are independently selected from: a bond, —C(O)NR$^8$—, —NR$^8$C(O)—, O, —N(R$^8$)—, —S(O)$_2$N(R$^8$)— and —N(R$^8$)S(O)$_2$—.

Preferably, V is selected from hydrogen, heterocycle and aryl.

Preferably, W is imidazolyl.

Preferably, X is a bond or (C=O)—.

Preferably, n, p and r are independently 0, 1, or 2. More preferably, r is 1.

Preferably t is 1.

Preferably u is independently 0 or 1. Most preferably, u is 1.

Preferably, the moiety is selected from:

The pharmaceutically acceptable salts of the compounds of this invention include the conventional non-toxic salts of the compounds of this invention as formed, e.g., from non-toxic inorganic or organic acids. For example, such conventional non-toxic salts include those derived from inorganic acids such as hydrochloric, hydrobromic, sulfuric, sulfamic, phosphoric, nitric and the like: and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfinilic, 2-acetoxy-benzoic, fumaric, toluenesulfonic, methanesulfonic, ethane disulfonic, oxalic, isethionic, trifluoroacetic and the like.

It is intended that the definition of any substituent or variable (e.g., $R^{1a}$, Z, n, etc.) at a particular location in a molecule be independent of its dLefinitions elsewhere in that molecule. Thus, $-N(R^8)_2$ represents $-NH_2$, $-NHCH_3$, $-NHC_2H_5$, etc. It is understood that substituents and substitution patterns on the compounds of the instant invention can be selected by one of ordinary skill in the art to provide compounds that are chemically stable and that can be readily synthesized by techniques known in the art, as well as those methods set forth below, from readily available starting materials.

The pharmaceutically acceptable salts of the compounds of this invention can be synthesized from the compounds of this invention which contain a basic moiety by conventional chemical methods. Generally, the salts are prepared either by ion exchange chromatography or by reacting the free base with stoichiometric amounts or with an excess of the desired salt-forming inorganic or organic acid in a suitable solvent or various combinations of solvents.

Abbreviations used in the description of the chemistry and in the Examples that follow are:

| | |
|---|---|
| $Ac_2O$ | Acetic anhydride; |
| Boc | t-Butoxycarbonyl; |
| CBz | Carbobenzyloxy; |
| DBU | 1,8-diazabicyclo[5.4.0]undec-7-ene; |
| DMAP | 4-Dimethylaminopyridine; |
| DME | 1,2-Dimethoxyethane; |
| DMF | Dimethylformamide; |
| EDC | 1-(3-dimethylaminopropyl)-3-ethyl-carbodiimide-hydrochloride; |
| $Et_3N$ | Triethylamine; |
| EtOAc | Ethyl acetate; |
| FAB | Fast atom bombardment; |
| HOBT | 1-Hydroxybenzotriazole hydrate; |
| HOOBT | 3-Hydroxy-1,2,2-benzotriazin-4(3H-one; |
| HPLC | High-performance liquid chromatography; |
| MCPBA | m-Chloroperoxybenzoic acid; |
| MsCl | Methanesulfonyl chloride; |
| NaHMDS | Sodium bis(trimethylsilyl)amide; |
| Py | Pyridine; |
| TFA | Trifluoroacetic acid; |
| THF | Tetrahydrofuran. |

The compounds of this invention are prepared by employing reactions as shown in the Schemes 1–16, in addition to other standard manipulations such as ester hydrolysis, cleavage of protecting groups, etc., as may be known in the literature or exemplified in the experimental procedures. While stereochemistry is shown in the Schemes, a person of ordinary skill in the art would understand that the illustrated compounds represent racemic mixtures which may be separated at a subsequent purification step or may be utilized as the racemic mixture.

These reactions may be employed in a linear sequence to provide the compound of the invention or they may be used to synthesize fragments which are subsequently joined by the reductive alkylation or acylation reactions described in the Schemes.

Synopsis of Schemes 1–7:

The requisite intermediates are in some cases commercially available, or can be prepared according to literature procedures, for the most part. For example, see M. Cain et al., *Heterocycles*, 19:1003 (1982), J. W. Skiles et al., *J. Med. Chem.*, 29:784 (1986) and J. L. Stanton et al., *J. Med. Chem.*, 26:1267 (1983).

In Schemes 1–2, for example, the syntheses of several fused ring intermediates are outlined. The subsequent reactions described in the remaining schemes may be similarly applied to suitably protected commercially available tetrahydroisoquinolines, as well as commercially or synthetically obtained homologs, to provide compounds of the instant invention.

Scheme 1 describes the synthesis of 4,5,6,7-tetrahydrothieno[3,2-c]pyridines essentially according to the method of Halczenko and Hartman in *Synthetic Commun.*, 1996, 26, 1363. The nitrile 1 may be reduced to the amine 2 using, for example, Raney Nickel and this compound undergoes cyclization to 3 when heated with formaldehyde followed by hydrochloric acid treatment. Intermediate 3 may then be functionalized as described in subsequent schemes. The regioisomeric thienopyridine 4 is known (Gronowitz, *Ark. Kemi.*; 1970, 32, 217) and may undergo the same reactions as are described for 3.

Synthesis of the lower homolog of 3 is shown in Scheme 2. Using a modification of the chemistry described in U.S. Pat. No. 5,334,596, the commercially available 2,3-thiophenedicarboxylic acid anhydride may be heated with an amine to yield 5. Reduction of the carbonyls using, for example, diborane in a solvent such as THF would yield analogs such as 6. Further derivatives could be prepared by first deprotecting a suitably functionalized 6.

The furano analogs 7 (Scheme 2a) are described in the literature (Arnoldi et al, *J. Heterocyclic Chem.*, 1990, 27, 1169). Deprotection using, for example, aqueous HCl will produce 8 which may undergo reactions as described hereinbelow.

Scheme 3 illustrates reactions wherein the preferred 4-cyanobenzylimidazolyl moiety is incorporated into the instant compounds, either by reductive alkylation with the aldehyde 9 or an amide forming reaction with the acid 10.

Schemes 4–5 illustrate the syntheses of 4,5,6,7-tetrahydrothieno[3,2-c]pyridine of the instant invention wherein the "X" moiety is other than an alkyl bridge. The reactions illustrated therein show the incorporation of sidechains which comprise the preferred 4-cyanobenzylimidazolyl moiety. It is understood that a person of ordinary skill in the art could readily modify such reaction sequences by using appropriate protecting groups and reagents well known to one skilled in the art to provide other compounds of the instant invention.

Scheme 4 illustrates the syntheses of compounds of the instant invention wherein "X" is —S—. Thus the intermediate aldehyde 11 is reduced to the alcohol 12, activated and treated with a suitable thioacetate to provide the thioester 13. The thiol is then generated and alkylated with a suitable ester containing reagent, such as bromoacetic acid to provide intermediate 14. Reduction of the ester moiety, followed by oxidation provides the corresponding aldehyde, which can be utilized to reductively alkylate the suitably substituted 4,5,6,7-tetrahydrothieno[3,2-c]pyridine, for example, to provide the instant compound 15.

Scheme 5 illustrates the syntheses of compounds of the instant invention wherein "X" is —O—. Thus, a dihydroxyalkane, such as ethylene glycol, can be selectively protected and oxidized to provide the aldehyde 16. Intermediate 16 can be utilized to reductively alkylate the suitably substituted of 4,5,6,7-tetrahydro-thieno[3,2-c]pyridine, the sidechain deprotected and converted to the chloride 17. Intermediate 17 can then be alkylated with a suitable reagent to provide the instant compound 18 which incorporates the ether moiety.

The reagent utilized in the reductive alkylation of the of 4,5,6,7-tetrahydrothieno[3,2-c]pyridine may alternatively incorporate a leaving group which may subsequently react with a blocked imidazolyl reagent, such as 19 to provide compounds of the instant invention wherein "X" is a bond and the preferred imidazolyl is attached to the alkyl bridge via one of the ring nitrogens, as shown in Scheme 6.

Scheme 7 illustrates the syntheses of compounds of the instant invention comprising 3,4-dihydro-1(1H)-thieno[3,2-c]pyridones and a homologous [3.3.0] ring system.

SCHEME 1
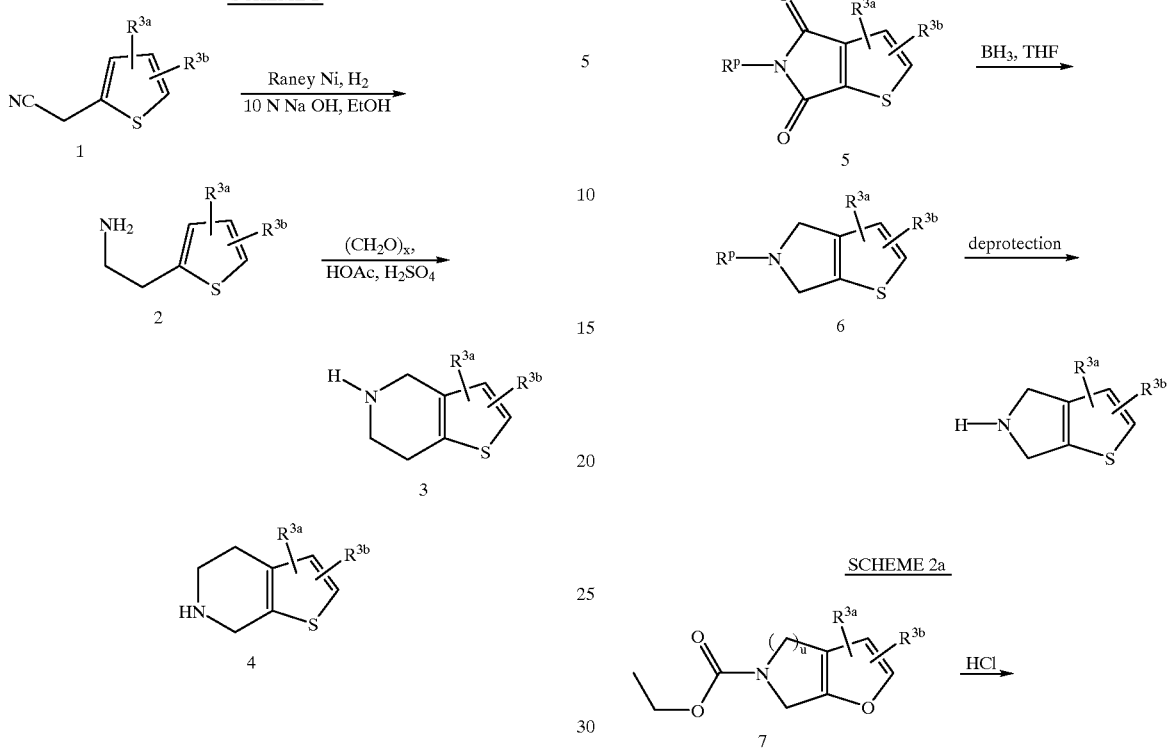
SCHEME 2
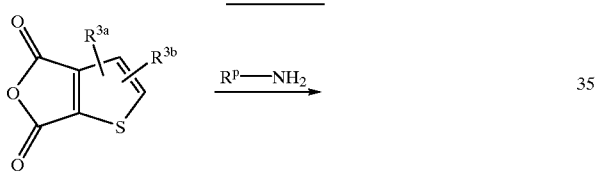
SCHEME 3
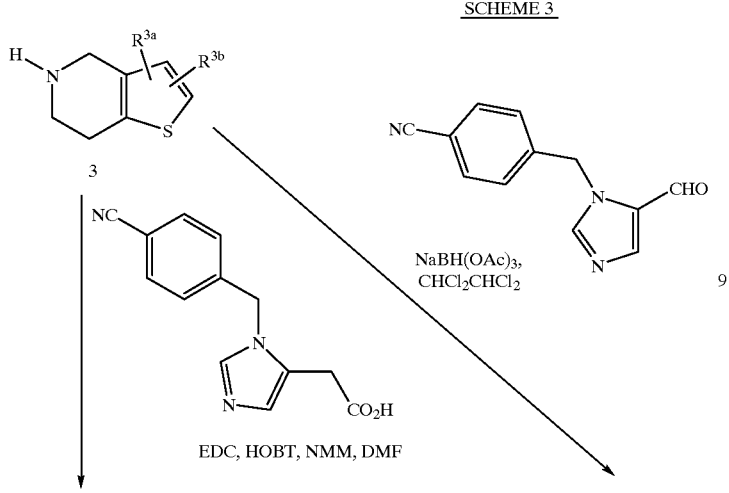

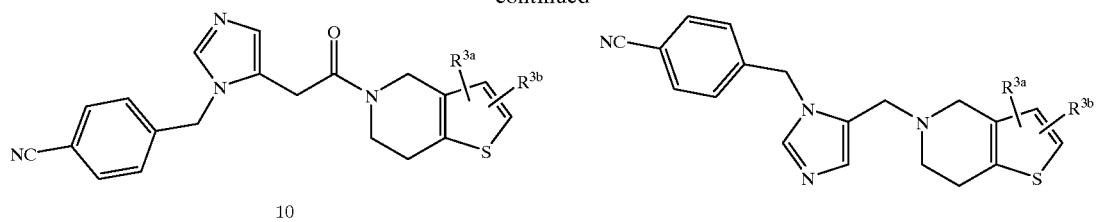
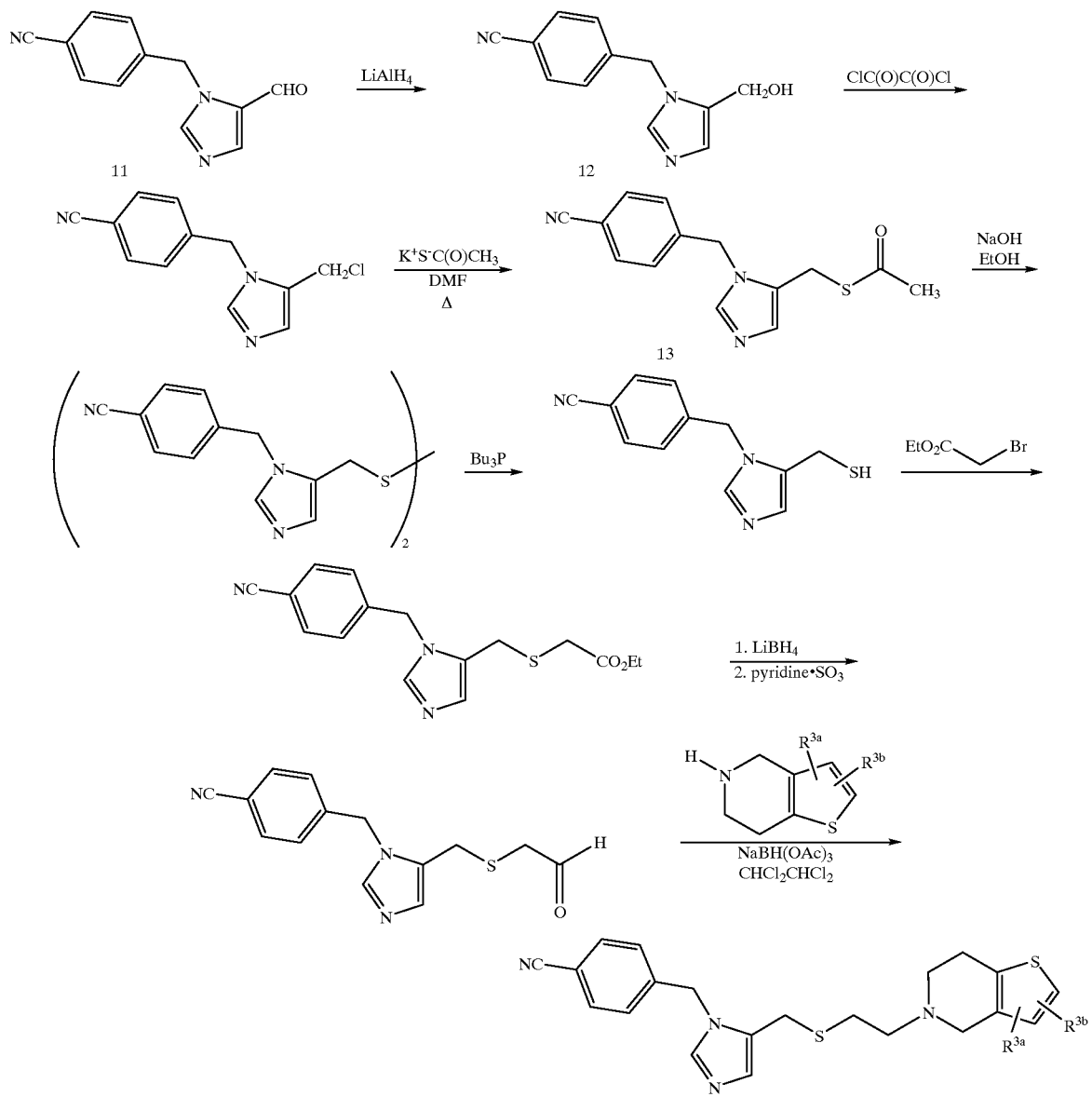
SCHEME 4

SCHEME 5

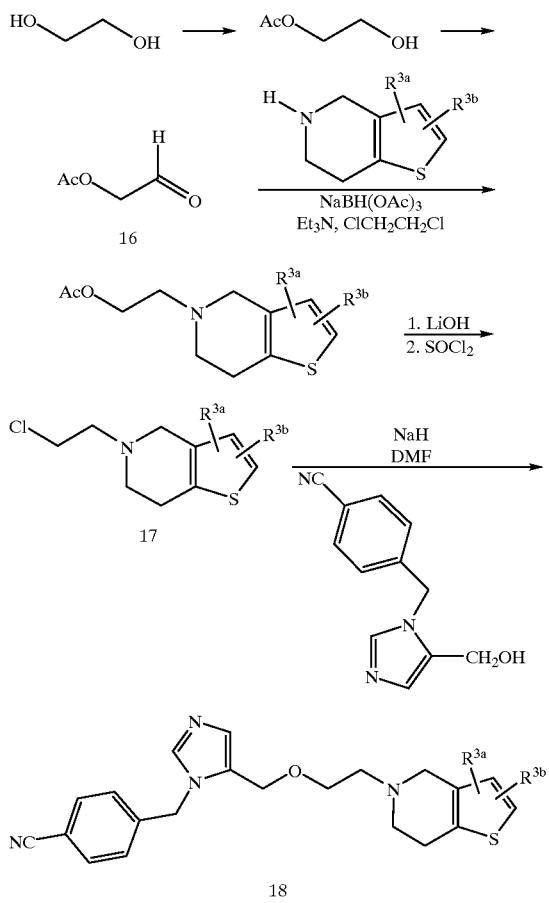

SCHEME 6

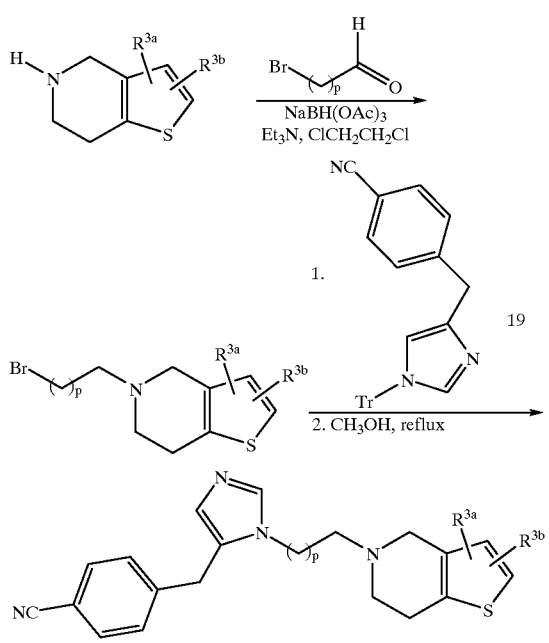

SCHEME 7

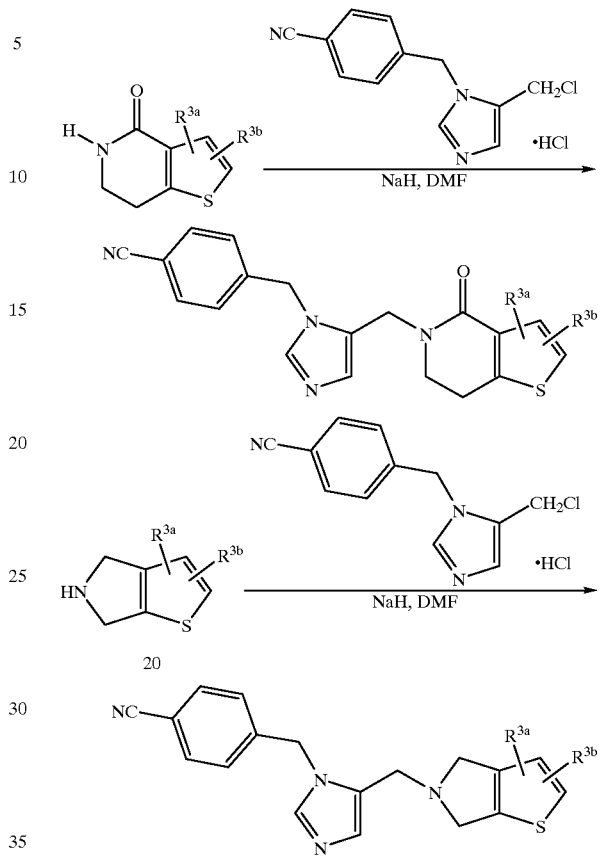

It is understood that while Schemes 8–16 illustrate preparation of both protected and unprotected intermediates, a person of ordinary skill would appreciate that subsequent reactions which utilize those intermediates, such as those described in Schemes 1–7, may require protection and eventual deprotection of certain intermediate moieties.

The selectively protected intermediate 20 utilized in the synthesis illustrated in Scheme 8 can be reductively alkylated with a variety of aldehydes, such as 21. The aldehydes can be prepared by standard procedures, such as that described by O. P. Goel, U. Krolls, M. Stier and S. Kesten in *Organic Syntheses*, 1988, 67, 69–75. The reductive alkylation can be accomplished at pH 5–7 with a variety of reducing agents, such as sodium triacetoxyborohydride or sodium cyanoborohydride in a solvent such as dichloroethane, methanol or dimethylformamide. The ester product 22 can be deprotected with trifluoroacetic acid in methylene chloride to give the substituted diamine 23. That diamine may be isolated in the salt form, for example, as a trifluoroacetate, hydrochloride or acetate salt, among others. The product diamine 23 can be further selectively protected and reductively alkylated with a second aldehyde to obtain an analogous tertiary amine. Alternatively, the diamine 23 can be cyclized to obtain intermediates such as the dihydroimidazole 24 by procedures known in the literature. The ester 24 can then be utilized in a reaction such as illustrated in Scheme 3 hereinabove.

Scheme 9 illustrates a general preparation of aralkyl imidazolyl intermediates 31 that can be utilized in reactions such as illustrated in Scheme 3. Thus imidazole acetic acid 27 can be converted to the protected acetate 29 by standard procedures, and 29 can be first reacted with an alkyl halide, then treated with refluxing methanol to provide the regiospecifically alkylated imidazole acetic acid ester 30. Hydrolysis provides the acetic acid 31.

Schemes 10–13 illustrate syntheses of suitably substituted alkanols useful in the syntheses of the instant compounds wherein the variable W is present as a pyridyl moiety. The hydroxyl moiety of such intermediates may be converted into the corresponding aldehyde, as illustrated in Scheme 10 or may be converted to a suitable leaving group, as illustrated in Scheme 12. Similar synthetic strategies for preparing alkanols that incorporate other heterocyclic moieties for variable W are also well known in the art.

Compounds of the instant invention wherein the $A^1$ $(CR^{1a}_2)_nA^2(CR^{1a}_2)_n$ linker is a substituted methylene may be synthesized by the methods shown in Scheme 14. Thus, the N-protected imidazolyl iodide 32 is reacted, under Grignard conditions with a suitably protected benzaldehyde to provide the alcohol 33. Acylation. followed by the alkylation procedure illustrated in the Schemes above (in particular, Scheme 6) provides the instant compound 34. If other $R^{1a}$ substituents are desired, the acetyl moiety can be manipulated as illustrated in the Scheme.

Scheme 15 illustrates synthesis of an instant compound wherein a non-hydrogen $R^{5b}$ is incorporated in the instant compound. Thus, a readily available 4-substituted imidazole 37 may be selectively iodinated to provide the 5-iodoimidazole 38. That imidazole may then be protected and coupled to a suitably substituted benzyl moiety to provide intermediate 39. Intermediate 39 can then undergo the alkylation reactions that were described hereinabove.

Compounds of the instant invention wherein the $A^1(CR^{1a}_2)_nA^2(CR^{1a}_2)_n$ linker is oxygen may be synthesized by methods known in the art, for example as shown in Scheme 16. The suitably substituted phenol 41 may be reacted with methyl N-(cyano)methanimidate to provide the 4-phenoxyimidazole 42. After selective protection of one of the imidazolyl nitrogens, the intermediate 43 can undergo alkylation reactions as described for the benzylimidazoles hereinabove.

SCHEME 8

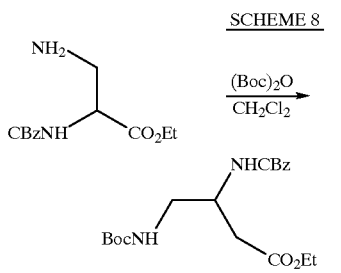

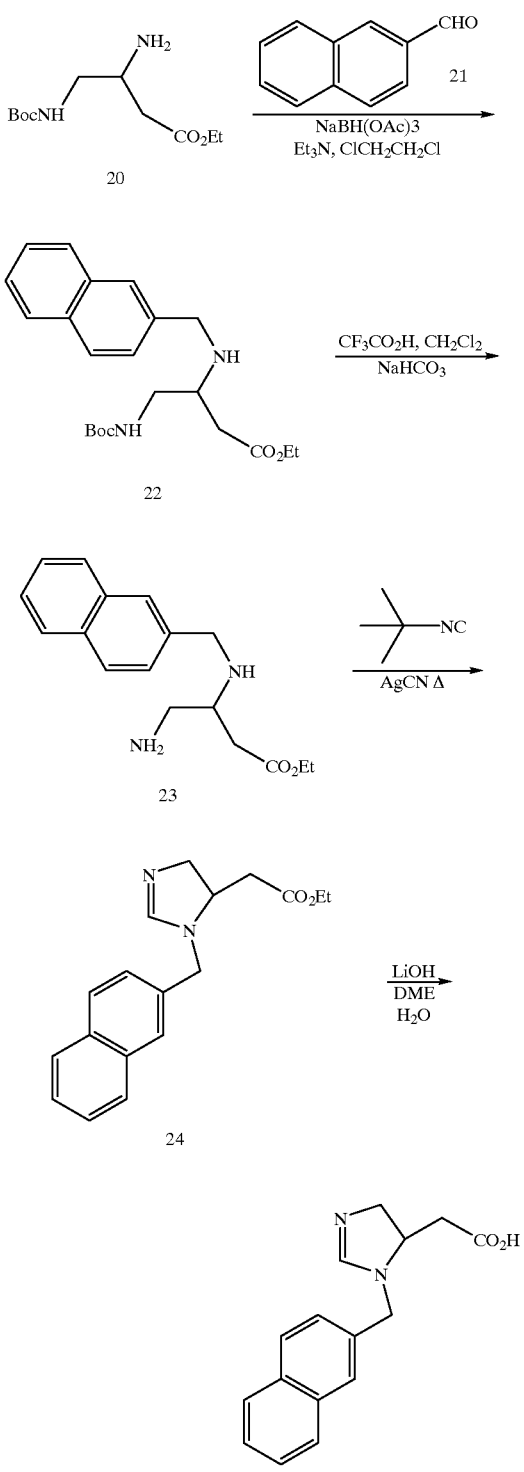

SCHEME 9
SCHEME 10
SCHEME 11
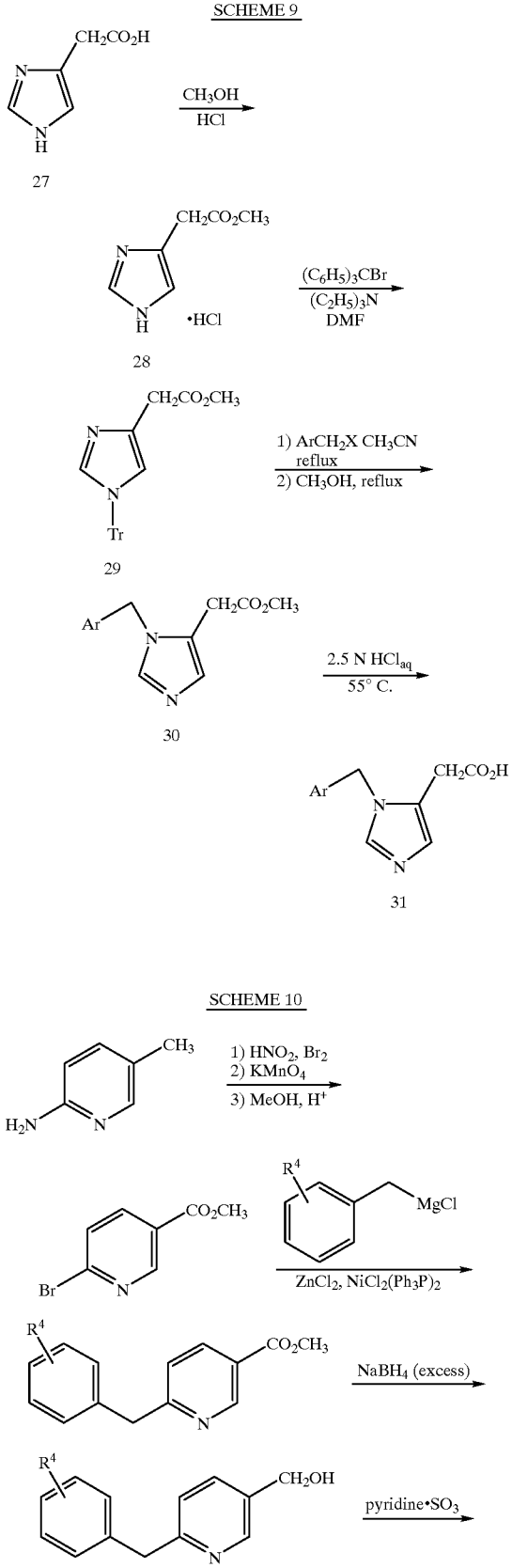
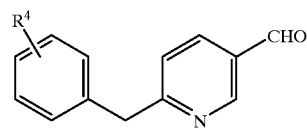

SCHEME 12
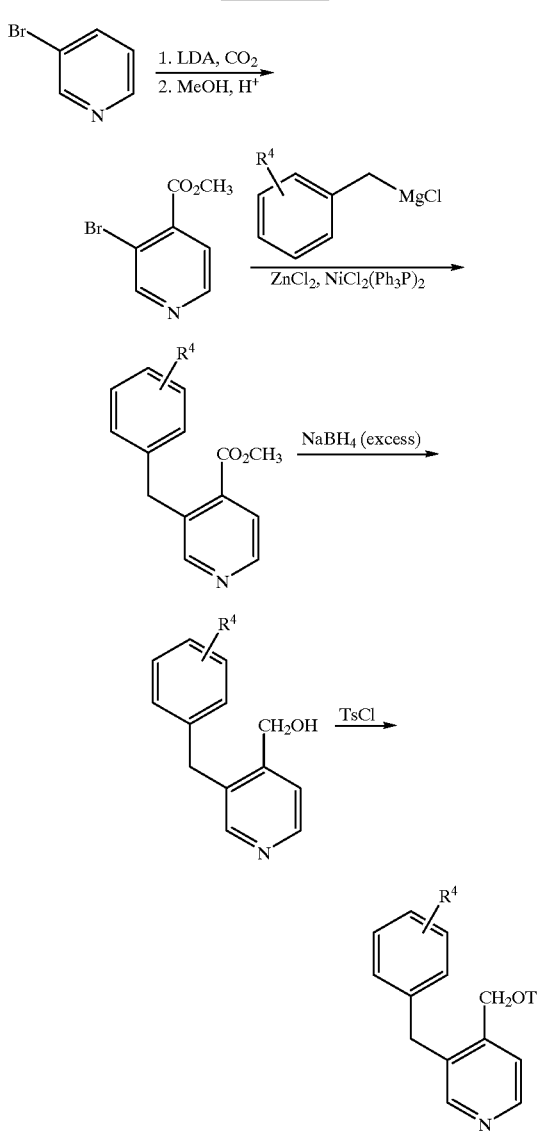
SCHEME 13
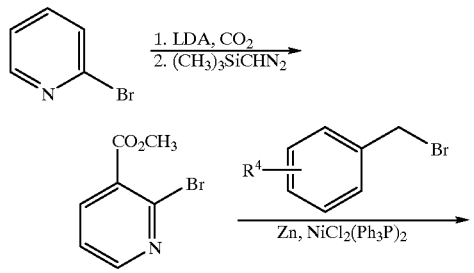
SCHEME 14
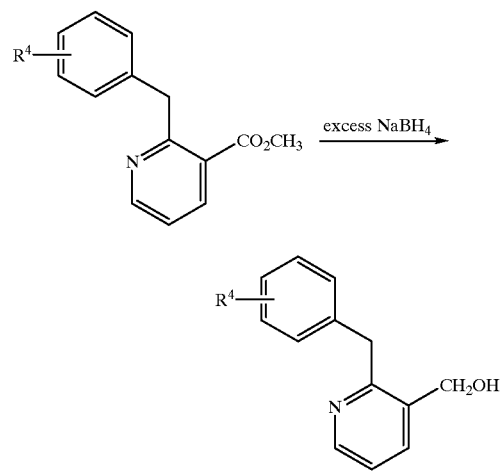
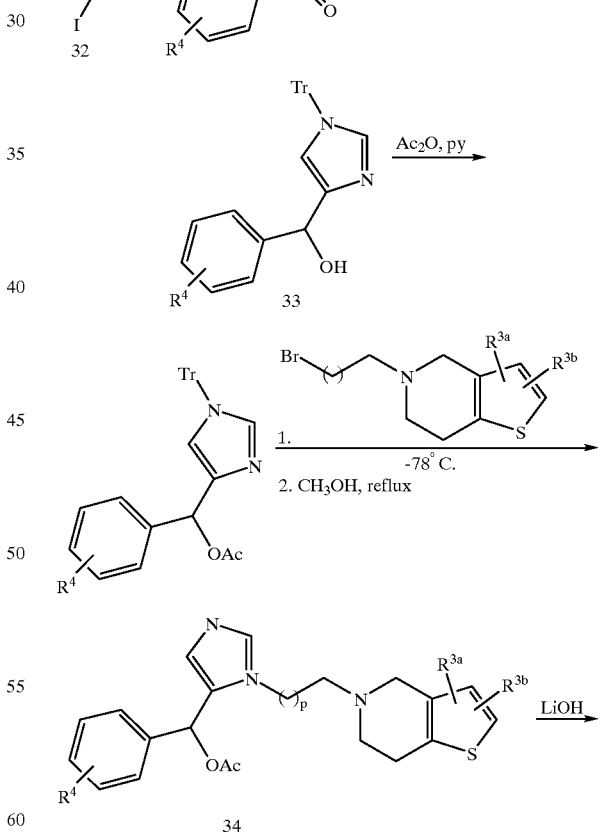

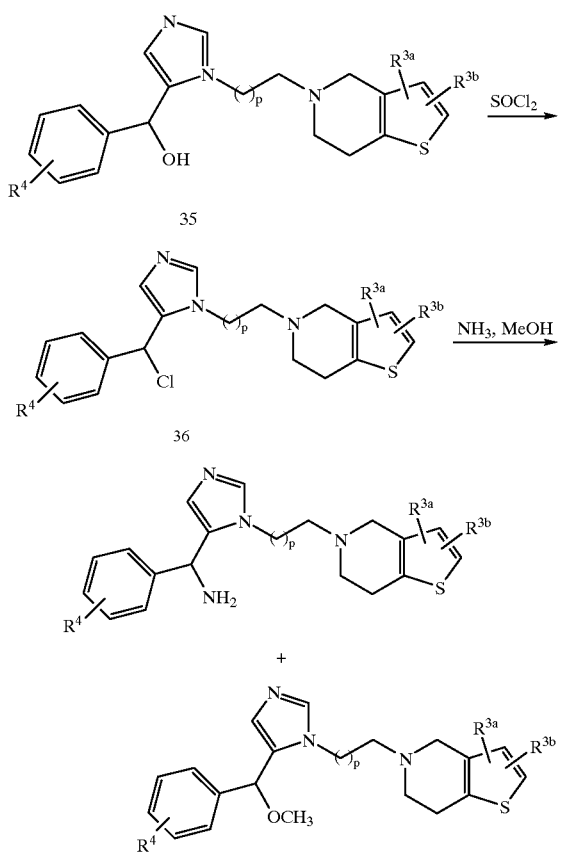
SCHEME 15
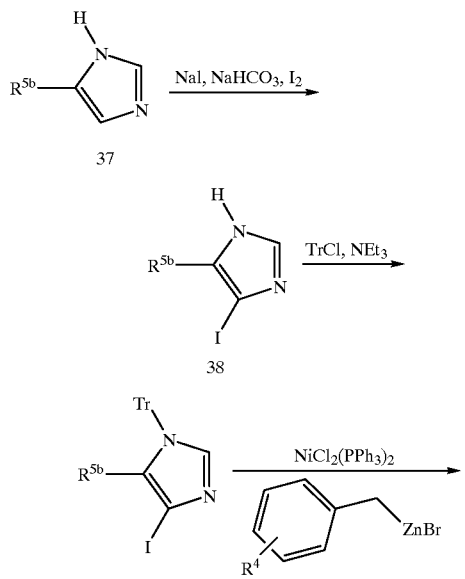
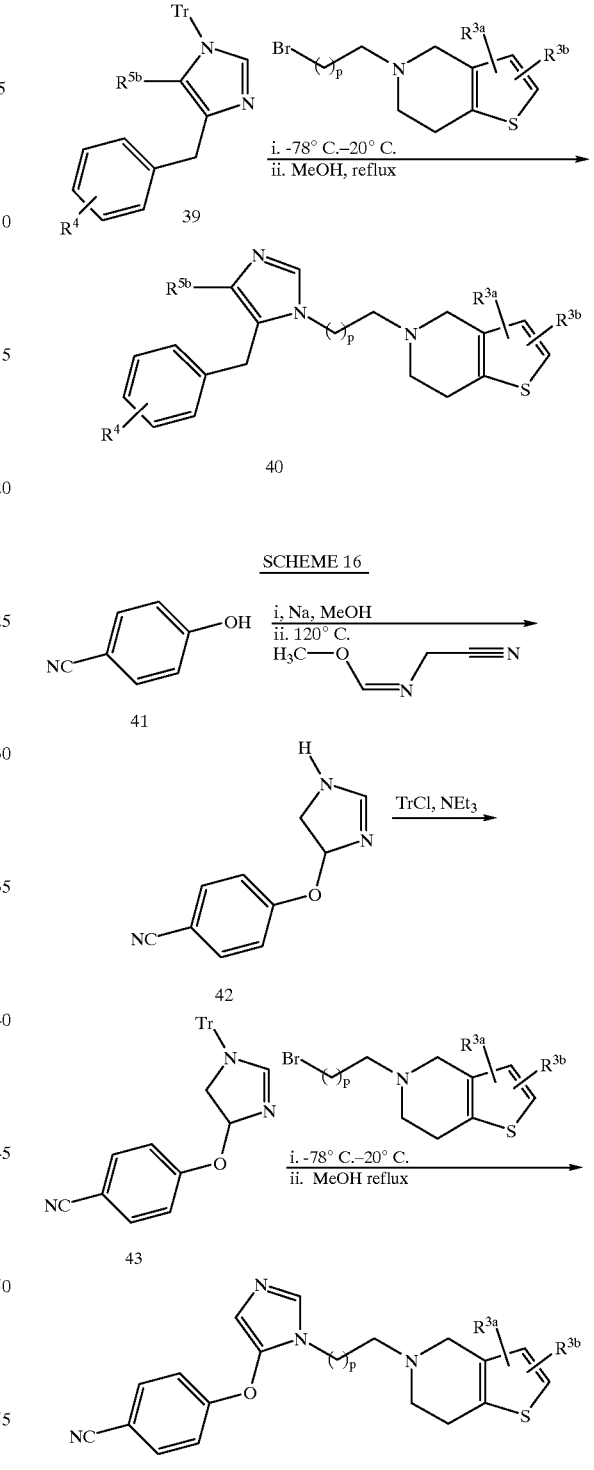
SCHEME 16
The instant compounds are useful as pharmaceutical agents for mammals, especially for humans. These compounds may be administered to patients for use in the treatment of cancer. Examples of the type of cancer which may be treated with the compounds of this invention include, but are not limited to, colorectal carcinoma, endocrine pancreatic carcinoma, myeloid leukemias and neurological tumors. Such tumors may arise by mutations in the ras genes themselves, mutations in the proteins that can regulate Ras activity (i.e., neurofibromin (NF-1), neu, scr, ab1, 1ck, fyn) or by other mechanisms.

The compounds of the instant invention inhibit farnesyl-protein transferase and the farnesylation of the oncogene protein Ras. The instant compounds may also inhibit tumor angiogenesis, thereby affecting the growth of tumors (J. Rak et al. *Cancer Research*, 55:4575–4580 (1995)). Such anti-angiogenesis properties of the instant compounds may also be useful in the treatment of certain forms of blindness related to retinal vascularization.

The compounds of this invention are also useful for inhibiting other proliferative diseases, both benign and malignant, wherein Ras proteins are aberrantly activated as a result of oncogenic mutation in other genes (i.e., the Ras gene itself is not activated by mutation to an oncogenic form) with said inhibition being accomplished by the administration of an effective amount of the compounds of the invention to a mammal in need of such treatment. For example, the compounds are useful in the treatment of neurofibromastosis, which is a benign proliferative disorder.

The instant compounds may also be useful in the treatment of certain viral infections, in particular in the treatment of hepatitis delta and related viruses (J. S. Glenn et al. *Science*, 256:1331–1333 (1992).

The compounds of the instant invention are also useful in the prevention of restenosis after percutaneous transluminal coronary angioplasty by inhibiting neointimal formation (C. Indolfi et al. *Nature medicine*, 1:541–545(1995).

The instant compounds may also be useful in the treatment and prevention of polycystic kidney disease (D. L. Schaffner et al. *American Journal of Pathology*, 142:1051–1060 (1993) and B. Cowley, Jr. et al. *FASEB Journal*, 2:A3160 (1988)).

The instant compounds may also be useful for the treatment of fungal infections.

In a preferred embodiment of the instant invention the compounds of this instant invention are selective inhibitors of farnesyl-protein transferase. A compound is considered a selective inhibitor of farnesyl-protein transferase, for example, when its in vitro farnesyl-protein transferase inhibitory activity, as assessed by the assay described in Example 6, is at least 100 times greater than the in vitro activity of the same compound against geranylgeranyl-protein transferase-type I in the assay described in Example 7. Preferably, a selective compound exhibits at least 1000 times greater activity against one of the enzymatic activities when comparing geranylgeranyl-protein transferase-type I inhibition and farnesyl-protein transferase inhibition.

In another preferred embodiment of the instant invention the compounds of this instant invention are dual inhibitors of farnesyl-protein transferase and geranylgeranyl-protein transferase type I. Such a dual inhibitor will exhibit certain characteristics when assessed in in vitro assays, which are dependent on the type of assay employed.

In a SEAP assay, such as described in Example 10, it is preferred that the dual inhibitor compound has an in vitro inhibitory activity ($IC_{50}$) that is less than about 12 $\mu$M against K4B-Ras dependent activation of MAP kinases in cells. More preferably, the dual inhibitor compound has an in vitro inhibitory activity ($IC_{50}$) against K4B-Ras dependent activation of MAP kinases in cells which is more than about 5 times lower than the inhibitory activity ($IC_{50}$) against Myr-Ras dependent activation of MAP kinases in cells. Also more preferably, in a SEAP assay, the dual inhibitor compound has an inhibitory activity ($IC_{50}$) that is less than about 10 nM against H-Ras dependent activation of MAP kinases in cells.

In a GGTase plus anion assay, such as described in Example 7, it is preferred that the dual inhibitor compound has an in vitro inhibitory activity ($IC_{50}$) that is less than about 5 $\mu$M against transfer of a geranylgeranyl residue to a protein or peptide substrate comprising a $CAAX^G$ motif by geranylgeranyl-protein transferase type I in the presence of a modulating anion. More preferably, the dual inhibitor compound has an in vitro inhibitory activity ($IC_{50}$) that is less than about 1 $\mu$M against transfer of a geranylgeranyl residue to a protein or peptide substrate comprising a $CAAX^G$ motif by geranylgeranyl-protein transferase type I in the presence of a modulating anion. Preferably, the dual inhibitor compound has an in vitro inhibitory activity ($IC_{50}$) in the in vitro assay as described in Example 6 that is less than about 1 $\mu$M against transfer of a farnesyl residue to a protein or peptide substrate, comprising a $CAAX^F$ motif, by farnesyl-protein transferase. more preferably, the dual inhibitor compound has an in vitro inhibitory activity ($IC_{50}$) that is less than about 100 nM against transfer of a farnesyl residue to a protein or peptide substrate, comprising a $CAAX^F$ motif, by farnesyl-protein transferase. Also preferably, the dual inhibitor compound has an in vitro inhibitory activity ($IC_{50}$) in the in vitro assay as described in Example 9, that is less than about 100 nM against the anchorage independent growth of H-ras-transformed mammalian fibroblasts.

The protein or peptide substrate utilized in the instant assay may incorporate any CAAX motif that is geranylgeranylated by GGTase-I. The term "$CAAX^G$" will refer to such motifs that may be geranylgeranylated by GGTase-I. It is understood that some of the "$CAAX^G$" containing protein or peptide substrates may also be farnesylated by farnesyl-protein transferase. In particular such "$CAAX^G$" motifs include (the corresponding human protein is in parentheses): CVIM (K4B-Ras), CVLL (mutated H-Ras), CVVM (N-Ras), CIIM (K4A-Ras), CLLL (Rap-IA), CQLL (Rap-IB), CSIM, CAIM, CKVL and CLIM (PFX). Preferably, the CAAX motif is CVIM.

As used herein, the term "$CAAX^F$" is used to designate a protein or peptide substrate that incorporates four amino acid C-terminus motif that is farnesylated by farnesyl-protein transferase. It is understood that certain of the "$CAAX^F$" containing protein or peptide substrates may also be geranylgeranylated by GGTase-I. In particular such "$CAAX^F$" motifs include (the corresponding human protein is in parentheses): CVLS (H-ras), CVIM (K4B-Ras) and CVVM (N-Ras).

The compounds of this invention may be administered to mammals, preferably humans, either alone or, preferably, in combination with pharmaceutically acceptable carriers or diluents, optionally with known adjuvants, such as alum, in a pharmaceutical composition, according to standard pharmaceutical practice. The compounds can be administered orally or parenterally, including the intravenous, intramuscular, intraperitoneal, subcutaneous, rectal and topical routes of administration.

For oral use of a chemotherapeutic compound according to this invention, the selected compound may be administered, for example, in the form of tablets or capsules, or as an aqueous solution or suspension. In the case of tablets for oral use, carriers which are commonly used include lactose and corn starch, and lubricating agents, such as magnesium stearate, are commonly added. For oral administration in capsule form, useful diluents include lactose and dried corn starch. When aqueous suspensions are required for oral use, the active ingredient is combined with emulsifying and suspending agents. If desired, certain sweetening and/or flavoring agents may be added. For intramuscular, intraperitoneal, subcutaneous and intravenous use, sterile solutions of the active ingredient are usually prepared, and the pH of the solutions should be suitably adjusted and buffered. For intravenous use, the total concentration of solutes should be controlled in order to render the preparation isotonic.

The present invention also encompasses a pharmaceutical composition useful in the treatment of cancer, comprising the administration of a therapeutically effective amount of the compounds of this invention, with or without pharmaceutically acceptable carriers or diluents. Suitable compositions of this invention include aqueous solutions comprising compounds of this invention and pharmacologically acceptable carriers, e.g., saline, at a pH level, e.g., 7.4. The solutions may be introduced into a patient's intramuscular blood-stream by local bolus injection.

As used herein, the term "composition" is intended to encompass a product comprising the specified ingredients in the specific amounts, as well as any product which results, directly or indirectly, from combination of the specific ingredients in the specified amounts.

When a compound according to this invention is administered into a human subject, the daily dosage will normally be determined by the prescribing physician with the dosage generally varying according to the age, weight, and response of the individual patient, as well as the severity of the patient's symptoms.

In one exemplary application, a suitable amount of compound is administered to a mammal undergoing treatment for cancer. Administration occurs in an amount between about 0.1 mg/kg of body weight to about 60 mg/kg of body weight per day, preferably of between 0.5 mg/kg of body weight to about 40 mg/kg of body weight per day.

The compounds of the instant invention are also useful as a component in an assay to rapidly determine the presence and quantity of farnesyl-protein transferase (FPTase) in a composition. Thus the composition to be tested may be divided and the two portions contacted with mixtures which comprise a known substrate of FPTase (for example a tetrapeptide having a cysteine at the amine terminus) and farnesyl pyrophosphate and, in one of the mixtures, a compound of the instant invention. After the assay mixtures are incubated for an sufficient period of time, well known in the art, to allow the FPTase to farnesylate the substrate, the chemical content of the assay mixtures may be determined by well known immunological, logical, radiochemical or chromatographic techniques. Because the compounds of the instant invention are selective inhibitors of FPTase, absence or quantitative reduction of the amount of substrate in the assay mixture without the compound of the instant invention relative to the presence of the unchanged substrate in the assay containing the instant compound is indicative of the presence of FPTase in the composition to be tested.

It would be readily apparent to one of ordinary skill in the art that such an assay as described above would be useful in identifying tissue samples which contain farnesyl-protein transferase and quantitating the enzyme. Thus, potent inhibitor compounds of the instant invention may be used in an active site titration assay to determine the quantity of enzyme in the sample. A series of samples composed of aliquots of a tissue extract containing an unknown amount of farnesyl-protein transferase, an excess amount of a known substrate of FPTase (for example a tetrapeptide having a cysteine at the amine terminus) and farnesyl pyrophosphate are incubated for an appropriate period of time in the presence of varying concentrations of a compound of the instant invention. The concentration of a sufficiently potent inhibitor (i.e., one that has a Ki substantially smaller than the concentration of enzyme in the assay vessel) required to inhibit the enzymatic activity of the sample by 50% is approximately equal to half of the concentration of the enzyme in that particular sample.

EXAMPLES

Examples provided are intended to assist in a further understanding of the invention. Particular materials employed, species and conditions are intended to be further illustrative of the invention and not limitative of the reasonable scope thereof. Purification by HPLC was utilized for the Examples as set forth below.

Example 1

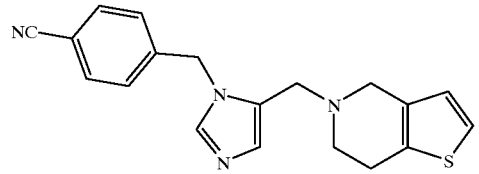

5-(1-(4-Cyanobenzyl)-5-imidazolylmethyl)-4,5,6,7-tetrahydrothieno[3,2-c]pyridine Step 1: Preparation of 1-triphenylmethyl-4-(hydroxymethyl) imidazole To a solution of 4-(hydroxymethyl)imidazole hydrochloride (35 g) in 250 mL of dry DMF at room temperature was added triethylamine (90.6 mL). A white solid precipitated from the solution. Chlorotriphenylmethane (76.1 g) in 500 mL of DMF was added dropwise. The reaction mixture was stirred for 20 hours, poured over ice, filtered, and washed with ice water. The resulting product was slurried with cold dioxane, filtered, and dried in vacuo to provide the title compound as a white solid which was sufficiently pure for use in the next step.

Step 2: Preparation of 1-triphenylmethyl-4-(acetoxymethyl) imidazole

The alcohol prepared above was suspended in 500 mL of pyridine. Acetic anhydride (74 mL) was added dropwise, and the reaction was stirred for 48 hours during which it became homogeneous. The solution was poured into 2 L of EtOAc, washed with water (3×1 L), 5% aq. HCl soln. (2×1 L), sat. aq. NaHCO$_3$, and brine, then dried (Na$_2$SO$_4$), filtered, and concentrated in vacuo to provide the crude product. The title compound was isolated as a white powder which was sufficiently pure for use in the next step.

Step 3: Preparation of 1-(4-cyanobenzyl)-5-(acetoxymethyl) imidazole hydrobromide A solution of the acetate from Step 2 (85.8 g) and α-bromo-p-tolunitrile (50.1 g) in 500 mL of EtOAc was stirred at 60° C. for 20 hours, during which a pale yellow precipitate formed. The reaction was cooled to room temperature and filtered to provide the solid imidazolium bromide salt. The filtrate was concentrated in vacuo to a volume 200 mL, reheated at 60° C. for two hours, cooled to room temperature, and filtered again. The filtrate was concentrated in vacuo to a volume 100 mL, reheated at 60° C. for another two hours, cooled to room temperature, and concentrated in vacuo to provide a pale yellow solid. All of the solid material was combined, dissolved in 500 mL of methanol, and warmed to 60° C. After two hours, the solution was reconcentrated in vacuo to provide a white solid which was triturated with hexane to remove soluble materials. Removal of residual solvents in vacuo provided the title hydrobromide as a white solid which was used in the next step without further purification.

Step 4: Preparation of 1-(4-cyanobenzyl)-5-(hydroxymethyl)imidazole

To a solution of the product from Step 3 (50.4 g) in 1.5 L of 3:1 THF/water at 0° C. was added lithium hydroxide monohydrate (18.9 g). After one hour, the reaction was concentrated in vacuo, diluted with EtOAc (3 L), and washed with water, sat. aq. $NaHCO_3$ and brine. The solution was then dried ($Na_2SO_4$), filtered, and concentrated in vacuo to provide the crude product as a pale yellow fluffy solid which was sufficiently pure for use in the next step without further purification.

Step 5: Preparation of 1-(4-cyanobenzyl)-5-imidazolecarboxaldehyde

To a solution of the alcohol from Step 4 (21.5 g) in 500 mL of DMSO at room temperature was added triethylamine (56 mL), then $SO_3$-pyridine complex (40.5 g). After 45 minutes, the reaction was poured into 2.5 L of EtOAc, washed with water (4×1 L) and brine, dried ($Na_2SO_4$), filtered, and concentrated in vacuo to provide the title aldehydLe as a white powder which was sufficiently pure for use in the next step without further purification.

Step 6: Preparation of 5-(1-(4-cyanobenzyl)-5-imidazolylmethyl)-4,5,6,7-tetrahydrothieno[3,2-]pyridine To a solution of 4,5,6,7-tetrahydrothieno[3,2-c]pyridine hydrochloride (Halczenko and Hartman; *Synthetic Commun.*, 1996, 26, 1363; 0.439 g, 2.5 mmol) in $CHCl_2CHCl_2$ (15 mL) was added 1-(4-cyanobenzyl)-5-imidazole carboxaldehyde (0.58 g, 2.75 mmol), 4 Å sieves and triethylamine (0.35 mL, 2.5 mmol) followed by NaBH (OAc)$_3$ (1.59 g, 7.5 mmol). The mixture was stirred at room temperature for 16 h., the mixture was diluted with EtOAc, filtered through celite, washed with brine, dried ($Na_2SO_4$) and concentrated. The residue was stirred in 2N HCl (50 mL) for 2 h. then extracted with ether. The aqueous layer was basified with 40% NaOH solution and extracted 3× $CH_2Cl_2$ which was then washed with brine, dried ($Na_2SO_4$) and the solvent evaporated in vacuo. Chromatography (silica gel; 2.5% MeOH in $CHCl_3$) followed by crystallization from ether afforded the title compound as a white solid.

Analysis for $C_{19}H_{18}N_4S \cdot 0.05\ CHCl_3$; Calcd. C, 67.21; H, 5.34; N,16.46; found C, 67.27; H, 5.26; N,16.61;

Example 2

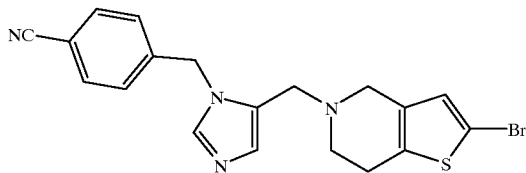

2-Bromo-5-(1-(4-cyanobenzyl)-5-imidazolylmethyl)-4,5,6,7-tetrahydrothieno[3,2-c]pyridine Step 1: Preparation of N-Boc-4,5,6,7-tetrahydrothieno[3,2-c]pyridine 4,5,6,7-Tetrahydrothieno[3,2-c]pyridine.HCl (7.38 g, 42 mmol) in $CHCl_3$ (150 mL) was treated with triethylamine (11.7 mL, 84 mmol) and (Boc)$_2$O (10.1 g, 46.2 mmol) for 5 h. The $CHCl_3$ was removed in vacuo and the residue partitioned between water and EtOAc. Extracted with EtOAc (3×), washed successively with 10% $KHSO_4$, brine, saturated $NaHCO_3$ then brine, dried and evaporated to give the title compound as a solid.

Step 2: Preparation of 2-bromo-4,5,6,7-tetrahydrothieno[3, 2-c]pyridine hydrobromide The product from Step 1 (9.57 g, 40 mmol) was dissolved in $CHCl_3$ (150 mL) at 0° C. and treated with bromine (2.1 mL, 40 mmol) dropwise over 10 minutes. The mixture was stirred for 16 h at room temperature then filtered to afford the title compound as a solid.

Step 3: Preparation of 2-bromo-5-(1-(4-cyanobenzyl)-5-imidazolylmethyl)-4,5,6,7-tetrahydrothieno[3,2-c]pyridine Following the procedure described for Example 1, Step 6 but using 2-bromo-4,5,6,7-tetrahydrothieno[3,2-c]pyridine the title compound was obtained as a white solid.

Analysis for $C_{19}H_{17}N_4BrS$; Calcd. C, 55.21; H, 4.15; N,13.56; found C, 55.67; H, 4.26; N,13.59.

Example 3

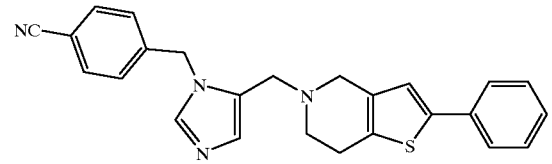

2-Phenyl-5-(1-(4-cyanobenzyl)-5-imidazolylmethyl)-4,5,6,7-tetrahydrothieno3,2-c]pyridine Step 1: Preparation of N-Boc-2-bromo-4,5,6,7-tetrahydrothieno[3,2-c]pyridine 2-bromo-4,5,6,7-tetrahydrothieno[3,2-c]pyridine hydrobromide (Example 2, Step 2; 6.67 g, 25 mmol) was converted to the Boc-protected derivative using (Boc)$_2$O (5.46 g, 25 mmol) in 150 mL dioxane and 75 mL 1N NaOH for 2 h. Work-up as described for Example 2, Step 1 afforded the title compound as a solid.

Step 2: Preparation of N-Boc-2-phenyl-4,5,6,7-tetrahydrothieno[3,2-c]pyridine

A solution of N-Boc-2-bromo-4,5,6,7-tetrahydrothieno[3, 2-c]pyridine (Step 1; 637 mg, 0.2 mmol), phenyl boronic acid (244 mg, 0.2 mmol), NaHCO3 (504 mg, 6 mmol) and tetrakis(triphenylphosphine)palladium(O) (116 mg, 0.1 mmol) in DME (10 mL) and water (10 mL) was heated to 80° C. for 20 h. The mixture was partitioned between water and EtOAc, washed with aqueous $NaHCO_3$, water (2×) then brine, dried and evaporated. Column chromatography of the residue (silica gel; hexane/EtOAc 95:5) afforded the title compound as a viscous oil.

Step 3: Preparation of 2-phenyl-4,5,6,7-tetrahydrothieno[3, 2-c]pyridine hydrochloride The product from Step 2 was dissolved in EtOAc at −25° C. and treated with HCl gas until saturated. The reaction was stoppered and stirred at 0° C. for 1 h. Removal of the solvent in vacuo afforded the title compound as a solid.

Step 4: Preparation of 2-phenyl-5-(1-(4-cyanobenzyl)-5-imidazolylmethyl)-4,5,6,7-tetrahydrothieno[3,2-c]pyridine Following the procedure described for Example 1, Step 6 but using 2-phenyl-4,5,6,7-tetrahydrothieno[3,2-c] pyridine.HCl the title compound was obtained as a white solid.

Analysis for $C_{25}H_{22}N_4S \cdot 0.25H_2O \cdot 0.1Et_2O$; Calcd. C, 72.21; H, 5.61; N,13.26; found C, 72.39; H, 5.31; N,13.00.

Example 4

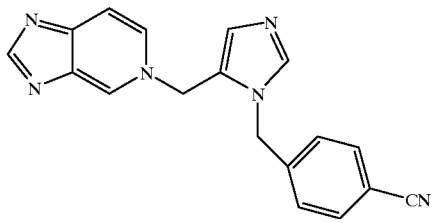

5-[5-(-Azabenzimidazolyl)methyl)-1-(4-cyanobenzyl)imidazole hydrochloride

Step 1: Preparation of 1-triphenylmethyl-4-(hydroxymethyl) imidazole

To a solution of 4-(hydroxymethyl)imidazole hydrochloride (35.0 g, 260 mmol) in 250 mL of dry DMF at room temperature was added triethylamine (90.6 mL, 650 mmol). A white solid precipitated from the solution. Chlorotriphenylmethane (76.1 g, 273 mmol) in 500 mL of DMF was added dropwise. The reaction mixture was stirred for 20 hours, poured over ice, filtered, and washed with ice water. The resulting product was slurried with cold dioxane, filtered, and dried in vccuo to provide the titled product as a white solid which was sufficiently pure for use in the next step.

Step 2: Preparation of 1-triphenylmethyl-4-(acetoxymethyl) imidazole

The alcohol described in Step 1 (260 mmol, prepared above) was suspended in 500 mL of pyridine. Acetic anhydride (74 mL, 780 mmol) was added dropwise, and the reaction was stirred for 48 hours during which it became homogeneous. The solution was poured into 2 L of EtOAc, washed with water (3×1 L), 5% aq. HCl soln. (2×1 L), sat. aq. NaHCO$_3$, and brine, then dried (Na$_2$SO$_4$), filtered, and concentrated in vacuo to provide the crude product. The acetate was isolated as a white powder, which was sufficiently pure for use in the next reaction.

Step 3: Preparation of 1-(4-cyanobenzyl)-5-(acetoxyrmethyl)imidazole hydrobromide A solution of the product descibed in Step 2 (85.8 g, 225 mmol) and α-bromo-p-tolunitrile (50.1 g, 232 mmol) in 500 mL of EtOAc was stirred at 60° C. for 20 hours, during which a pale yellow precipitate formed. The reaction was cooled to room temperature and filtered to provide the solid imidazolium bromide salt. The filtrate was concentrated in vacuo to a volume 200 mL, reheated at 60° C. for two hours, cooled to room temperature, and filtered again. The filtrate was concentrated in vacuo to a volume 100 mL, reheated at 60° C. for another two hours, cooled to room temperature, and concentrated in vacuo to provide a pale yellow solid. All of the solid material was combined, dissolved in 500 mL of methanol, and warmed to 60° C. After two hours, the solution was reconcentrated in vacuo to provide a white solid which was triturated with hexane to remove soluble materials. Removal of residual solvents in vacuo provided the titled product hydrobromide as a white solid, which was used in the next step without further purification.

Step 4: Preparation of 1-(4-cyanobenzyl)-5-(hydroxymethyl)imidazole

To a solution of the acetate described in Step 3 (50.4 g, 150 mmol) in 1.5 L of 3:1 THF/water at 0° C. was added lithium hydroxide monohydrate (18.9 g, 450 mmol). After one hour, the reaction was concentrated in vacuo, diluted with EtOAc (3 L), and washed with water, sat. aq. NaHCO$_3$ and brine. The solution was then dried (Na$_2$SO$_4$), filtered, and concentrated in vacuo to provide the crude product as a pale yellow fluffy solid which was sufficiently pure for use in the next step without further purification.

Step 5: Preparation of 5-(Chloromethyl)-1-(4-cyanobenzyl) imidazole hydrochloride The alcohol described in Step 4 (15.5 g, 72.9 mmol) was dissolved in thionyl chloride (150 mL) (exothermic!), and the reaction heated at 50° C. under argon for 48 h. Excess thionyl chloride was distilled in vacuo, and the resulting solid stirred in methylene chloride for 2 h. The solid was filtered and dried in vacuo, giving the title compound.

Step 6: Preparation of 5-(5-(5-azabenzimidazolyl)methyl)-1-(4-cyanobenzyl)imidazole hydrochloride To a solution of 5-azabenzimidazole (119 mg, 1.00 mmol) in 3 mL of dry DMF was added sodium hydride (88.0 mg, 2.20 mmol, 60% dispersion in mineral oil) at room temperature. After one hour, the solution was cooled to −50° C. and the chloride described in Step 5 (268 mg, 1.00 mmol) was added as a solid. The reaction was slowly warmed to room temperature over 16 hours, poured onto water, and extracted with methylene chloride (3×10 mL). The combined organic layers were dried (Na$_2$SO$_4$), filtered, and concentrated in vacuo to provide a yellow oil. The crude product was purified by column chromatography (10–30% MeOH/CHCl$_3$) and then treated with HCl to provide the title compound as a white solid. MS (FAB) m+1=315. elemental analysis for $C_{18}H_{14}N_6$•3.70 HCl•0.75 H$_2$O calc. C, 46.71; H, 4.18; N, 18.16; found C, 46.73; H, 4.17; N, 17.95.

Example 5

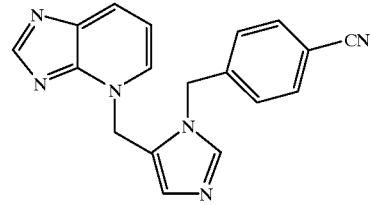

5-[4-(4-Azabenzimidazolyl)methyl)-1-(4-cyanobenzyl)imidazole hydrochloride

The title compound was prepared in a similar manner as described in Example 4, except 4-azabenzimidazole was used in Step 6. MS (FAB) m+1=315. elemental analysis for $C_{18}H_{14}N_6$•4.05 HCl•0.45 EtOAc calc. C, 47.40; H, 4.35; N, 16.75; found C, 47.34; H, 4.34; N, 16.76.

Example 6

In vitro Inhibition of ras Farnesyl Transferase

Assays of farnesyl-protein transferase. Partially purified bovine FPTase and Ras peptides (Ras-CVLS, Ras-CVIM and Ras-CAIL) were prepared as described by Schaber et al., *J. Biol. Chem.* 265:14701–14704 (1990), Pompliano, et al., *Biochemistry* 31:3800 (1992) and Gibbs et al., *PNA-S*U.S.A. 86:6630–6634 (1989), respectively. Bovine FPTase was assayed in a volume of 100 ml containing 100 mM N-(2-hydroxy ethyl) piperazine-N'-(2-ethane sulfonic acid) (HEPES), pH 7.4, 5 mM MgCl$_2$, 5 mM dithiothreitol (DTT), 100 mM [$^3$H]-farnesyl diphosphate ([$^3$H]-FPP; 740 CBq/mmol, New England Nuclear), 650 nM Ras-CVLS and 10 mg/ml FPTase at 31° C. for 60 min. Reactions were initiated with FPTase and stopped with 1 ml of 1.0 M HCL in ethanol.

Precipitates were collected onto filter-mats using a TomTec Mach II cell harvester, washed with 100% ethanol, dried and counted in an LKB b-plate counter. The assay was linear with respect to both substrates, FPTase levels and time; less than 10% of the [$^3$H]-FPP was utilized during the reaction period. Purified compounds were dissolved in 100% dimethyl sulfoxide (DMSO) and were diluted 20-fold into the assay. Percentage inhibition is measured by the amount of incorporation of radioactivity in the presence of the test compound when compared to the amount of incorporation in the absence of the test compound.

Human FPTase was prepared as described by Omer et al., *Biochemistry* 32:5167–5176 (1993). Human FPTase activity was assayed as described above with the exception that 0.1% (w/v) polyethylene glycol 20,000, 10 mM $ZnCl_2$ and 100 nM Ras-CVIM were added to the reaction mixture. Reactions were performed for 30 min., stopped with 100 ml of 30% (v/v) trichloroacetic acid (TCA) in ethanol and processed as described above for the bovine enzyme.

The compounds of the instant invention described in the above Examples were tested for inhibitory activity against human FPTase by the assay described above and were found to have $IC_{50}$ of <50 μM.

Example 7

Modified In vitro GGTase Inhibition Asssay

The modified geranylgeranyl-protein transferase inhibition assay is carried out at room temperature. A typical reaction contains (in a final volume of 50 mL): [$^3$H] geranylgeranyl diphosphate, biotinylated Ras peptide, 50 mM HEPES, pH 7.5, a modulating anion (for example 10 mM glycerophosphate or 5 mM ATP), 5 mM $MgCl_2$, 10 mM $ZnCl_2$, 0.1% PEG (15–20,000), 2 mM dithiothreitol, and geranylgeranyl-protein transferase type I(GGTase). The GGTase-type I enzyme employed in the assay is prepared as described in U.S. Pat. No. 5,470,832, incorporated by reference. The Ras peptide is derived from the K4B-Ras protein and has the following sequence: biotinyl-GKKKKKKSKTKCVIM (single amino acid code) (SEQ.ID.NO.: 1). Reactions are initiated by the addition of GGTase and stopped at timed intervals (typically 15 min) by the addition of 200 mL of a 3 mg/mL suspension of streptavidin SPA beads (Scintillation Proximity Assay beads, Amersham) in 0.2 M sodium phosphate, pH 4, containing 50 mM EDTA, and 0.5% BSA. The quenched reactions are allowed to stand for 2 hours before analysis on a Packard TopCount scintillation counter.

For inhibition studies, assays are run as described above, except inhibitors are prepared as concentrated solutions in 100% dimethyl sulfoxide and then diluted 25-fold into the enzyme assay mixture. $IC_{50}$ values are determined with Ras peptide near $K_M$ concentrations. Enzyme and nonsaturating substrate conditions for inhibitor $IC_{50}$ determinations are as follows: 75 pM GGTase-I, 1.6 mM Ras peptide, 100 nM geranylgeranyl diphosphate.

Example 8

Cell-based in vitro ras Prenylation Assay

The cell lines used in this assay consist of either Rat1 or $NIH_3T3$ cells transformed by either viral H-ras; an N-ras chimeric gene in which the C-terminal hypervariable region of viral-H-ras was substituted with the corresponding region from the N-ras gene; or ras-CVLL, a viral-H-ras mutant in which the C-terminal exon encodes leucine instead of serine, making the encoded protein a substrate for geranylgeranylation by GGTase-I. The assay can also be performed using cell lines transformed with human H-ras, N-ras or K4B-ras. The assay is performed essentially as described in DeClue, J. E. et al., Cancer Research 51:712–717, (1991). Cells in 10 cm dishes at 50–75% confluency are treated with the test compound(s) (final concentration of solvent, methanol or dimethyl sulfoxide, is 0.1%). After 4 hours at 37° C., the cells are labelled in 3 ml methionine-free DMEM supplemented with 10% regular DMEM, 2% fetal bovine serum, 400 mCi[$^{35}$S]methionine (1000 Ci/mmol) and test compound(s). Cells treated with lovastatin, a compound that blocks Ras processing in cells by inhibiting the rate-limiting step in the isoprenoid biosynthetic pathway (Hancock, J. F. et al. *Cell*, 57:1167 (1989); DeClue, J. E. et al. *Cancer Res.*, 51:712 (1991); Sinensky, M. et al. *J. Biol. Chem.*, 265:19937 (1990)), serve as a positive control in this assay. After an additional 20 hours, the cells are lysed in 1 ml lysis buffer (1% NP40/20 mM HEPES, pH 7.5/5 mM $MgCl_2$/1 mM DTT/10 mg/ml aprotinen/2 mg/ml leupeptin/2 mg/ml antipain/0.5 mM PMSF) and the lysates cleared by centrifugation at 100,000×g for 45 min. Alternatively, four hours after the additon of the labelling media, the media is removed, the cells washed, and 3 ml of media containing the same or a different test compound added. Following an additional 16 hour incubation, the lysis is carried out as above. Aliquots of lysates containing equal numbers of acid-precipitable counts are bought to 1 ml with IP buffer (lysis buffer lacking DTT) and immunoprecipitated with the ras-specific monoclonal antibody Y13-259 (Furth, M. E. et al., J. Virol. 43:294–304, (1982)). Following a 2 hour antibody incubation at 4° C., 200 ml of a 25% suspension of protein.A-Sepharose coated with rabbit anti rat IgG is added for 45 min. The immunoprecipitates are washed four times with IP buffer (20 nM HEPES, pH 7.5/1 mM EDTA/1% Triton X-100.0.5% deoxycholate/0.1 %/SDS/0.1 M NaCl) boiled in SDS-PAGE sample buffer and loaded on 13% acrylamide gels. When the dye front reached the bottom, the gel is fixed, soaked in Enlightening, dried and autoradiographed. The intensities of the bands corresponding to prenylated and nonprenylated Ras proteins are compared to determine the percent inhibition of prenyl transfer to protein.

Example 9

Cell-based in vitro Anchorage Independent Growth Assay (SALSA)

SALSA (Soft Agar-Like Surrogate Assay) measures the inhibition of anchorage-independent growth by prenyl-transferase inhibitors. Only transformed cells are able to grow anchorage-independently in the SALSA format. Additionally, cells growing in the SALSA format grow in clumps, resembling the colonies formed in soft agar. SALSA may been used to measure the growth inhibition by prenyl-transferase inhibitors in a variety of transformed cell lines, including Rat1 fibroblasts transformed with viral-H-ras (H-ras/rat1), as well as a panel of human tumor cell lines (HTL's).

SALSA is performed in 96-well plates that are coated with a thin film of the polymer, PolyHEMA (Poly(2-hydroxyethyl methacrylate)), which prevents cells from attaching to the plate. Rat1 fibroblast cells transformed with v-Ha-ras (this cell line has been deposited in the ATCC on Aug. 19, 1997 under the terms of the Budapest convention and has been given a designation of ATCC CRL 1287) are seeded at 5000 cells/well, grown for 4 hr, then vehicle or half-log dilutions of test compound (in either an 8 or 12 point titration) are added. The cells are then grown for 6 days at 37 degrees, without changing the growth media or adding fresh compound. At day 6, cell growth is assessed via a calorimetric assay that measures the cleavage of the tetrazolium dye, MTT, to an insoluble purple formazan, a reaction dependent upon mitochondrial dehydrogenases. At day 6, the cells are incubated for 4 hr with 0.5 mg/ml MTT, and then SDS is added to 9% w/v to lyse the cells and solubilize the insoluble MTT-formazan. The amount of MTT metabolism is quantitated via spectrophotometric detection at 570 nM. Dose-inhibition curves and $IC_{50}$'s are determined.

Example 10

Construction of SEAP Reporter Plasmid pDSE100

The SEAP reporter plasmid, pDSE100 was constructed by ligating a restriction fragment containing the SEAP coding sequence into the plasmid pCMV-RE-AKI. The SEAP gene is derived from the plasmid pSEAP2-Basic (Clontech, Palo Alto, Calif.). The plasmid pCMV-RE-AKI was constructed by Deborah Jones (Merck) and contains 5 sequential copies of the 'dyad symmetry response element' cloned upstream of a 'CAT-TATA' (SEQ.ID.NO.: 15) sequence derived from the cytomegalovirus immediate early promoter. The plasmid also contains a bovine growth hormone poly-A sequence.

The plasmid, pDSE100 was constructed as follows. A restriction fragment encoding the SEAP coding sequence was cut out of the plasmid pSEAP2-Basic using the restriction enzymes EcoR1 and HpaI. The ends of the linear DNA fragments were filled in with the Klenow fragment of *E. coli* DNA Polymerase I. The 'blunt ended' DNA containing the SEAP gene was isolated by electrophoresing the digest in an agarose gel and cutting out the 1694 base pair fragment. The vector plasmid pCMV-RE-AKI was linearized with the restriction enzyme Bgl-II and the ends filled in with Klenow DNA Polymerase I. The SEAP DNA fragment was blunt end ligated into the pCMV-RE-AKI vector and the ligation products were transformed into DH5-alpha *E. coli* cells (Gibco-BRL). Transformants were screened for the proper insert and then mapped for restriction fragment orientation. Properly oriented recombinant constructs were sequenced across the cloning junctions to verify the correct sequence. The resulting plasmid contains the SEAP coding sequence downstream of the DSE and CAT-TATA promoter elements and upstream of the BGH poly-A sequence.

Cloning of a Myristylated Viral-H-ras Expression Plasmid

A DNA fragment containing viral-H-ras can be PCRed from plasmid "H-1" (Ellis R. et al. J. Virol. 36, 408, 1980) using the following oligos.

Sense strand: 5'TCTCCTCGAGGCCACCATGGGGAG-TAGCAAGAGCAAGCCTAA GGACCCCAGCCAGCGC-CGGATGACAGAATACAAGCTTGTGGTG G 3'. (SEQ.ID.NO.: 2)

Antisense: 5'CACATCTAGATCAGGACAGCACA-GACTTGCAGC 3'. (SEQ.ID.NO.: 3)

A sequence encoding the first 15 aminoacids of the v-src gene, containing a myristylation site, is incorporated into the sense strand oligo. The sense strand oligo also optimizes the 'Kozak' translation initiation sequence immediately 5' to the ATG start site.To prevent prenylation at the viral-ras C-terminus, cysteine 186 would be mutated to a serine by substituting a G residue for a C residue in the C-terminal antisense oligo. The PCR primer oligos introduce an XhoI site at the 5' end and a XbaI site at the 3' end. The XhoI-XbaI fragment can be ligated into the mammalian expression plasmid pCI (Promega) cut with XhoI and XbaI. This results in a plasmid in which the recombinant myr-viral-H-ras gene is constitutively transcribed from the CMV promoter of the pCI vector.

Cloning of a Viral-H-ras-CVLL Expression Plasmid

A viral-H-ras clone with a C-terminal sequence encoding the amino acids CVLL can be cloned from the plasmid "H-1" (Ellis R. et al. J. Virol. 36, 408, 1980) by PCR using the following oligos.

Sense strand: 5'TCTCCTCGAGGCC ACCATGACAGAATACAAGCTTGTGGTGG-3' (SEQ.ID.NO.: 4)

Antisense strand: 5'CACTCTAGACTGCGTGTCAGA GCAGCACACACTTGCAGC-3' (SEQ.ID.NO.: 5)

The sense strand oligo optimizes the 'Kozak' sequence and adds an XhoI site. The antisense strand mutates serine 189 to leucine and adds an XbaI site. The PCR fragment can be trimmed with XhoI and XbaI and ligated into the XhoI-XbaI cut vector pCI (Promega). This results in a plasmid in which the mutated viral-H-ras-CVLL gene is constitutively transcribed from the CMV promoter of the pCI vector.

Cloning of c-H-ras-Leu61 Expression Plasmid

The human c-H-ras gene can be PCRed from a human cerebral cortex cDNA library (Clontech) using the following oligonucleotide primers.

Sense strand: 5'-GAGAGAATTCGCCACCATGAC GGAATATAAGCTGGTGG-3' (SEQ.ID.NO.: 6)

Antisense strand: 5'-GAGAGTCGACGCGTCAGGAGA GCACACACTTGC-3' (SEQ.ID.NO.: 7)

The primers will amplify a c-H-ras encoding DNA fragment with the primers contributing an optimized 'Kozak' translation start sequence, an EcoRI site at the N-terminus and a Sal I stite at the C-terminal end. After trimming the ends of the PCR product with EcoRI and Sal I, the c-H-ras fragment can be ligated ligated into an EcoRI -Sal I cut mutagenesis vector pAlter-1 (Promega). Mutation of glutamine-61 to a leucine can be accomplished using the manufacturer's protocols and the following oligonucleotide:

5'-CCGCCGGCCTGGAGGAGTACAG-3' (SEQ.ID.NO.: 8)

After selection and sequencing for the correct nucleotide substitution, the mutated c-H-ras-Leu61 can be excised from the pAlter-1 vector, using EcoRI and Sal I, and be directly ligated into the vector pCI (Promega) which has been digested with EcoRI and Sal I. The new recombinant plasmid will constitutively transcribe c-H-ras-Leu61 from the CMV promoter of the pCI vector.

Cloning of a c-N-ras-Val-12 Expression Plasmid

The human c-N-ras gene can be PCRed from a human cerebral cortex cDNA library (Clontech) using the following oligonucleotide primers.

Sense strand: 5'-GAGAGAATTCGCCACCATGAC TGAGTACAAACTGGTGG-3' (SEQ.ID.NO.: 9)

Antisense strand: 5'-GAGAGTCGACTTGTTACATCA CCACACATGGC-3' (SEQ.ID.NO.: 10)

The primers will amplify a c-N-ras encoding DNA fragment with the primers contributing an optimized 'Kozak' translation start sequence, an EcoRI site at the N-terminus and a Sal I stite at the C-terminal end. After trimming the ends of the PCR product with EcoRI and Sal I, the c-N-ras fragment can be ligated into an EcoRI -Sal I cut mutagenesis vector pAlter-1 (Promega). Mutation of glycine-12 to a valine can be accomplished using the manufacturer's protocols and the following oligonucleotide:

5'-GTTGGAGCAGTTGGTGTTGGG-3' (SEQ.ID.NO.: 11)

After selection and sequencing for the correct nucleotide substitution, the mutated c-N-ras-Val-12 can be excised from the pAlter-1 vector, using EcoRI and Sal I, and be directly ligated into the vector pCI (Promega) which has been digested with EcoRI and Sal I. The new recombinant plasmid will constitutively transcribe c-N-ras-Val-12 from the CMV promoter of the pCI vector.

Cloning of a c-K-ras-Val-12 Expression Plasmid

The human c-K-ras gene can be PCRed from a human cerebral cortex cDNA library (Clontech) using the following oligonucleotide primers.

Sense strand: 5'-GAGAGGTACCGCCACCATGAC TGAATATAAACTTGTGG-3' (SEQ.ID.NO.: 12)

Antisense strand: 5'-CTCTGTCGACGTATTTACATA ATTACACACTTTGTC-3' (SEQ.ID.NO.: 13)

The primers will amplify a c-K-ras encoding DNA fragment with the primers contributing an optimized 'Kozak' translation start sequence, a KpnI site at the N-terminus and a Sal I stite at the C-terminal end. After trimming the ends of the PCR product with Kpn I and Sal I, the c-K-ras fragment can be ligated into a KpnI -Sal I cut mutagenesis vector pAlter-1 (Promega). Mutation of cysteine-12 to a valine can be accomplished using the manufacturer's protocols and the following oligonucleotide:

5'-GTAGTTGGAGCTGTTGGCGTAGGC-3' (SEQ.ID.NO.: 14)

After selection and sequencing for the correct nucleotide substitution, the mutated c-K-ras-Val-12 can be excised from the pAlter-1 vector, using KpnI and Sal I, and be directly ligated into the vector pCI (Promega) which has been digested with KpnI and Sal I. The new recombinant plasmid will constitutively transcribe c-K-ras-Val-12 from the CMV promoter of the pCI vector.

SEAP Assay

Human $C_{33}A$ cells (human epitheial carcenoma—ATTC collection) are seeded in 10 cm tissue culture plates in DMEM+10% fetal calf serum+1× Pen/Strep+1× glutamine+1× NEAA. Cells are grown at 37° C. in a 5% $CO_2$ atmosphere until they reach 50–80% of conflunecy.

The transient transfection is performed by the $CaPO_4$ method (Sambrook et al., 1989). Thus, expression plasmids for H-ras, N-ras, K-ras, Myr-ras or H-ras-CVLL are co-precipitated with the DSE-SEAP reporter construct. For 10 cm plates 600 ml of $CaCl_2$-DNA solution is added dropwise while vortexing to 600 ml of 2× HBS buffer to give 1.2 ml of precipitate solution (see recipes below). This is allowed to sit at room temperature for 20 to 30 minutes. While the precipitate is forming, the media on the C33A cells is replaced with DMEM (minus phenol red; Gibco cat. #31053-028)+0.5% charcoal stripped calf serum +1× (Pen/Strep, Glutamine and nonessential aminoacids). The $CaPO_4$-DNA precipitate is added dropwise to the cells and the plate rocked gently to distribute. DNA uptake is allowed to proceed for 5–6 hrs at 37° C. under a 5% $CO_2$ atmosphere.

Following the DNA incubation period, the cells are washed with PBS and trypsinized with 1 ml of 0.05% trypsin. The 1 ml of trypsinized cells is diluted into 10 ml of phenol red free DMEM +0.2% charcoal stripped calf serum+1× (Pen/Strep, Glutamine and NEAA). Transfected cells are pLated in a 96 well microtiter plate (100 ml/well) to which drug, diluted in media, has already been added in a volume of 100 ml. The final volume per well is 200 ml with each drug concentration repeated in triplicate over a range of half-log steps.

Incubation of cells and drugs is for 36 hrs at 37° under $CO_2$. At the end of the incubation period, cells are examined microscopically for evidence of cell distress. Next, 100 ml of media containing the secreted alkaline phosphatase is removed from each well and transferred to a microtube array for heat treatment at 65° C. for 1 hr to inactivate endogenous alkaline phosphatases (but not the heat stable secreted phosphatase).

The heat treated media is assayed for alkaline phosphatase by a luminescence assay using the luminescence reagent CSPD® (Tropix, Bedford, Mass.). A volume of 50 ml media is combinRased with 200 ml of CSPD cocktail and incubated for 60 minutes at room temperature. Luminesence is monitored using an ML2200 microplate luminometer (Dynatech). Luminescence reflects the level of activation of the fos reporter construct stimulated by the transiently expressed protein.

DNA-$CaPO_4$ precipitate for 10 cm. plate of cells

| | |
|---|---|
| Ras expression plasmid (1 mg/ml) | 10 ml |
| DSE-SEAP Plasmid (1 mg/ml) | 2 ml |
| Sheared Calf Thymus DNA (1 mg/ml) | 8 ml |
| 2M $CaCl_2$ | 74 ml |
| $dH_2O$ | 506 ml |

2× HBS Buffer 280 mM NaCl 10 mM KCl 1.5 mM $Na_2HPO_4$ $2H_2O$ 12 mM dextrose 50 mM HEPES Final pH=7.05

Luminesence Buffer (26 ml)

| | |
|---|---|
| Assay Buffer | 20 ml |
| Emerald Reagent ™ (Tropix) | 2.5 ml |
| 100 mM homoarginine | 2.5 ml |
| CSPD Reagent ® (Tropix) | 1.0 ml |

Assay Buffer

Add 0.05M $Na_2CO_3$ to 0.05M $NaHCO_3$ to obtain pH 9.5. Make 1 mM in $MgCl_2$

Example 11

In vivo Tumor Growth Inhibition Assay (nude mouse)

In vivo efficacy as an inhibitor of the growth of cancer cells may be confirmed by several protocols well known in the art. Examples of such in vivo efficacy studies are described by N. E. Kohl et al. (*Nature Medicine*, 1:792–797 (1995)) and N. E. Kohl et al. (*Proc. Nat. Acad. Sci. U.S.A.*, 91:9141–9145 (1994)).

Rodent fibroblasts transformed with oncogenically mutated human Ha-ras or Ki-ras ($10^6$ cells/animal in 1 ml of DMEM salts) are injected subcutaneously into the left flank of 8–12 week old female nude mice (Harlan) on day 0. The mice in each oncogene group are randomly assigned to a vehicle, compound or combination treatment group. Animals are dosed subcutaneously starting on day 1 and daily for the duration of the experiment. Alternatively, the farnesyl-protein transferase inhibitor may be administered by a continuous infusion pump. Compound, ccmpound combination or vehicle is delivered in a total volume of 0.1 ml. Tumors are excised and weighed when all of the vehicle-treated animals exhibited lesions of 0.5–1.0 cm in diameter, typically 11–15 days after the cells were injected. The average weight of the tumors in each treatment group for each cell line is calculated.

What is claimed is:

1. A compound which inhibits farnesyl-protein transferase of the formula I:

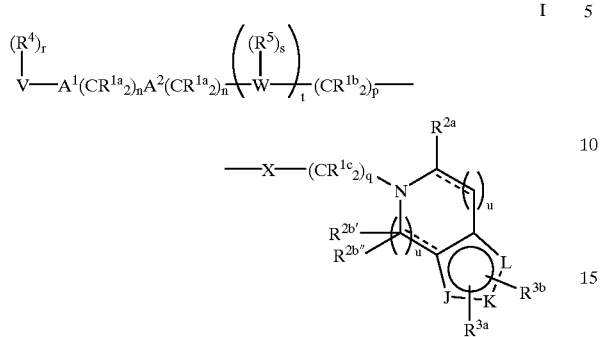

wherein:

$R^{1a}$, $R^{1b}$ and $R^{1c}$ are independently selected from:
  a) hydrogen,
  b) unsubstituted or substituted aryl, unsubstituted or substituted heterocycle, $C_3$–$C_{10}$ cycloalkyl, $C_2$–$C_6$ alkenyl, $C_2$–$C_6$ alkynyl, $R^8O$—, $R^9S(O)_m$—, $R^8C(O)NR^8$—, CN, NO$_2$, $(R^8)_2N$—$C(NR^8)$—, $R^8C(O)$—, $R^8OC(O)$—, N$_3$, —N$(R^8)_2$, or $R^9OC(O)NR^8$—,
  c) $C_1$–$C_6$ alkyl unsubstituted or substituted by unsubstituted or substituted aryl, heterocyclic, $C_3$–$C_{10}$ cycloalkyl, $C_2$–$C_6$ alkenyl, $C_2$–$C_6$ alkynyl, $R^8O$—, $R^9S(O)_m$—, $R^8C(O)NR^8$—, CN, $(R^8)_2N$—$C(NR^8)$—, $R^8C(O)$—, $R^8OC(O)$—, N$_3$, —N$(R^8)_2$, or $R^9OC(O)$—NR$^8$—,
provided that $R^{1a}$ is not unsubstituted or substituted imidazolyl;

$R^{2a}$, $R^{2b'}$ and $R^{2b''}$ are independently hydrogen or —$(CR^{11}_2)_vA^3(CR^{12}_2)_wR^{13}$; or $R^{2b'}$ and $R^{2b''}$ are combined as O;

$R^{3a}$ and $R^{3b}$ are independently selected from:
  a) hydrogen,
  b) unsubstituted or substituted aryl, unsubstituted or substituted heterocycle, unsubstituted or substituted $C_3$–$C_{10}$ cycloalkyl, unsubstituted or substituted $C_2$–$C_6$ alkenyl, $C_2$–$C_6$ alkynyl, halogen, $C_1$–$C_6$ perfluoroalkyl, $R^9O$—, $R^9S(O)_m$—, $R^8C(O)NR^8$—, $(R^8)_2NC(O)$—, $R^9C(O)O$—, $R^8_2N$—$C(NR^8)$—, CN, NO$_2$, $R^8C(O)$—, N$_3$, —N$(R^8)_2$, or $R^9OC(O)NR^8$—,
  c) unsubstituted $C_1$–$C_6$ alkyl,
  d) substituted $C_1$–$C_6$ alkyl wherein the substituent on the substituted $C_1$–$C_6$ alkyl is selected from unsubstituted or substituted aryl, unsubstituted or substituted heterocyclic, $C_3$–$C_{10}$ cycloalkyl, $C_2$–$C_6$ alkenyl, $C_2$–$C_6$ alkynyl, $R^9O$—, $R^9S(O)_m$—, $R^8C(O)NR^8$—, $(R^8)_2NC(O)$—, $R^8_2N$—$C(NR^8)$—, CN, $R^8C(O)$—, N$_3$, —N$(R^8)_2$, and $R^9OC(O)$—NR$^8$—;

$R^4$ is independently selected from:
  a) hydrogen,
  b) unsubstituted or substituted aryl or substituted heterocycle, $C_3$–$C_{10}$ cycloalkyl, $C_2$–$C_6$ alkenyl, $C_2$–$C_6$ alkynyl, perfluoroalkyl, F, Cl, Br, $R^8O$—, $R^9S(O)_m$—, $R^8C(O)NR^8$—, CN, NO$_2$, $R^8_2N$—$C(NR^8)$—, $R^8C(O)$—, $R^8OC(O)$—, N$_3$, —N$(R^8)_2$, or $R^9OC(O)NR^8$—, and
  c) $C_1$–$C_6$ alkyl urisubstituted or substituted by aryl, heterocycle, $C_3$–$C_{10}$ cycloalkyl, $C_2$–$C_6$ alkenyl, $C_2$–$C_6$ alkynyl, perfluoroalkyl, F, Cl, Br, $R^8O$—, $R^9S(O)_m$—, $R^8C(O)NH$—, CN, H$_2$N—C(NH)—, $R^8C(O)$—, $R^8OC(O)$—, N$_3$, —N$(R^8)_2$, or $R^8OC(O)NH$—, provided that $R^4$ is not unsubstituted or substituted imidazolyl;

$R^5$ is independently selected from:
  a) hydrogen,
  b) $C_2$–$C_6$ alkenyl, $C_2$–$C_6$ alkynyl, $C_3$–$C_6$ cycloalkyl, perfluoroalkyl, F, Cl, Br, $R^8O$—, $R^9S(O)_m$—, $R^8C(O)NR^8$—, CN, NO$_2$, $(R^8)_2N$—$C$—$(NR^8)$—, $R^8C(O)$—, $R^8OC(O)$—, N$_3$, —N$(R^8)_2$, or $R^9OC(O)NR^8$—, and
  c) $C_1$–$C_6$ alkyl, unsubstituted or substituted by perfluoroalkyl, F, Cl, Br, $R^8O$—, $R^9S(O)_m$—, $R^8C(O)NR^8$—, CN, $(R^8)_2N$—$C(NR^8)$—, $R^8C(O)$—, $R^8OC(O)$—, N$_3$, —N$(R^8)_2$, or $R^9OC(O)NR^8$—;

$R^8$ is independently selected from hydrogen, $C_1$–$C_6$ alkyl, benzyl, 2,2,2-trifluoroethyl and aryl;

$R^9$ is independently selected from $C_1$–$C_6$ alkyl and aryl;

$R^{10}$ is selected from: H; $R^8C(O)$—; $R^9S(O)_m$—; unsubstituted or substituted $C_{1-4}$ alkyl, unsubstituted or substituted $C_{1-6}$ cycloalkyl, unsubstituted or substituted heterocycle, unsubstituted or substituted aryl, substituted aroyl, unsubstituted or substituted heteroaroyl, substituted arylsulfonyl, unsubstituted or substituted heteroarylsulfonyl, wherein the substituted group is substituted with one or two substituents selected from:
  a) $C_{1-4}$ alkoxy,
  b) aryl or heterocycle,
  c) halogen,
  d) HO, e)
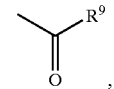

f)
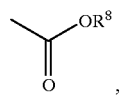

g)
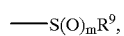

h) $N(R^8)_2$, or
  i) $C_{3-6}$ cycloalkyl;

$R^{11}$ and $R^{12}$ are independently selected from:
  a) hydrogen,
  b) $C_1$–$C_6$ alkyl unsubstituted or substituted by $C_2$–$C_{20}$ alkenyl, $R^8O$—, $R^9S(O)_m$—, $R^8C(O)NR^8$—, CN, N$_3$, $(R^8)_2N$—$C(NR^8)$—, $R^8C(O)$—, —N$(R^8)_2$, or $R^9OC(O)NR^8$—,
  c) unsubstituted or substituted aryl, unsubstituted or substituted heterocycle, $C_3$–$C_{10}$ cycloalkyl, $C_2$–$C_{20}$ alkenyl, halogen, $R^8O$—, $R^9S(O)_m$—, $R^8C(O)NR^8$—, CN, NO$_2$, $(R^8)_2N$—$C(NR^8)$—, $R^8C(O)$—, N$_3$, —N$(R^8)_2$, or $R^9OC(O)NR^8$—, and
  d) $C_1$–$C_6$ alkyl substituted with an unsubstituted or substituted group selected from aryl, heterocyclic and $C_3$–$C_{10}$ cycloalkyl;

$R^{13}$ is selected from:
  a) hydrogen,
  b) substituted or unsubstituted aryl, substituted or unsubstituted heterocycle, $C_3$–$C_{10}$ cycloalkyl, $C_2$–$C_{20}$ alkenyl, $C_2$–$C_{20}$ alkynyl, $C_1$–$C_{20}$ perfluoroalkyl, allyloxy, F, Cl, Br, $R^8O$—, $R^9S(O)_m$—, $R^8C(O)NR^8$—, CN, NO$_2$, $R^8_2N$—$C(NR^8)$—, $R^8C(O)$—, N$_3$, —N$(R^8)_2$, $(R^8)_2NC(O)$— or $R^9OC(O)NR^8$—, and c) $C_1$–$C_6$ alkyl unsubstituted or substituted by substituted or unsubstituted aryl, substituted or unsubstituted heterocycle, $C_3$–$C_{10}$ cycloalkyl, $C_2$–$C_{20}$ alkenyl, $C_2$–$C_{20}$ alkynyl, $C_2$–$C_{20}$ perfluoroalkyl, F, Cl, Br, $R^8O$—, $R^9S(O)_m$—, $R^8C(O)NH$—, CN, $H_2N$—$C(NH)$—, $R^8C(O)$—, $N_3$, —$N(R^8)_2$, or $R^9OC(O)NH$—;

$A^1$ and $A^2$ are independently selected from: a bond, —CH═CH—, —C≡C—, —C(O)—, —C(O)$NR^8$—, —$NR^8C(O)$—, O, —$N(R^8)$—, —$S(O)_2N(R^8)$—, —$N(R^8)S(O)_2$—, or —$S(O)_m$;

$A^3$ are independently selected from: a bond, —CH═CH—, —C≡C—, —C(O)—, —C(O)$NR^{10}$—, —$NR^{10}C(O)$—, O, —$N(R^{10})$—, —$S(O)_2N(R^{10})$—, —$N(R^{10})S(O)_2$—, or —$S(O)_m$;

J-K-L represents CH═CH—S;

V is selected from:
 a) hydrogen,
 b) heterocycle,
 c) aryl,
 d) $C_1$–$C_{20}$ alkyl wherein from 0 to 4 carbon atoms are replaced with a heteroatom selected from O, S, and N, and
 e) $C_2$–$C_{20}$ alkenyl, provided that V is not hydrogen if $A^1$ is —$S(O)_m$ and V is not hydrogen if $A^1$ is a bond, n is 0 and $A^2$ is —$S(O)_m$;
and provided that V is not imidazolyl;

W is imidazolyl;

X is a bond, —$S(O)_m$—, O or —C(═O)—;

m is 0, 1 or 2;

n is 0, 1, 2, 3 or 4;

p is 0, 1, 2, 3 or 4;

q is 0, 1, 2, 3 or 4, provided that q is not 0 or 1 if X is O;

r is 0 to 5, provided that r is 0 when V is hydrogen;

s is 1 or 2;

t is 1;

u is independently 0,1 or 2; provided that the sum of the u variables is equal to 2;

v is 0, 1, 2, 3 or 4, provided that v is not 0 when $A^3$ is —$NR^{10}C(O)$—, O, —$N(R^{10})$—, —$S(O)_2N(R^{10})$—, —$N(R^{10})S(O)_2$—, or $S(O)_m$;

w is 0, 1, 2, 3 or 4; and the dashed lines represent optional double bonds;

or an optical isomer or a pharmaceutically acceptable salt thereof.

2. The compound according to claim 1 which inhibits farnesyl-protein transferase of the formula A:

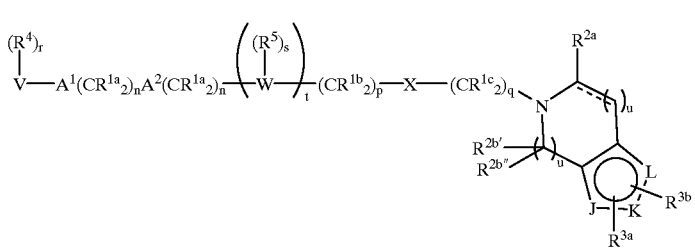

A wherein:

$R^{1a}$, $R^{1b}$ and $R^{1c}$ are independently selected from:
 a) hydrogen,
 b) unsubstituted or substituted aryl, unsubstituted or substituted heterocycle, $C_3$–$C_{10}$ cycloalkyl, $C_2$–$C_6$ alkenyl, $C_2$–$C_6$ alkynyl, $R^8O$—, $R^9S(O)_m$—, $R^8C(O)NR^8$—, CN, $NO_2$, $(R^8)_2N$—$C(NR^8)$—, $R^8C(O)$—, $R^8OC(O)$—, $N_3$, —$N(R^8)_2$, or $R^9OC(O)NR^8$—,
 c) $C_1$–$C_6$ alkyl unsubstituted or substituted by unsubstituted or substituted aryl, heterocyclic, $C_3$–$C_{10}$ cycloalkyl, $C_2$–$C_6$ alkenyl, $C_2$–$C_6$ alkynyl, $R^8O$—, $R^9S(O)_m$—, $R^8C(O)NR^8$—, CN, $(R^8)_2N$—C$(NR^8)$—, $R^8C(O)$—, $R^8OC(O)$—, $N_3$, —$N(R^8)_2$, or $R^9OC(O)NR^8$—, provided that $R^{1a}$ is not unsubstituted or substituted imidazolyl;

$R^{2a}$, $R^{2b'}$ and $R^{2b''}$ are independently hydrogen or —$(CR^{11}_2)_v A^3(CR^{12}_2)_w R^{13}$; or $R^{2b'}$ and $R^{2b''}$ are combined as O;

$R^{3a}$ and $R^{3b}$ are independently selected from:
 a) hydrogen,
 b) unsubstituted or substituted aryl, unsubstituted or substituted heterocycle, unsubstituted or substituted $C_3$–$C_{10}$ cycloalkyl, unsubstituted or substituted $C_2$–$C_6$ alkenyl, $C_2$–$C_6$ alkynyl, halogen, $C_1$–$C_6$ perfluoroalkyl, $R^9O$—, $R^9S(O)_m$—, $R^8C(O)NR^8$—, $(R^8)_2NC(O)$—, $R^9C(O)O$—, $R^8_2N$—$C(NR^8)$—, CN, $NO_2$, $R^8C(O)$—, $N_3$, —$N(R^8)_2$, or $R^9OC(O)NR^8$—,
 c) unsubstituted $C_1$–$C_6$ alkyl,
 d) substituted $C_1$–$C_6$ alkyl wherein the substituent on the substituted $C_1$–$C_6$ alkyl is selected from unsubstituted or substituted aryl, unsubstituted or substituted heterocyclic, $C_3$–$C_{10}$ cycloalkyl, $C_2$–$C_6$ alkenyl, $C_2$–$C_6$ alkynyl, $R^9O$—, $R^9S(O)_m$—, $R^8C(O)NR^8$—, $(R^8)_2NC(O)$—, $R^8_2N$—$C(NR^8)$—, CN, $R^8C(O)$—, $N_3$, —$N(R^8)_2$, and $R^9OC(O)$—$NR^8$—;

$R^4$ is independently selected from:
 a) hydrogen,
 b) unsubstituted or substituted aryl, unsubstituted or substituted heterocycle, $C_3$–$C_{10}$ cycloalkyl, $C_2$–$C_6$ alkenyl, $C_2$–$C_6$ alkynyl, perfluoroalkyl, F, Cl, Br, $R^8O$—, $R^9S(O)_m$—, $R^8C(O)NR^8$—, CN, $NO_2$, $R^8_2N$—$C(NR^8)$—, $R^8C(O)$—, $R^8OC(O)$—, $N_3$, —$N(R^8)_2$, or $R^9OC(O)NR^8$—, and
 c) $C_1$–$C_6$ alkyl unsubstituted or substituted by aryl, heterocycle, $C_3$–$C_{10}$ cycloalkyl, $C_2$–$C_6$ alkenyl, $C_2$–$C_6$ alkynyl, perfluoroalkyl, F, Cl, Br, $R^8O$—, $R^9S(O)_m$—, $R^8C(O)NH$—, CN, $H_2N$—$C(NH)$—, $R^8C(O)$—, $R^8OC(O)$—, $N_3$, —$N(R^8)_2$, or $R^8OC(O)NH$—, provided that $R^4$ is not unsubstituted or substituted imidazolyl;

$R^5$ is independently selected from:
 a) hydrogen,
 b) $C_2$–$C_6$ alkenyl, $C_2$–$C_6$ alkynyl, $C_3$–$C_6$ cycloalkyl, perfluoroalkyl, F, Cl, Br, $R^8O$—, $R^9S(O)_m$—, $R^8C$ (O)NR⁸—, CN, NO₂, (R⁸)₂N—C—(NR⁸)—, R⁸C(O)—, R⁸OC(O)—, N₃, —N(R⁸)₂, or R⁹OC(O)NR⁸—, and c) C₁–C₆ alkyl, unsubstituted or substituted by perfluoroalkyl, F, Cl, Br, R⁸O—, R⁹S(O)ₘ—, R⁸C(O)NR⁸—, CN, (R⁸)₂N—C(NR⁸)—, R⁸C(O)—, R⁸OC(O)—, N₃, —N(R⁸)₂, or R⁹OC(O)NR⁸—;

R⁸ is independently selected from hydrogen, C₁–C₆ alkyl, benzyl, 2,2,2-trifluoroethyl and aryl;

R⁹ is independently selected from C₁–C₆ alkyl and aryl;

R¹⁰ is selected from: H; R⁸C(O)—; R⁹S(O)ₘ—; unsubstituted or substituted C₁₋₄ alkyl, unsubstituted or substituted C₃₋₆ cycloalkyl, unsubstituted or substituted heterocycle, unsubstituted or substituted aryl, substituted aroyl, unsubstituted or substituted heteroaroyl, substituted arylsulfonyl, unsubstituted or substituted heteroarylsulfonyl, wherein the substituted group is substituted with one or two substituents selected from:
a) C₁₋₄ alkoxy,
b) aryl or heterocycle,
c) halogen,
d) HO, e) 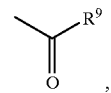

f) 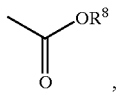

g) 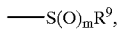

h) N(R⁸)₂, or
i) C₃₋₆ cycloalkyl;

R¹¹ and R¹² are independently selected from:
a) hydrogen,
b) C₁–C₆ alkyl unsubstituted or substituted by C₂–C₂₀ alkenyl, R⁸O—, R⁹S(O)ₘ—, R⁸C(O)NR⁸—, CN, N₃, (R⁸)₂N—C(NR⁸)—, R⁸C(O)—, —N(R⁸)₂, or R⁹OC(O)NR⁸—,
c) unsubstituted or substituted aryl, unsubstituted or substituted heterocycle, C₃–C₁₀ cycloalkyl, C₂–C₂₀ alkenyl, halogen, R⁸O—, R⁹S(O)ₘ—, R⁸C(O)NR⁸—, CN, NO₂, (R⁸)₂N—C(NR⁸)—, R⁸C(O)—, N₃, —N(R⁸)₂, or R⁹OC(O)NR⁸—, and
d) C₁–C₆ alkyl substituted with an unsubstituted or substituted group selected from aryl, heterocyclic and C₃–C₁₀ cycloalkyl;

R¹³ is selected from:
a) hydrogen,
b) substituted or unsubstituted aryl, substituted or unsubstituted heterocycle, C₃–C₁₀ cycloalkyl, C₂–C₂₀ alkenyl, C₂–C₂₀ alkynyl, C₁–C₂₀ perfluoroalkyl, allyloxy, F, Cl, Br, R⁸O—, R⁹S(O)ₘ—, R⁸C(O)NR⁸—, CN, NO₂, R⁸₂N—C(NR⁸)—, R⁸C(O)—, N₃, —N(R⁸)₂, (R⁹)₂NC(O)— or R⁹OC(O)NR⁸—, and
c) C₁–C₆ alkyl unsubstituted or substituted by substituted or unsubstituted aryl, substituted or unsubstituted heterocycle, C₃–C₁₀ cycloalkyl, C₂–C₂₀ alkenyl, C₂–C₂₀ alkynyl, C₂–C₂₀ perfluoroalkyl, F, Cl, Br, R⁸O—, R⁹S(O)ₘ—, R⁸C(O)NH—, CN, H₂N—C(NH)—, R⁸C(O)—, N₃, —N(R⁸)₂, or R⁹OC(O)NH—;

A¹ and A² are independently selected from: a bond, —CH=CH—, —C≡C—, —C(O)—, —C(O)NR⁸—, —NR⁸C(O)—, O, —N(R⁸)—, —S(O)₂N(R⁸)—, —N(R⁸)S(O)₂—, or —S(O)ₘ;

A³ are independently selected from: a bond, —CH=CH—, —C≡C—, —C(O)—, —C(O)NR¹⁰—, —NR¹⁰C(O)—, O, —N(R¹⁰)—, —S(O)₂N(R¹⁰)—, —N(R¹⁰)S(O)₂—, or —S(O)ₘ;

J-K-L represents CH=CH—S;

V is selected from:
a) hydrogen,
b) heterocycle,
c) aryl,
d) C₁–C₂₀ alkyl wherein from 0 to 4 carbon atoms are replaced with a heteroatom selected from O, S, and N, and
e) C₂–C₂₀ alkenyl, provided that V is not hydrogen if A¹ is —S(O)ₘ and V is not hydrogen if A¹ is a bond, n is 0 and A² is —S(O)ₘ; and provided that V is not imidazolyl;

W is imidazolyl;

X is a bond, —S(O)ₘ—, O or —C(=O)—;

m is 0, 1 or 2;

n is 0, 1, 2, 3 or 4;

p is 0, 1, 2, 3 or 4;

q is 0, 1,2,3 or 4, provided that q is not 0 or 1 if X is O;

r is 0 to 5, provided that r is 0 when V is hydrogen;

s is 1 or 2;

t is 1;

u is independently 0,1 or 2; provided that the sum of the u variables is equal to 2;

v is 0, 1, 2, 3 or 4, provided that v is not 0 when A³ is —NR¹⁰C(O)—, O, —N(R¹⁰)—, —S(O)₂N(R¹⁰)—, —N(R¹⁰)S(O)₂—, or S(O)ₘ;

w is 0, 1, 2, 3 or 4; and the dashed lines represent optional double bonds;
or an optical isomer or a pharrnaceutically acceptable salt thereof.

3. The compound according to claim 2 which inhibits farnesyl-protein transferase of the formula A:

A

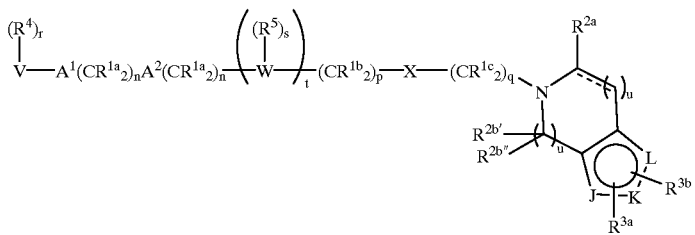

wherein:

$R^{1a}$ and $R^{1c}$ are independently selected from: hydrogen, $C_3-C_{10}$ cycloalkyl, $R^8O-$, $-N(R^8)_2$, F or $C_1-C_6$ alkyl;

$R^{1b}$ is independently selected from:
  a) hydrogen,
  b) unsubstituted or substituted aryl, unsubstituted or substituted heterocycle, $C_3-C_6$ cycloalkyl, $R^8O-$, $-N(R^8)_2$ or $C_2-C_6$ alkenyl,
  c) $C_1-C_6$ alkyl unsubstituted or substituted by unsubstituted or substituted aryl, heterocycle, $C_3-C_6$ cycloalkyl, $C_2-C_6$ alkenyl, $R^8O-$, or $-N(R^8)_2$;

$R^{2a}$ and $R^{2b'}$ are independently selected from selected from:
H; $C_1-C_6$ alkyl,

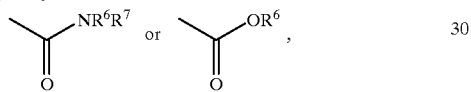

$R^{3a}$ and $R^{3b}$ are independently selected from:
  a) hydrogen,
  b) unsubstituted or substituted aryl, unsubstituted or substituted heterocycle, unsubstituted or substituted $C_3-C_{10}$ cycloalkyl, unsubstituted or substituted $C_2-C_6$ alkenyl, $C_2-C_6$ alkynyl, halogen, $C_1-C_6$ perfluoroalkyl, $R^9O-$, $R^9S(O)_m-$, $R^8C(O)NR^8-$, $(R^8)_2NC(O)-$, $R^9C(O)O-$, $R^8_2N-C(NR^8)-$, CN, $NO_2$, $R^8C(O)-$, $N_3$, $-N(R^8)_2$, or $R^9OC(O)NR^8-$,
  c) unsubstituted $C_1-C_6$ alkyl,
  d) substituted $C_1-C_6$ alkyl wherein the substituent on the substituted $C_1-C_6$ alkyl is selected from unsubstituted or substituted aryl, unsubstituted or substituted heterocyclic, $C_3-C_{10}$ cycloalkyl, $C_2-C_6$ alkenyl, $C_2-C_6$ alkynyl, $R^9O-$, $R^9S(O)_m-$, $R^8C(O)NR^8-$, $(R^8)_2NC(O)-$, $R^8_2N-C(NR^8)-$, CN, $R^8C(O)-$, $N_3$, $-N(R^8)_2$, and $R^9OC(O)-NR^8-$;

$R^4$ is independently selected from:
  a) hydrogen,
  b) $C_1-C_6$ alkyl, $C_2-C_6$ alkenyl, $C_2-C_6$ alkynyl, $C_1-C_6$ perfluoroalkyl, F, Cl, $R^8O-$, $R^8C(O)NR^8-$, CN, $NO_2$, $(R^8)_2N-C(NR^8)-$, $R^8C(O)-$, $R^8OC(O)-$, $-N(R^8)_2$, or $R^9OC(O)NR^8-$, and
  c) $C_1-C_6$ alkyl substituted by $C_1-C_6$ perfluoroalkyl, $R^8O-$, $R^8C(O)NR^8-$, $(R^8)_2N-C(NR^8)-$, $R^8C(O)-$, $R^8OC(O)-$, $-N(R^8)_2$, or $R^9OC(O)NR^8-$;

$R^5$ is selected from:
  a) hydrogen,
  b) $C_2-C_6$ alkenyl, $C_2-C_6$ alkynyl, $C_3-C_6$ cycloalkyl, $C_1-C_6$ perfluoroalkyl, F, Cl, $R^8O-$, $R^9S(O)_m-$, $R^8C(O)NR^8-$, CN, $NO_2$, $(R^8)_2N-C(NR^8)-$, $R^8C(O)-$, $R^8OC(O)-$, $-N(R^8)_2$, or $R^9OC(O)NR^8-$, and
  c) $C_1-C_6$ alkyl unsubstituted or substituted by $C_1-C_6$ perfluoroalkyl, F, Cl, $R^8O-$, $R^9S(O)_m-$, $R^8C(O)NR^8-$, CN, $(R^8)_2N-C(NR^8)-$, $R^8C(O)-$, $R^8OC(O)-$, $-N(R^8)_2$, or $R^9OC(O)NR^8-$;

$R^6$ and $R^7$ are independently selected from:
H; $C_{1-4}$ alkyl, $C_{3-6}$ cycloalkyl, aryl, heterocycle, unsubstituted or substituted with one or two:
  a) $C_{1-4}$ alkoxy,
  b) halogen, or
  c) substituted or unsubstituted aryl or substituted or unsubtituted heterocycle, $R^8$ is independently selected from hydrogen, $C_1-C_6$ alkyl, benzyl, 2,2,2-trifluoroethyl and aryl;

$R^9$ is independently selected from $C_1-C_6$ alkyl and aryl;

$R^{10}$ is selected from: H; $R^8C(O)-$; $R^9S(O)_m-$; unsubstituted or substituted $C_{1-4}$ alkyl, unsubstituted or substituted $C_{3-6}$ cycloalkyl, unsubstituted or substituted heterocycle, unsubstituted or substituted aryl, substituted aroyl, unsubstituted or substituted heteroaroyl, substituted arylsulfonyl, unsubstituted or substituted heteroarylsulfonyl, wherein the substituted group is substituted with one or two substituents selected from:
  a) $C_{1-4}$ alkoxy,
  b) aryl or heterocycle,
  c) halogen,
  d) HO,
  e)

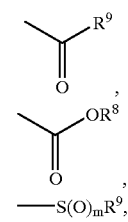

h) $N(R^8)_2$, or
  i) $C_{3-6}$ cycloalkyl;

$A^1$ and $A^2$ are independently selected from: a bond, $-CH=CH-$, $-C\equiv C-$, $-C(O)-$, $-C(O)NR^8-$, O, $-N(R^8)-$, or $-S(O)_m$;

J-K-L represents CH=CHS;

V is selected from:
  a) heterocycle selected from pyrrolidinyl, imidazolyl, pyridinyl, thiazolyl, indolyl, quinolinyl, isoquinolinyl, and thienyl, and
  b) aryl;

W is imidazolyl;

X is a bond, —S(O)$_m$—, O or —C(=O)—;

m is 0, 1 or 2;

n is 0, 1, 2, 3 or 4;

p is 1, 2 or 3;

q is 0, 1 or 2, provided that q is not 0 or 1 if X is O;

r is 0 to 5, provided that r is 0 when V is hydrogen;

s is 1 or 2;

t is 1; and u is 1;

or an optical isomer or a pharmaceutically acceptable salt thereof.

4. The compoLind according to claim 2 which inhibits farnesyl-protein transferase of the formula B:

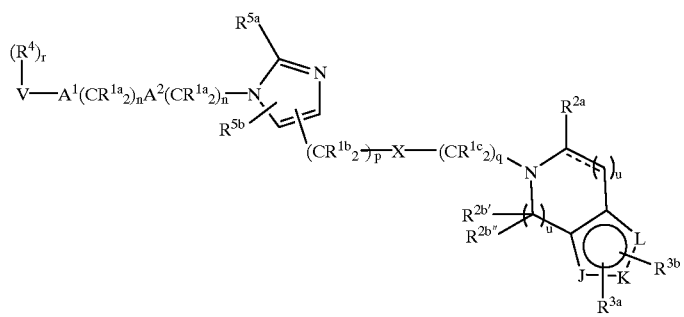

B wherein:

R$^{1a}$ and R$^{1c}$ are independently selected from: hydrogen, C$_3$–C$_{10}$ cycloalkyl, R$^8$O—, —N(R$^8$)$_2$, F or C$_1$–C$_6$ alkyl;

R$^{1b}$ is independently selected from:
a) hydrogen,
b) aryl, heterocycle, C$_3$–C$_{10}$ cycloalkyl, R$^8$O—, —N(R$^8$)$_2$, F or C$_2$–C$_6$ alkenyl,
c) unsubstituted or substituted C$_1$–C$_6$ alkyl wherein the substituent on the substituted C$_1$–C$_6$ alkyl is selected from unsubstituted or substituted aryl, heterocycle, C$_3$–C$_{10}$ cycloalkyl, C$_2$–C$_6$ alkenyl, R$^8$O— and —N(R$^8$)$_2$;

R$^{2a}$ and R$^{2b'}$ are independently selected from selected from:
H; C$_1$–C$_6$ alkyl,

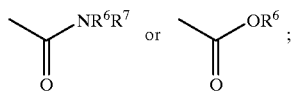

R$^{3a}$ and R$^{3b}$ are independently selected from:
a) hydrogen,
b) unsubstituted or substituted aryl, unsubstituted or substituted heterocycle, unsubstituted or substituted C$_3$–C$_{10}$ cycloalkyl, unsubstituted or substituted C$_2$–C$_6$ alkenyl, C$_2$–C$_6$ alkynyl, halogen, C$_1$–C$_6$ perfluoroalkyl, R$^9$O—, R$^9$S(O)$_m$—, R$^8$C(O)NR$^8$—, (R$^8$)$_2$NC(O)—, R$^9$C(O)O—, R$^8_2$N—C(NR$^8$)—, CN, NO$_2$, R$^8$C(O)—, N$_3$, —N(R$^8$)$_2$, or R$^9$OC(O)NR$^8$—,
c) unsubstituted C$_1$–C$_6$ alkyl,
d) substituted C$_1$–C$_6$ alkyl wherein the substituent on the substituted C$_1$–C$_6$ alkyl is selected from unsubstituted or substituted aryl, unsubstituted or substituted heterocyclic, C$_3$–C$_{10}$ cycloalkyl, C$_2$–C$_6$ alkenyl, C$_2$–C$_6$ alkynyl, R$^9$O—, R$^9$S(O)$_N$—, R$^8$C(O)NR$^8$—, (R$^8$)$_2$NC(O)—, R$^8_2$N—C(NR$^8$)—, CN, R$^8$C(O)—, N$_3$, —N(R$^8$)$_2$, and R$^9$OC(O)—NR$^8$—;

R$^4$ is independently selected from:
a) hydrogen,
b) aryl, substituted aryl, heterocycle, substituted heterocycle, C$_1$–C$_6$ alkyl, C$_2$–C$_6$ alkenyl, C$_2$–C$_6$ alkynyl, C$_1$–C$_6$ perfluoroalkyl, F, Cl, R$^8$O—, R$^8$C(O)NR$^8$—, CN, NO$_2$, (R$^8$)$_2$N—C(NR$^8$)—, R$^8$C(O)—, —N(R$^8$)$_2$, or R$^9$OC(O)NR$^8$—, and
c) C$_1$–C$_6$ alkyl substituted by C$_1$–C$_6$ perfluoroalkyl, R$^8$O—, R$^8$C(O)NR$^8$—, (R$^8$)$_2$N—C(NR$^8$)—, R$^8$C(O)—, —N(R$^8$)$_2$, or R$^9$OC(O)NR$^8$—;

R$^{5a}$ and R$^{5b}$ are independently hydrogen, C$_1$–C$_6$ alkyl, cyclopropyl, trifluoromethyl and halogen;

R$^6$ and R$^7$ are independently selected from:
H; C$_{1-4}$ alkyl, C$_{3-6}$ cycloalkyl, aryl, heterocycle, unsubstituted or substituted with one or two:
a) C$_{1-4}$ alkoxy,
b) halogen, or
c) substituted or unsubstituted aryl or substituted or unsubstituted heterocycle;

R$^8$ is independently selected from hydrogen, C$_1$–C$_6$ alkyl, 2,2,2-trifluoroethyl, benzyl and aryl;

R$^9$ is independently selected from C$_1$–C$_6$ alkyl and aryl;

A$^1$ and A$^2$ are independently selected from: a bond, —CH=CH—, —C≡C—, —C(O)—, —C(O)NR$^8$—, O, —N(R$^8$)—, or —S(O)$_m$;

J-K-L represents CH=CHS;

V is selected from:
a) hydrogen,
b) heterocycle selected from pyrrolidinyl, imidazolinyl, pyridinyl, thiazolyl, oxazolyl, indolyl, quinolinyl, isoquinolinyl, triazolyl and thienyl,
c) aryl,
d) C$_1$–C$_{20}$ alkyl wherein from 0 to 4 carbon atoms are replaced with a heteroatom selected from O, S, and N, and
e) C$_2$–C$_{20}$ alkenyl, and provided that V is not hydrogen if A$^1$ is —S(O)$_m$ and V is not hydrogen if A$^1$ is a bond, n is 0 and A$^2$ is —S(O)$_m$;

X is a bond, —S(O)$_m$—, O or —C(=O)—;

m is 0, 1 or 2;

n is 0, 1, 2, 3 or 4;

p is 0, 1, 2, 3 or 4;

q is 0 , 1 or 2, provided that q is not 0 or 1 if X is O;

r is 0 to 5, provided that r is 0 when V is hydrogen; and u is 1;

or an optical isomer or pharmaceutically acceptable salt thereof.

5. The compound according to claim 2 which inhibits farnesyl-protein transferase of the formula C:

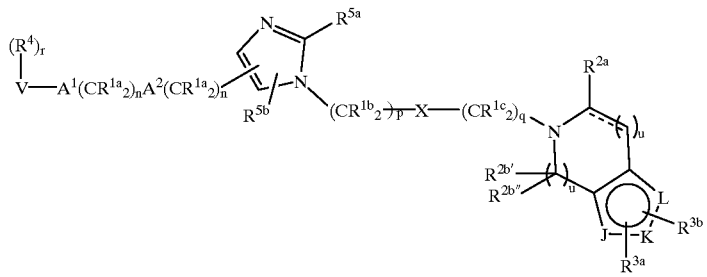

C wherein:
$R^{1a}$ and $R^{1c}$ are independently selected from: hydrogen, $C_3$–$C_{10}$ cycloalkyl, $R^8O$—, —$N(R^8)_2$, F or $C_1$–$C_6$ alkyl;
$R^{1b}$ is independently selected from:
 a) hydrogen,
 b) aryl, heterocycle, $C_3$–$C_{10}$ cycloalkyl, $R^8O$—, —$N(R^8)_2$, F or $C_2$–$C_6$ alkenyl,
 c) unsubstituted or substituted $C_1$–$C_6$ alkyl wherein the substituent on the substitued $C_1$–$C_6$ alkyl is selected from unsubstituted or substituted aryl, heterocycle, $C_3$–$C_{10}$ cycloalkyl, $C_2$–$C_6$ alkenyl, $R^8O$—and —$N(R^8)_2$;
$R^{2a}$ and $R^{2b'}$ are independently selected from selected from:
 H; $C_1$–$C_6$ alkyl,

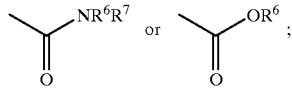

$R^{3a}$ and $R^{3b}$ are independently selected from:
 a) hydrogen,
 b) unsubstituted or substituted aryl, unsubstituted or substituted heterocycle, unsubstituted or substituted $C_3$–$C_{10}$ cycloalkyl, unsubstituted or substituted $C_2$–$C_6$ alkenyl, $C_2$–$C_6$ alkynyl, halogen, $C_1$–$C_6$ perfluoroalkyl, $R^9O$—, $R^9S(O)_m$—, $R^8C(O)NR^8$—, $(R^8)_2NC(O)$—, $R^9C(O)O$—, $R^8{}_2N$—$C(NR^8)$—, CN, $NO_2$, $R^8C(O)$—, $N_3$, —$N(R^8)_2$, or $R^9OC(O)NR^8$—,
 c) unsubstituted $C_1$–$C_6$ alkyl,
 d) substituted $C_1$–$C_6$ alkyl wherein the substituent on the substituted $C_1$–$C_6$ alkyl is selected from unsubstituted or substituted aryl, unsubstituted or substituted heterocyclic, $C_3$–$C_{10}$ cycloalkyl, $C_2$–$C_6$ alkenyl, $C_2$–$C_6$ alkynyl, $R^9O$—, $R^9S(O)_m$—, $R^8C(O)NR^8$—, $(R^8)_2NC(O)$—, $R^8{}_2N$—$C(NR^8)$—, CN, $R^8C(O)$—, $N_3$, —$N(R^8)_2$, and $R^9OC(O)$—$NR^8$—;
$R^4$ is independently selected from:
 a) hydrogen,
 b) aryl, substituted aryl, heterocycle, substituted heterocycle, $C_1$–$C_6$ alkyl, $C_2$–$C_6$ alkenyl, $C_2$–$C_6$ alkynyl, $C_1$–$C_6$ perfluoroalkyl, F, Cl, $R^8O$—, $R^8C(O)NR^8$—, CN, $NO_2$, $(R^8)_2N$—$C(NR^8)$—, $R^8C(O)$—, —$N(R^8)_2$, or $R^9OC(O)NR^8$—, and
 c) $C_1$–$C_6$ alkyl substituted by $C_1$–$C_6$ perfluoroalkyl, $R^8O$—, $R^8C(O)NR^8$—, $(R^8)_2N$—$C(NR^8)$—, $R^8C(O)$—, —$N(R^8)_2$, or $R^9OC(O)NR^8$—;

$R^{5a}$ and $R^{5b}$ are independently hydrogen, $C_1$–$C_6$ alkyl, cyclopropyl, trifluoromethyl and halogen;
$R^6$ and $R^7$ are independently selected from:

H; $C_{1-4}$ alkyl, $C_{3-6}$ cycloalkyl, aryl, heterocycle, unsubstituted or substituted with one or two:
 a) $C_{1-4}$ alkoxy,
 b) halogen, or
 c) substituted or unsubstituted aryl or substituted or unsubstituted heterocycle;
$R^8$ is independently selected from hydrogen, $C_1$–$C_6$ alkyl, 2,2,2-trifluoroethyl, benzyl and aryl;
$R^9$ is independently selected from $C_1$–$C_6$ alkyl and aryl;
$A^1$ and $A^2$ are independently selected from: a bond, —CH=CH—, —C≡C—, —C(O)—, —C(O)$NR^8$—, O, —$N(R^8)$—, or —$S(O)_m$;
J-K-L represents CH=CHS;
V is selected from:
 a) hydrogen,
 b) heterocycle selected from pyrrolidinyl, imidazolinyl, pyridinyl, thiazolyl, oxazolyl, indolyl, quinolinyl, isoquinolinyl, triazolyl and thienyl,
 c) aryl,
 d) $C_1$–$C_{20}$ alkyl wherein from 0 to 4 carbon atoms are replaced with a heteroatom selected from O, S, and N, and
 e) $C_2$–$C_{20}$ alkenyl, and provided that V is not hydrogen if $A_1$ is —$S(O)_m$ and V is not hydrogen if $A_1$ is a bond, n is 0 and $A^2$ is —$S(O)_m$;

X is a bond, —$S(O)_m$—, O or —$C(=O)$—;
m is 0, 1 or 2;
n is 0, 1, 2, 3 or 4;
p is 0, 1, 2, 3 or 4, provided that p is not 0 if X is a bond or O;
q is 0, 1 or 2, provided that q is not 0 or 1 if X is O;
r is 0 to 5, provided that r is 0 when V is hydrogen; and
u is 1;

or an optical isomer or pharmaceutically acceptable salt thereof.

6. The compound according to claim 4 which inhibits farnesyl-protein transferase of the formula D:

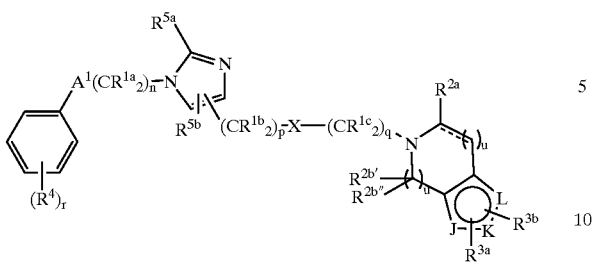

D wherein:
$R^{1a}$ and $R^{1c}$ are independently selected from: hydrogen, $C_3$–$C_{10}$ cycloalkyl or $C_1$–$C_6$ alkyl;

$R^{1b}$ is independently selected from:
  a) hydrogen,
  b) aryl, heterocycle, $C_3$–$C_{10}$ cycloalkyl, $R^8O$—, —$N(R^8)_2$, F or $C_2$–$C_6$ alkenyl,
  c) $C_1$–$C_6$ alkyl unsubstituted or substituted by aryl, heterocycle, $C_3$–$C_{10}$ cycloalkyl, $C_2$–$C_6$ alkenyl, $R^8O$—, or —$N(R^8)_2$;

$R^{2a}$ and $R^{2b'}$ are independently selected from selected from:
H; $C_1$–$C_6$ alkyl,

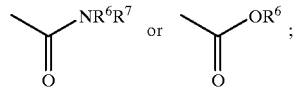

$R^{3a}$ and $R^{3b}$ are independently selected from:
  a) hydrogen,
  b) unsubstituted or substituted aryl, unsubstituted or substituted heterocycle, unsubstituted or substituted $C_3$–$C_{10}$ cycloalkyl, unsubstituted or substituted $C_2$–$C_6$ alkenyl, $C_2$–$C_6$ alkynyl, halogen, $C_1$–$C_6$ perfluoroalkyl, $R^9O$—, $R^9S(O)_m$—, $R^8C(O)NR^8$—, $(R^8)_2NC(O)$—, $R^9C(O)O$—, $R^8_2N$—$C(NR^8)$—, CN, $NO_2$, $R^8C(O)$—, $N_3$, —$N(R^8)_2$, or $R^9OC(O)NR^8$—,
  c) unsubstituted $C_1$–$C_6$ alkyl,
  d) substituted $C_1$–$C_6$ alkyl wherein the substituent on the substituted $C_1$–$C_6$ alkyl is selected from unsubstituted or substituted aryl, unsubstituted or substituted heterocyclic, $C_3$–$C_{10}$ cycloalkyl, $C_2$–$C_6$ alkenyl, $C_2$–$C_6$ alkynyl, $R^9O$—, $R^9S(O)_m$—, $R^8C(O)NR^8$—, $(R^8)_2NC(O)$—, $R^8_2N$—$C(NR^8)$—, CN, $R^8C(O)$—, $N_3$, —$N(R^8)_2$, and $R^9OC(O)$—$NR^8$—;

$R^4$ is independently selected from:
  a) hydrogen,
  b) aryl, substituted aryl, heterocycle, substituted heterocycle, $C_1$–$C_6$ alkyl, $C_2$–$C_6$ alkenyl, $C_2$–$C_6$ alkynyl, $C_1$–$C_6$ perfluoroalkyl, F, Cl, $R^8O$—, $R^8C(O)NR^8$—, CN, $NO_2$, $(R^8)_2N$—$C(NR^8)$—, $R^8C(O)$—, —$N(R^8)_2$, or $R^9OC(O)NR^8$—, and
  c) $C_1$–$C_6$ alkyl substituted by $C_1$–$C_6$ perfluoroalkyl, $R^8O$—, $R^8C(O)NR^8$—, $(R^8)_2N$—$C(NR^8)$—, $R^8C(O)$—, —$N(R^8)_2$, or $R^9OC(O)NR^8$—;

$R^{5a}$ and $R^{5b}$ are independently hydrogen, ethyl, cyclopropyl or methyl;

$R^6$ and $R^7$ are independently selected from:
H; $C_{1-4}$ alkyl, $C_{3-6}$ cycloalkyl, aryl, heterocycle, unsubstituted or substituted with one or two:
  a) $C_{1-4}$ alkoxy,
  b) halogen, or
  c) substituted or unsubstituted aryl or substituted or unsubstituted heterocycle;

$R^8$ is independently selected from hydrogen, $C_1$–$C_6$ alkyl, 2,2,2-trifluoroethyl, benzyl and aryl;

$R^9$ is independently selected from $C_1$–$C_6$ alkyl and aryl;

$A^1$ is selected from: a bond, —C(O)—, O, —$N(R^8)$—, or —$S(O)_m$;

J-K-L represents CH=CHS;

X is a bond, —$S(O)_m$—, O or —C(=O)—;

n is 0, 1 or 2; provided that n is not 0 or 1 if $A^1$ is a bond, O, —$N(R^8)$—, or $S(O)_m$;

m is 0, 1 or 2;

p is 0, 1, 2, 3 or 4;

q is 0, 1 or 2, provided that q is not 0 or 1 if X is O;

r is 1 or 2; and u is 1;

or an optical isomer or pharmaceutically acceptable salt thereof.

7. The compound according to claim 5 which inhibits farnesyl-protein transferase of the formula E:

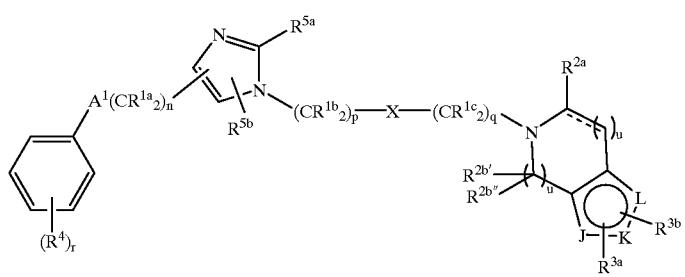

E wherein:

$R^{1a}$ and $R^{1c}$ are independently selected from: hydrogen, $R^8O$—, —$N(R^8)_2$, F, $C_3$–$C_{10}$ cycloalkyl or $C_1$–$C_6$ alkyl;

$R^{1b}$ is independently selected from:
  a) hydrogen,
  b) aryl, heterocycle, $C_3$–$C_{10}$ cycloalkyl, $R^8O$—, —$N(R^8)_2$, F or $C_2$–$C_6$ alkenyl,
  c) $C_1$–$C_6$ alkyl unsubstituted or substituted by aryl, heterocycle, $C_3$–$C_{10}$ cycloalkyl, $C_2$–$C_6$ alkenyl, $R^8O$—, or —$N(R^8)_2$;

$R^{2a}$ and $R^{2b'}$ are independently selected from selected from:

H; C$_1$–C$_6$ alkyl,

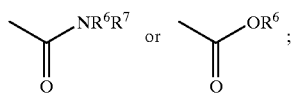

R$^{3a}$ and R$^{3b}$ are independently selected from:
a) hydrogen,
b) unsubstituted or substituted aryl, unsubstituted or substituted heterocycle, unsubstituted or substituted C$_3$–C$_{10}$ cycloalkyl, unsubstituted or substituted C$_2$–C$_6$ alkenyl, C$_2$–C$_6$ alkynyl, halogen, C$_1$–C$_6$ perfluoroalkyl, R$^9$O—, R$^9$S(O)$_m$—, R$^8$C(O)NR$^8$—, (R$^8$)$_2$NC(O)—, R$^9$C(O)O—, R$^8{}_2$N—C(NR$^8$)—, CN, NO$_2$, R$^8$C(O)—, N$_3$, —N(R$^8$)$_2$, or R$^9$OC(O)NR$^8$—,
c) unsubstituted C$_1$–C$_6$ alkyl,
d) substituted C$_1$–C$_6$ alkyl wherein the substituent on the substituted C$_1$–C$_6$ alkyl is selected from unsubstituted or substituted aryl, unsubstituted or substituted heterocyclic, C$_3$–C$_{10}$ cycloalkyl, C$_2$–C$_6$ alkenyl, C$_2$–C$_6$ alkynyl, R$^9$O—, R$^9$S(O)$_m$—, R$^8$C(O)NR$^8$—, (R$^8$)$_2$NC(O)—, R$^8{}_2$N—C(NR$^8$)—, CN, R$^8$C(O)—, N$_3$, —N(R$^8$)$_2$, and R$^9$OC(O)—NR$^8$—;

R$^4$ is independently selected from:
a) hydrogen,
b) aryl, substituted aryl, heterocycle, substituted heterocycle, C$_1$–C$_6$ alkyl, C$_2$–C$_6$ alkenyl, C$_2$–C$_6$ alkynyl, C$_1$–C$_6$ perfluoroalkyl, F, Cl, R$^8$O—, R$^8$C(O)NR$^8$—, CN, NO$_2$, (R$^8$)$_2$N—C(NR$^8$)—, R$^8$C(O)—, —N(R$^8$)$_2$, or R$^9$OC(O)NR$^8$—, and
c) C$_1$–C$_6$ alkyl substituted by C$_1$–C$_6$ perfluoroalkyl, R$^8$O—, R$^8$C(O)NR$^8$—, (R$^8$)$_2$N—C(NR$^8$)—, R$^8$C(O)—, —N(R$^8$)$_2$, or R$^9$OC(O)NR$^8$—;

R$^{5a}$ and R$^{5b}$ are independently hydrogen, ethyl, cyclopropyl or methyl;

R$^6$ and R$^7$ are independently selected from:
H; C$_{1-4}$ alkyl, C$_{3-6}$ cycloalkyl, aryl, heterocycle, unsubstituted or substituted with one or two:
a) C$_{1-4}$ alkoxy,
b) halogen, or
c) substituted or unsubstituted aryl or substituted or unsubstituted heterocycle;

R$^8$ is independently selected from hydrogen, C$_1$–C$_6$ alkyl, 2,2,2-trifluoroethyl, benzyl and aryl;

R$^9$ is independently selected from C$_1$–C$_6$ alkyl and aryl;

J-K-L represents CH=CHS;

X is a bond, —S(O)$_m$—, O or —C(=O)—;

n is 0 or 1;

m is 0, 1 or 2;

p is 0, 1, 2, 3 or 4, provided that p is not 0 if X is a bond or O;

q is 0, 1 or 2, provided that q is not 0 or 1 if X is O;

r is 1 or 2; and u is 1;

or an optical isomer or pharmaceutically acceptable salt thereof.

8. The compound according to claim 6 which inhibits farnesyl-protein transferase of the formula F:

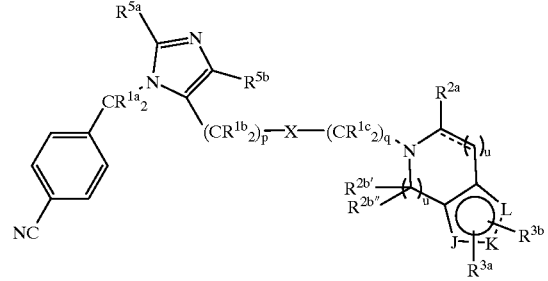

wherein:

R$^{1a}$ and R$^{1c}$ are independently selected from: hydrogen, C$_3$–C$_{10}$ cycloalkyl or C$_1$–C$_6$ alkyl;

R$^{1b}$ is independently selected from:
a) hydrogen,
b) aryl, heterocycle, C$_3$–C$_{10}$ cycloalkyl, R$^8$O—, —N(R$^8$)$_2$ or F,
c) C$_1$–C$_6$ alkyl unsubstituted or substituted by aryl, heterocycle, C$_3$–C$_{10}$ cycloalkyl, R$^8$O—, or —N(R$^8$)$_2$;

R$^{2a}$ and R$^{2b'}$ are independently selected from selected from: H; C$_1$–C$_6$ alkyl,

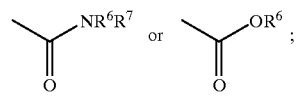

R$^{3a}$ and R$^{3b}$ are independently selected from:
a) hydrogen,
b) unsubstituted or substituted aryl, unsubstituted or substituted heterocycle, unsubstituted or substituted C$_3$–C$_{10}$ cycloalkyl, unsubstituted or substituted C$_2$–C$_6$ alkenyl, C$_2$–C$_6$ alkynyl, halogen, C$_1$–C$_6$ perfluoroalkyl, R$^9$O—, R$^9$S(O)$_m$—, R$^8$C(O)NR$^8$—, (R$^8$)$_2$NC(O)—, R$^9$C(O)O—, R$^8{}_2$N—C(NR$^8$)—, CN, NO$_2$, R$^8$C(O)—, N$_3$, —N(R$^8$)$_2$, or R$^9$OC(O)NR$^8$—,
c) unsubstituted C$_1$–C$_6$ alkyl,
d) substituted C$_1$–C$_6$ alkyl wherein the substituent on the substituted C$_1$–C$_6$ alkyl is selected from unsubstituted or substituted aryl, unsubstituted or substituted heterocyclic, C$_3$–C$_{10}$ cycloalkyl, C$_2$–C$_6$ alkenyl, C$_2$–C$_6$ alkynyl, R$^9$O—, R$^9$S(O)$_m$—, R$^8$C(O) NR$^8$—, (R$^8$)$_2$NC(O)—, R$^8{}_2$N—C(NR$^8$)—, CN, R$^8$C (O)—, N$_3$, —N(R$^8$)$_2$, and R$^9$OC(O)—NR$^8$—;

R$^{5a}$ and R$^{5b}$ are independently hydrogen, ethyl, cyclopropyl or methyl;

R$^6$ and R$^7$ are independently selected from:
H; C$_{1-4}$ alkyl, C$_{3-6}$ cycloalkyl, aryl, heterocycle, unsubstituted or substituted with one or two:
a) C$_{1-4}$ alkoxy,
b) halogen, or
c) substituted or unsubstituted aryl or substituted or unsubstituted heterocycle;

R$^8$ is independently selected from hydrogen, C$_1$–C$_6$ alkyl, 2,2,2-trifluoroethyl, benzyl and aryl;

R$^9$ is independently selected from C$_1$–C$_6$ alkyl and aryl;

J-K-L represents CH=CHS;

X is a bond, —S(O)$_m$—, O or —C(=O)—;

m is 0, 1 or 2;

p is 0, 1, 2, 3 or 4;

q is 0, 1 or 2, provided that q is not 0 or 1 if X is O; and u is 1;

or an optical isomer or phanna(eutically acceptable salt thereof.

9. The compound according to claim 7 which inhibits farnesyl-protein transferase of the formula G:

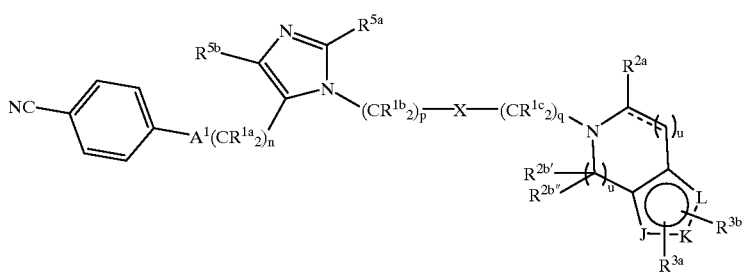

wherein:

$R^{1a}$ and $R^{1c}$ are independently selected from: hydrogen, $R^8O$—, —$N(R^8)_2$, F, $C_3$–$C_{10}$ cycloalkyl or $C_1$–$C_6$ alkyl;

$R^{1b}$ is independently selected from:
 a) hydrogen,
 b) aryl, heterocycle or $C_3$–$C_{10}$ cycloalkyl,
 c) $C_1$–$C_6$ alkyl unsubstituted or substituted by aryl, heterocycle, $C_3$–$C_{10}$ cycloalkyl, $C_2$–$C_6$ alkenyl, $R^8O$—, or —$N(R^8)_2$;

$R^{2a}$ and $R^{2b'}$ are independently sclected from selected from: H; $C_1$–$C_6$ alkyl,

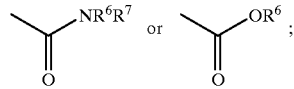

$R^{3a}$ and $R^{3b}$ are independently selected from:
 a) hydrogen,
 b) unsubstituted or substituted aryl, unsubstituted or substituted heterocycle, unsubstituted or substituted $C_3$–$C_{10}$ cycloalkyl, unsubstituted or substituted $C_2$–$C_6$ alkenyl, $C_2$–$C_6$ alkynyl, halogen, $C_1$–$C_6$ perfluoroalkyl, $R^9O$—, $R^9S(O)_m$—, $R^8C(O)NR^8$—, $(R^8)_2NC(O)$—, $R^9C(O)O$—, $R^8_2N$—$C(NR^8)$—, CN, $NO_2$, $R^8C(O)$—, $N_3$, —$N(R^8)_2$, or $R^9OC(O)NR^8$—,
 c) unsubstituted $C_1$–$C_6$ alkyl,
 d) substituted $C_1$–$C_6$ alkyl wherein the substituent on the substituted $C_1$–$C_6$ alkyl is selected from unsubstituted or substituted aryl, unsubstituted or substituted heterocyclic, $C_3$–$C_{10}$ cycloalkyl, $C_2$–$C_6$ alkenyl, $C_2$–$C_6$ alkynyl, $R^9O$—, $R^9S(O)_m$—, $R^8C(O)$$NR^8$—, $(R^8)_2NC(O)$—, $R^8_2N$—$C(NR^8)$—, CN, $R^8C(O)$—, $N_3$, —$N(R^8)_2$, and $R^9OC(O)$—$NR^8$—;

$R^{5a}$ and $R^{5b}$ are independently hydrogen, ethyl, cyclopropyl or methyl;

$R^6$ and $R^7$ are independently selected from:
 H; $C_{1-4}$ alkyl, $C_{3-6}$ cycloalkyl, aryl, heterocycle, unsubstituted or substituted with one or two:
  a) $C_{1-4}$ alkoxy,
  b) halogen, or
  c) substituted or unsubstituted aryl or substituted or unsubstituted heterocycle;

$R^8$ is independently selected from hydrogen, $C_1$–$C_6$ alkyl, 2,2,2-trifluoroethyl, benzyl and aryl;

$R^9$ is independently selected from $C_1$–$C_6$ alkyl and aryl;

J-K-L represents CH=CHS;

$A^1$ is selected from: a bond, —C(O)—, O, —$N(R^8)$—, or —$S(O)_m$;

X is a bond, —$S(O)_m$—, O or —C(=O)—;

m is 0, 1 or 2;

n is 0, 1 or 2; provided that n is not 0 if $A^1$ is a bond, O, —$N(R^8)$—, or $S(O)_m$;

p is 1, 2 or 3;

q is 0, 1 or 2, provided that q is not 0 or 1 if X is O; and u is 1;

or an optical isomer or pharnaceutically acceptable salt thereof.

10. A compound which inhibits farnesyl-protein transferase which is:

5-(1-(4-Cyanobenzyl)-5-imidazolylmethyl)-4,5,6,7-tetrahydrothieno[3,2-c]pyridine

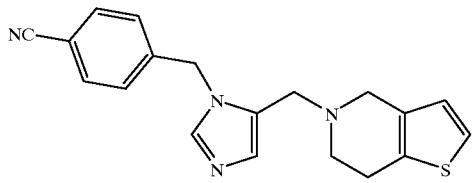

2-Bromo-5-(1-(4-cyanobenzyl)-5-imidazolylmethyl)-4,5,6,7-tetrahydrothieno[3,2-c]pyridine

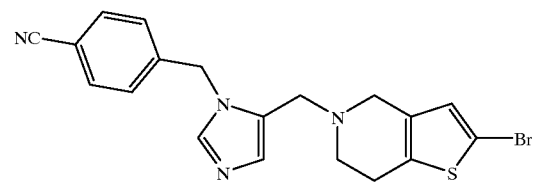

2-Phenyl-5-(1-(4-cyanobenzyl)-5-imidazolylmethyl)-4,5,6,7-tetrahydrothieno[3,2-c]pyridine

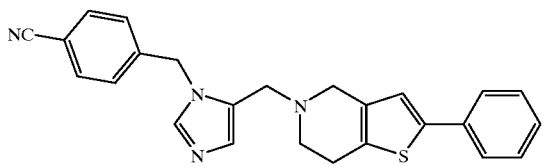

or a pharmaceutically acceptable salt thereof.

11. A pharmaceutical composition comprising a pharmaceutical carrier, and dispersed therein, a therapeutically effective amount of a compound of claim 1.

12. A pharmaceutical composition comprising a pharmaceutical carrier, and dispersed therein, a therapeutically effective amount of a compound of claim 2.

13. A pharmaceutical composition comprising a pharmaceutical carrier, and dispersed therein, a therapeutically effective amount of a compound of claim 4.

14. A pharmaceutical composition comprising a pharmaceutical carrier, and dispersed therein, a therapeutically effective amount of a compound of claim 5.

15. A pharmaceutical composition comprising a pharmaceutical carrier, and dispersed therein, a therapeutically effective amount of a compound of claim 10.

16. A method for inhibiting farnesyl-protcin transferase which comprises administering to a mammal in need thereof a therapeutically effective amount of a composition of claim 11.

17. A method for inhibiting farnesyl-protein transferase which comprises administering to a mammal in need thereof a therapeutically effective amount of a composition of claim 12.

18. A method for inhibiting farnesyl-protein transferase which comprises administering to a mammal in need thereof a therapeutically effective amount of a composition of claim 13.

19. A method for inhibiting farnesyl-protein transferase which comprises administering to a mammal in need thereof a therapeutically effective amount of a composition of claim 14.

20. A method for inhibiting farnesyl-protein transferase which comprises administering to a mammal in need thereof a therapeutically effective amount of a composition of claim 15.

21. A method for treating cancer which comprises administering to a mammal in need thereof a therapeutically effective amount of a composition of claim 11.

22. A method for treating cancer which comprises administering to a mammal in need thereof a therapeutically effective amount of a composition of claim 12.

23. A method for treating cancer which comprises administering to a mammal in need thereof a therapeutically effective amount of a composition of claim 13.

24. A method for treating cancer which comprises administering to a mammal in need thereof a therapeutically effective amount of a composition of claim 14.

25. A method for treating cancer which comprises administering to a mammal in need thereof a therapeutically effective amount of a composition of claim 15.

26. A method for treating neurofibromin benign proliferative disorder which comprises administering to a mammal in need thereof a therapeutically effective amount of a composition of claim 11.

27. A method for treating blindness related to retinal vascularization which comprises administering to a mammal in need thereof a therapeutically effective amount of a composition of claim 11.

28. A method for treating infections from hepatitis delta and related viruses which comprises administering to a mammal in need thereof a therapeutically effective amount of a composition of claim 11.

29. A method for preventing restenosis which comprises administering to a mammal in need thereof a therapeutically effective amount of a composition of claim 11.

30. A method for treating polycystic kidney disease which comprises administering to a mammal in need thereof a therapeutically effective amount of a composition of claim 11.

* * * * *

UNITED STATES PATENT AND TRADEMARK OFFICE

CERTIFICATE OF CORRECTION

PATENT NO. :  6,015,817

DATED:  January 18, 2000

INVENTOR(S):  Wasyl Halczenko and Craig A. Stump

It is certified that errors by the USPTO appear in the above identified patent and that said Letters Patent is hereby corrected as shown below:

(1) In column 64, claim 1, line 19 should read:
-- stituted $C_{3-6}$ cycloalkyl, unsubstituted or substituted -- .

(2) In column 72, claim 4, line 3 should read:
-- alkenyl, $C_2$-$C_6$ alkynyl, $R^9O$-, $R^9S(O)_m$-, $R^8C$ -- .

(3) In column 79, claim 8, line 4 should read:
-- or an optical isomer pharmaceutically acceptable salt --

Signed and Sealed this

Tenth Day of April, 2001

*Attest:*

NICHOLAS P. GODICI

*Attesting Officer*  Acting Director of the United States Patent and Trademark Office